US012611384B2

(12) United States Patent
Monteiro

(10) Patent No.: US 12,611,384 B2
(45) **Date of Patent: *Apr. 28, 2026**

(54) ANTIMICROBIAL NANOWORMS

(71) Applicant: THE BOEING COMPANY, Chicago, IL (US)

(72) Inventor: Michael Monteiro, Bellevue, WA (US)

(73) Assignee: THE BOEING COMPANY, Arlington, VA (US)

( * ) Notice: Subject to any disclaimer, the term of this patent is extended or adjusted under 35 U.S.C. 154(b) by 819 days.

This patent is subject to a terminal disclaimer.

(21) Appl. No.: 17/642,721

(22) PCT Filed: Sep. 3, 2020

(86) PCT No.: PCT/US2020/049208

§ 371 (c)(1),
(2) Date: Mar. 14, 2022

(87) PCT Pub. No.: WO2021/050355

PCT Pub. Date: Mar. 18, 2021

(65) Prior Publication Data

US 2022/0331262 A1 Oct. 20, 2022

Related U.S. Application Data

(60) Provisional application No. 63/049,813, filed on Jul. 9, 2020, provisional application No. 62/899,983, filed on Sep. 13, 2019.

(51) Int. Cl.

| | |
|---|---|
| ***A61K 9/70*** | (2006.01) |
| ***A61K 31/137*** | (2006.01) |
| ***A61K 31/4188*** | (2006.01) |
| ***A61K 38/48*** | (2006.01) |
| ***A61K 38/50*** | (2006.01) |
| ***A61K 47/58*** | (2017.01) |
| ***A61K 47/59*** | (2017.01) |

(52) U.S. Cl.

CPC .............. *A61K 9/70* (2013.01); *A61K 31/137* (2013.01); *A61K 31/4188* (2013.01); *A61K 38/48* (2013.01); *A61K 38/50* (2013.01); *A61K 47/58* (2017.08); *A61K 47/595* (2017.08)

(58) Field of Classification Search

CPC ........ A61K 9/70; A61K 47/58; A61K 47/595; A61K 31/137; A61K 31/4188; A61K 38/48; A61K 38/50

See application file for complete search history.

(56) References Cited

U.S. PATENT DOCUMENTS

| | | | |
|---|---|---|---|
| 2018/0362462 A1 | 12/2018 | Monteiro et al. | |
| 2023/0114159 A1 | 4/2023 | Stevens et al. | |

FOREIGN PATENT DOCUMENTS

| | | | | |
|---|---|---|---|---|
| JP | 2015519902 A | 7/2015 | | |
| WO | 2018187515 A1 | 10/2018 | | |
| WO | WO-2018232005 A2 * | 12/2018 | ............ | A01N 47/02 |
| WO | 2021050355 A1 | 3/2021 | | |

OTHER PUBLICATIONS

Z. Jia, V. A. Bobrin, N. P. Truongi, M. Gillard, and M. J. Monteiro "Multifunctional Nanoworms and Nanorods through a One-Step Aqueous Dispersion Polymerization," J. Am. Chem. Soc. 2014, 136, 5824-5827 (Year: 2014).*

Carlo Ballatore, Donna M. Huryn, and Amos B. Smith III. "Carboxylic Acid (Bio) Isosteres in Drug Design." ChemMedChem. Mar. 2013 ; 8(3): 385-395. (Year: 2013).*

Japanese Patent Office, Office Action for Japanese Patent Application No. 2022-516310, dated Jul. 16, 2024.

Gu et al., "Aug. 30, Biodistribution of PNIPAM Coated Nanostructures Synthesized by the TDMT Method", Biomacromolecules, 2018 / 634,DOI: 10.1021/acs.biomac.8b01196 , vol. 20, No. 2,p. 625.

Zhongfan Jia et al: "Mulitfunctional Nanoworms and Nanorods through a One-Step Aqueous Dispersion Polymerization," Journal of The American Chemical Society, vol. 136, No. 16, dated Feb. 6, 2014 (Feb. 6, 2014), pp. 5824-5827 [Abstract Only].

PCT, International Search Report for Application PCT/US2020/049208 dated Dec. 21, 2020.

PCT, Notification Concerning Transmittal of International Preliminary Report on Patentability (Chapter 1 of The Patent Cooperation Treaty) for Application PCT/US2020/049208 dated Mar. 15, 2022.

Penfold et al., "Cross-linked Cationic Diblock Copolymer Worms are Superflocculants for Micrometer-sized Silica," Chem. Sci., 2016, 7, 6894-6904.

Penfold et al., "Layer-By-Layer Self-Assembly of Polyelectrolytic Block Copolymer Worms on a Planar Substrate," ACS Langmuir, 2017, 33, 14425-14436.

Semsarilar et al., "Cationic Polyelectrolyte-Stabilized Nanoparticles via Raft Aqueous Dispersion Polymerization," ACS Langmuir, 2013, 29, 7416-7424.

(Continued)

*Primary Examiner* — Michael P Cohen

(74) *Attorney, Agent, or Firm* — MH2 Technology Law Group LLP

(57) ABSTRACT

At least one nanoworm comprises a plurality of alkene units and a plurality of macroCTA polymer units. The macroCTA polymer units include $R^1$ groups from reversible addition-fragmentation chain-transfer agents. In certain aspects, the $R^1$ groups of the macroCTA polymer units are functional groups, such as a carboxylic acid, an alkyne, a pyridine, a dopamine, a thiolactone, a biotin, an azide, a peptide sequence, a sugar sequence, a protease, a glycanase, a polymer, other functional groups, and combinations thereof. In certain aspects, the macroCTA polymer units comprise quaternized amines. In certain aspects, the macroCTA polymer units comprise functionalized quaternized amines, such as an alkyl group, a carboxylic acid, an alkyne, a pyridine, a dopamine, a thiolactone, a biotin, an azide, a peptide sequence, a sugar sequence, a protease, a glycanase, a polymer, other functional groups, and combinations thereof. In certain aspects, the coating comprises the at least one nanoworm.

20 Claims, 28 Drawing Sheets

Specification includes a Sequence Listing.

(56) References Cited

OTHER PUBLICATIONS

Notice of Reasons for Refusal issued Apr. 8, 2025 in corresponding Japanese Application No. 2022-516310 (in both English and Japanese), 17 pages.
Japanese Notice of Reasons for Refusal for Japanese Application No. 2022-516310 dated Nov. 4, 2025, 8 pages including English machine translation.
Zhang et al., "Modular Monomers with Tunable Solubility: Synthesis of Highly Incompatible Block Copolymer Nano-Objects via Raft Aqueous Dispersion Polymerization," ACS Macro Letters, 2017 (Published Feb. 17, 2017), vol. 6, pp. 224-228.

* cited by examiner

```
                         SEQUENCE LISTING


<160> NUMBER OF SEQ ID NOS: 32

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Lys Lys Ala Ala Val Ala Leu Leu Pro Ala Val Leu Leu Ala
1               5                   10                  15

Leu Leu Ala Pro
            20


<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Lys Lys Leu Ala Val Leu Leu Ala Leu Leu Ala
1               5                   10


<210> SEQ ID NO 3
<211> LENGTH: 7
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 3

Asn Asp Phe Arg Ser Lys Thr
1               5


<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Asn Asp Phe Arg Ser Lys Thr Cys
1               5


<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Leu Val Phe Phe Val Ile Phe Tyr Phe Phe Arg
1               5                   10


<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Leu Val Phe Phe Val Ile Ala Tyr Phe Ala Arg
1               5                   10


<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Leu Val Phe Phe Val Ile Phe Tyr Phe Phe Arg Arg Arg Lys Lys
1               5                   10                  15


<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Arg Lys Lys Trp Leu Val Phe Phe Val Ile Phe Tyr Phe Phe Arg
1               5                   10                  15
```

-continued

```
<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Arg Lys Lys Ile Phe Tyr Phe Phe Arg
1               5                   10


<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Leu Val Phe Phe Val Arg Arg Lys Lys
1               5                   10


<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Phe Val Ile Phe Tyr Arg Arg Lys Lys
1               5                   10


<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2
<220> FEATURE:
<221> NAME/KEY: SITE
<222> LOCATION: (1)..(1)
<223> OTHER INFORMATION: Residue linked to C17H35CO

<400> SEQUENCE: 12

Ala Arg Leu Pro Arg Thr Met Val His Pro Lys Pro Ala Gln Pro
1               5                   10                  15


<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(1)
<223> OTHER INFORMATION: Residue linked to C16

<400> SEQUENCE: 13

Ala Arg Leu Pro Arg Thr Met Val His Pro Lys Pro Ala Gln Pro
1               5                   10                  15
```

```
<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(1)
<223> OTHER INFORMATION: Residue linked to C16

<400> SEQUENCE: 14

Ala Arg Leu Pro Arg Thr Met Val
1               5


<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(1)
<223> OTHER INFORMATION: Residue linked to C16

<400> SEQUENCE: 15

Ala Arg Leu Pro Arg
1               5


<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Cys Lys Lys Tyr Arg Arg Phe Arg Trp Lys Phe Lys Gly Lys Phe
1               5                   10                  15

Trp Phe Trp Gly
            20


<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Lys Lys Tyr Arg Arg Phe Arg Trp Lys Phe Lys Gly Lys Trp Phe
1               5                   10                  15

Trp Phe Gly


<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

-continued

Gly Phe Trp Phe Lys Gly Lys Trp Arg Phe Lys Lys Tyr Arg Gly Gly
1 5 10 15

Arg Tyr Lys Lys Phe Arg Trp Lys Gly Lys Phe Trp Phe Gly
20 25 30

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Ser Ser Asn Lys Ser Thr Thr Gly Ser Gly Glu Thr Thr Thr Ala
1 5 10 15

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

Ala Cys Tyr Cys Arg Ile Pro Ala Cys Ile Ala Gly Glu Arg Arg Tyr
1 5 10 15

Gly Thr Cys Ile Tyr Gln Gly Arg Leu Trp Ala Phe Cys Cys
20 25 30

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Ser Lys His Ser Ser Leu Asp Cys Val Leu Arg Pro
1 5 10

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Ala Gly Asp Asp Gln Gly Leu Asp Lys Cys Val Pro Asn Ser Lys Glu
1 5 10 15

Lys

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

-continued

```
Asn Gly Glu Ser Ser Ala Asp Trp Ala Lys Asn
1               5                   10


<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Phe Arg Leu Ile Lys Ser Leu Ile Lys Arg Leu Val Ser Ala Phe
1               5                   10                  15

Lys


<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35


<210> SEQ ID NO 26
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Asp Val Asn Pro Thr Leu Leu Phe Leu Lys Val Pro Ala Gln Asn
1               5                   10                  15

Ala Ile Ser Thr Thr Phe Pro Tyr Thr
            20                  25


<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Glu Arg Ile Lys Glu Leu Arg Asp Leu Met Ser Trp Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly
        35


<210> SEQ ID NO 28
<211> LENGTH: 27
```

-continued

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Ser Gly Arg Ile Lys Lys Glu Glu Phe Ala Glu Ile Met Lys Ile
1               5                   10                  15

Cys Ser Thr Ile Glu Glu Leu Gly Arg Gln Lys
            20                  25

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Asp Val Asn Pro Tyr Leu Leu Phe Leu Lys Val Pro Ala Gln
1               5                   10                  15

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Lys Val Thr Met Thr Cys Ser Ala Ser
1               5                   10

<210> SEQ ID NO 31
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Ala Thr Cys Glu Gln Ile Ala Asp Ser Gln His Arg Ser His Arg
1               5                   10                  15

Gln Met Val

ANTIMICROBIAL NANOWORMS

CROSS-REFERENCE TO RELATED APPLICATIONS

This application is a U.S. National Stage Application under 35 U.S.C. 371 of PCT/US2020/049208, filed Nov. 12, 2020, which claims benefit of and priority to U.S. provisional patent application Ser. No. 62/899,983, filed Sep. 13, 2019 and to U.S. provisional patent application Ser. No. 63/049,813, filed Jul. 9, 2020, both provisional patent applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 22, 2026, is named 0192_0516_SL.txt and is 10,099 bytes in size.

FIELD

The present disclosure provides an antimicrobial nanoworm, such as a coating of antimicrobial nanoworms over a surface of a vehicle, a building, a wearable, a filter, or any object.

BACKGROUND

Pandemics by viruses (e.g., SARS, SARS-CoV-2, Swine Flu, and Ebola) have major impact to the global economy by reducing airline passenger traffic. Seasonal flu and aircraft cabin sterility are also ongoing concerns by airline passengers. Similarly, the space transportation and habitation industry are concerned with preventing the transmission of microbes. Travelers in space may become more easily immunosuppressed with a greater susceptibility to disease transmission by microbes. In addition, microbes may replicate more and become more virulent in a zero gravity environment or a radiation shielded environment.

Preventing disease transmission on aircrafts and spacecrafts has conventionally focused on improvements of the air filtration systems, such as HEPA air filter systems. Replacing and maintaining HEPA filters may be costly or impractical, such as replacing and maintaining HEPA filters in space. Moreover, such systems may be ineffective to reduce or stop the transmission of microbes from surfaces. Bacteria and viruses can linger on surfaces for days and even up to a week.

Therefore, there is a need for antimicrobial surface coatings that are effective on reducing the transmission of microbes.

SUMMARY

The present disclosure provides a nanoworm, such as a coating of antimicrobial nanoworms over a surface of a vehicle, a building, a wearable, a filter, or any object.

At least one nanoworm comprises a plurality of alkene units and a plurality of macroCTA polymer units. The macroCTA polymer units include $R^1$ groups from reversible addition-fragmentation chain-transfer agents. In certain aspects, the $R^1$ groups of the macroCTA polymer units are functional groups, such as a carboxylic acid, an alkyne, a pyridine, a dopamine, a thiolactone, a biotin, an azide, a peptide sequence, a sugar sequence, a protease, a glycanase, a polymer, other functional groups, and/or combinations thereof. In certain aspects, the macroCTA polymer units comprise quaternized amines. In certain aspects, the macroCTA polymer units comprise functionalized quaternized amines, such as an alkyl group, a carboxylic acid, an alkyne, a pyridine, a dopamine, a thiolactone, a biotin, an azide, a peptide sequence, a sugar sequence, a protease, a glycanase, a polymer, other functional groups, and/or combinations thereof. In certain aspects, the coating comprises the at least one nanoworm.

At least one nanoworm comprises a plurality of alkene units, a first set of a plurality of macroCTA polymer units, and a second set of a plurality of macroCTA polymer units. The macroCTA polymer units of the first set and the second set include $R^1$ groups from reversible addition-fragmentation chain-transfer agents. The first set of the plurality of macroCTA polymers units is different from the second set of the plurality of macroCTA polymers units. In certain aspects, the $R^1$ groups of the macroCTA polymer units are functional groups, such as a carboxylic acid, an alkyne, a pyridine, a dopamine, a thiolactone, a biotin, an azide, a peptide sequence, a sugar sequence, a protease, a glycanase, a polymer, other functional groups, and/or combinations thereof. In certain aspects, the macroCTA polymer units comprise quaternized amines. In certain aspects, the macroCTA polymer units comprise functionalized quaternized amines, such as an alkyl group, a carboxylic acid, an alkyne, a pyridine, a dopamine, a thiolactone, a biotin, an azide, a peptide sequence, a sugar sequence, a protease, a glycanase, a polymer, other functional groups, and/or combinations thereof. In certain aspects, the coating comprises the at least one nanoworm.

At least one nanoworm comprises a plurality of alkene units, a plurality of macroCTA polymer units, and a plurality of grafted polymers. The macroCTA polymer units of the first set include $R^1$ groups from reversible addition-fragmentation chain-transfer agents. The plurality of grafted polymers is grafted to at least a portion of the first set of the plurality of macroCTA polymer units. In certain aspects, the $R^1$ groups of the macroCTA polymer units are functional groups, such as a carboxylic acid, an alkyne, a pyridine, a dopamine, a thiolactone, a biotin, an azide, a peptide sequence, a sugar sequence, a protease, a glycanase, a polymer, the grafted polymer, other functional groups, and/or combinations thereof. In certain aspects, the macroCTA polymer units and/or grafted polymer units comprise quaternized amines. In certain aspects, the macroCTA polymer units and/or grafted polymers comprise functionalized quaternized amines, such as an alkyl group, a carboxylic acid, an alkyne, a pyridine, a dopamine, a thiolactone, a biotin, an azide, a peptide sequence, a sugar sequence, a protease, a glycanase, a polymer, other functional groups, and/or combinations thereof. In certain aspects, the macroCTA polymer units comprise functionalized quaternized amines including the grafted polymers. In certain aspects, the coating comprises the at least one nanoworm.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only typical aspects of this present disclosure and are therefore not to be considered limiting of its scope, for the present disclosure may admit to other equally effective aspects.

Figure 1:
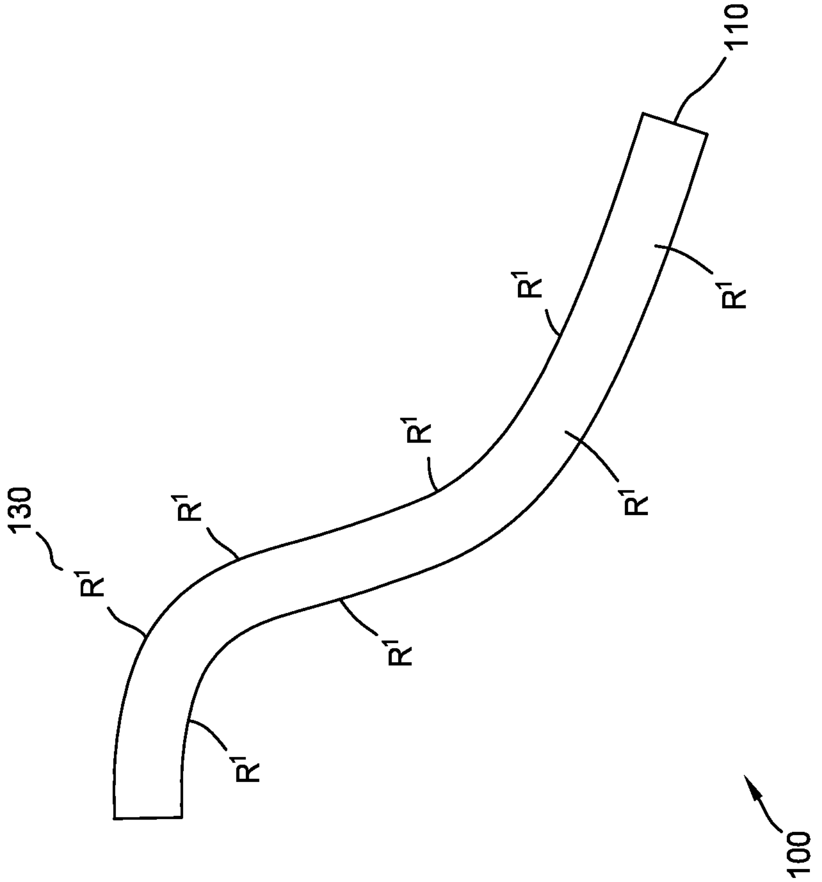
FIG. 1 is a schematic view illustrating a nanoworm according to certain aspects.

To facilitate understanding, identical reference numerals have been used, where possible, to designate identical elements that are common to the figures. The figures are not drawn to scale and may be simplified for clarity. It is contemplated that elements and features of one aspect may be beneficially incorporated in other aspects without further recitation.

DETAILED DESCRIPTION

Usage in the Summary of the Disclosure or in the Detailed Description of the term “comprising” shall mean comprising, consisting essentially, and/or consisting of.

The present disclosure provides a nanoworm, such as a coating of antimicrobial nanoworms over a surface of a vehicle, a building, a wearable, a filter, or any object. The nanoworms have antimicrobial properties effective at reducing or killing of microbes and/or reducing the transmission of microbes, Microbes can be viruses, bacteria, fungi, and/or other germs.

In certain aspects, a nanoworm coated surface is or can become a hydrophilic surface. For example, a nanoworm coated surface is or can become hydrophilic allowing the wetting of a droplet, such as a mucosal drop, blood, urine, sweat, other bodily fluids, and other non-bodily fluids, across the nanoworm coated surface. In certain aspects, microbes on the surface of the droplet or suspended within the droplet can be captured and/or killed by the nanoworm coated surface.

In certain aspects, a nanoworm coated surface responds to environmental conditions of a droplet and surrounding external conditions. For example, a nanoworm coated surface can respond to one or more environmental triggers, such as temperature, pH, salinity concentration, and/or light, to aid in the capture and killing of microbes. For instance, as a droplet evaporates, a nanoworm coated surface can change state from hydrophilic to water-insoluble. The change in state from hydrophilic to water-insoluble can enhance the capture and killing of microbes within a droplet. For example, one or more nanoworms of a nanoworm coated surface can have multiple adhesion or contact points to a microbe in which the change from hydrophilic to water-insoluble can exert a mechanical strain onto a microbe to dissociate or disassemble the microbe.

In certain aspects, a chemical composition and functionality of a plurality of nanoworms can be selected to enhance the capturing and killing of microbes. For example, a nanoworm coated surface can be chemically modified with a carboxylic acid group, an alkyne, a pyridine, a dopamine, a thiolactone, a biotin, an azide, a peptide sequence (including one or more amino acids and/or combinations thereof), a nucleic acid sequence (including one or more nucleic acids and/or combinations thereof), a sugar sequence (including one or more monosugars, polysugars, and/or combinations thereof), a protease, a glycanase, a grafted polymer, quaternized amine groups, derivatives thereof, and/or combinations thereof, to capture/kill a broad range of microbes or to capture/kill a certain microbe, such as in response to a certain outbreak of a virus.

A nanoworm coating can be non-toxic. For example, a nanoworm coated surface is antimicrobial without being toxic to humans, animals, and/or plants. For example, antimicrobial compounds of a nanoworm coated surface are covalently bonded to the nanoworms. Since the nanoworms are strongly adhered to the surface, the antimicrobial compounds of a nanoworm coated surface are prevented from being ingested or absorbed by skin into the human body.

In certain aspects, a nanoworm coating can be washable by being able to be washed and re-used. For example, a nanoworm coated surface can be washed with water (e.g., rinsed), cleaning agents (e.g., detergents, soaps, and surfactants), sanitizers, and/or disinfectants. A nanoworm coated surface can be washed to renew the nanoworm coated surface by removing captured or killed microbes from antimicrobial compounds of the nanoworms. Renewed nanoworms can capture and kill additional microbes which land on the nanoworm coated surface. For example, the antimicrobial compounds can be selected to capture and kill without covalent attachment to the microbe. Therefore, washing the nanoworms releases captured or killed microbes from the antimicrobial compounds and allows the antimicrobial compounds to be renewed for capture and killing of additional microbes.

In certain aspects, a nanoworm comprises a copolymer of a macro chain transfer agent (macroCTA) polymer units and alkene units. A macroCTA polymer is a polymer formed by reversible addition-fragmentation chain-transfer (RAFT) utilizing a RAFT agent in the polymerization of one or more ethylenically unsaturated monomers. In certain aspects, the RAFT agent is incorporated in the macroCTA polymer which can be further polymerized with the addition of reactants.

In certain aspects, a RAFT agent is represented by the general formula (I):

(I)

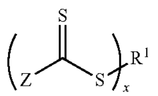

wherein $R^1$ is an x-valent group in which x is an integer≥1. The $R^1$ group can be mono-valent, di-valent, tri-valent or of higher valency. In certain aspects, x is an integer ranging from 1 to 20, such as from 1 to 10, or such as from 1 to 5. Accordingly, $R^1$ can be an optionally substituted polymer chain with the remainder of the RAFT agent presented as multiple groups pendant from the polymer chain. The $R^1$ group can be an organic group or a substituted organic group that functions as a free radical leaving group under the polymerization conditions employed. The Z groups can independently be selected from the group consisting of organic groups and/or substituted organic groups that function to give a suitably high reactivity of the C═S moiety in the RAFT agent towards free radical addition.

Examples of $R^1$ of formula (I) include optionally substituted alkyl, alkenyl, alkynyl, aryl, acyl, carbocyclyl, heterocyclyl, heteroaryl, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkylacyloxy, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkylalkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, alkylthioaryl, alkenylthioaryl, alkynylthioaryl, arylthioaryl, arylacylthio, arylcarbocyclylthio, arylheterocyclylthio, arylheteroarylthio, and a polymer chain.

Examples of $R^1$ of formula (I) include optionally substituted alkyl; saturated, unsaturated, or aromatic carbocyclic or heterocyclic ring; alkylthio; dialkylamino; an organometallic species; and a polymer chain.

Specific examples of $R^1$ of formula (I) include optionally substituted $C_1$-$C_{18}$ alkyl, $C_2$-$C_{18}$ alkenyl, $C_2$-$C_{18}$ alkynyl, $C_6$-$C_{18}$ aryl, $C_1$-$C_{18}$ acyl, $C_3$-$C_{18}$ carbocyclyl, $C_2$-$C_{18}$ heterocyclyl, $C_3$-$C_{18}$ heteroaryl, $C_1$-$C_{18}$ alkylthio, $C_2$-$C_{18}$ alkenylthio, $C_2$-$C_{18}$ alkynylthio, $C_6$-$C_{18}$ arylthio, $C_1$-$C_{18}$ acylthio, $C_3$-$C_{18}$ carbocyclylthio, $C_2$-$C_{18}$ heterocyclylthio, $C_3$-$C_{18}$ heteroarylthio, $C_3$-$C_{18}$ alkylalkenyl, $C_3$-$C_{18}$ alkylalkynyl, $C_7$-$C_{24}$ alkylaryl, $C_2$-$C_{18}$ alkylacyl, alkylcarbocyclyl, $C_3$-$C_{18}$ alkylheterocyclyl, $C_4$-$C_{18}$ alkylheteroaryl, $C_2$-$C_{18}$ alkyloxyalkyl, $C_3$-$C_{18}$ alkenyloxyalkyl, $C_2$-$C_{18}$ alkynyloxyalkyl, $C_7$-$C_{24}$ aryloxyalkyl, $C_2$-$C_{18}$ alkylacyloxy, $C_2$-$C_{18}$ alkylthioalkyl, $C_3$-$C_{18}$ alkenylthioalkyl, $C_3$-$C_{18}$ alkynylthioalkyl, $C_7$-$C_{24}$ arylthioalkyl, $C_2$-$C_{18}$ alkylacylthio, $C_4$-$C_{18}$ alkylcarbocyclylthio, $C_3$-$C_{18}$ alkylheterocyclylthio, $C_4$-$C_{18}$ alkylheteroarylthio, $C_4$-$C_{18}$ alkylalkenylalkyl, $C_4$-$C_{18}$ alkylalkynylalkyl, $C_8$-$C_{24}$ alkylarylalkyl, $C_3$-$C_{18}$ alkylacylalkyl, $C_{13}$-$C_{24}$ arylalkylaryl, $C_{14}$-$C_{24}$ arylalkenylaryl, $C_{14}$-$C_{24}$ arylalkynylaryl, $C_{13}$-$C_{24}$ arylacylaryl, $C_7$-$C_{18}$ arylacyl, $C_9$-$C_{18}$ arylcarbocyclyl, $C_8$-$C_{18}$ arylheterocyclyl, $C_9$-$C_{18}$ arylheteroaryl, $C_8$-$C_{18}$ alkenyloxyaryl, $C_8$-$C_{18}$ alkynyloxyaryl, $C_{12}$-$C_{24}$ aryloxyaryl, $C_7$-$C_{18}$ alkylthioaryl, $C_8$-$C_{18}$ alkenylthioaryl, $C_8$-$C_{18}$ alkynylthioaryl, $C_{12}$-$C_{24}$ arylthioaryl, $C_7$-$C_{18}$ arylacylthio, $C_9$-$C_{18}$ arylcarbocyclylthio, $C_8$-$C_{18}$ arylheterocyclylthio, $C_9$-$C_{18}$ arylheteroarylthio, and a polymer chain having a number average molecular weight in the range of about 500 to about 80,000, for example in the range of about 500 to about 30,000.

Examples of Z of formula (I) include F, Cl, Br, I, alkyl, aryl, acyl, amino, carbocyclyl, heterocyclyl, heteroaryl, alkyloxy, aryloxy, acyloxy, acylamino, carbocyclyloxy, heterocyclyloxy, heteroaryloxy, alkylthio, arylthio, acylthio, carbocyclylthio, heterocyclylthio, heteroarylthio, alkylaryl, alkylacyl, alkylcarbocyclyl, alkylheterocyclyl, alkylheteroaryl, alkyloxyalkyl, aryloxyalkyl, alkylacyloxy, alkylcarbocyclyloxy, alkylheterocyclyloxy, alkylheteroaryloxy, alkylthioalkyl, arylthioalkyl, alkylacylthio, alkylcarbocyclylthio, alkylheterocyclylthio, alkylheteroarylthio, alkylarylalkyl, alkylacylalkyl, arylalkylaryl, arylacylaryl, arylacyl, arylcarbocyclyl, arylheterocyclyl, arylheteroaryl, aryloxyaryl, arylacyloxy, arylcarbocyclyloxy, arylheterocyclyloxy, arylheteroaryloxy, alkylthioaryl, arylthioaryl, arylacylthio, arylcarbocyclylthio, arylheterocyclylthio, arylheteroarylthio, dialkyloxy-, diheterocyclyloxy- or diaryloxy-phosphinyl, dialkyl-, diheterocyclyl- or diaryl-phosphinyl, cyano (i.e. —CN), and —S—R, where R is as defined with respect to formula (I).

Specific examples of Z of formula (I) include F, Cl, and optionally substituted $C_1$-$C_{18}$ alkyl, $C_6$-$C_{18}$ aryl, $C_1$-$C_{18}$ acyl, amino, $C_3$-$C_{18}$ carbocyclyl, $C_2$-$C_{18}$ heterocyclyl, $C_3$-$C_{18}$ heteroaryl, $C_1$-$C_{18}$ alkyloxy, $C_3$-$C_{18}$ aryloxy, acyloxy, $C_3$-$C_{18}$ carbocyclyloxy, $C_2$-$C_{18}$ heterocyclyloxy, $C_3$-$C_{18}$ heteroaryloxy, $C_1$-$C_{18}$ alkylthio, $C_6$-$C_{18}$ arylthio, $C_1$-$C_{18}$ acylthio, $C_3$-$C_{18}$ carbocyclylthio, $C_2$-$C_{18}$ heterocyclylthio, $C_3$-$C_{18}$ heteroarylthio, $C_7$-$C_{24}$ alkylaryl, $C_2$-$C_{18}$ alkylacyl, $C_4$-$C_{18}$ alkylcarbocyclyl, $C_3$-$C_{18}$ alkylheterocyclyl, $C_4$-$C_{18}$ alkylheteroaryl, $C_2$-$C_{18}$ alkyloxyalkyl, $C_7$-$C_{24}$ aryloxyalkyl, $C_2$-$C_{18}$ alkylacyloxy, $C_4$-$C_{18}$ alkylcarbocyclyloxy, $C_3$-$C_{18}$ alkylheterocyclyloxy, $C_4$-$C_{18}$ alkylheteroaryloxy, $C_2$-$C_{18}$ alkylthioalkyl, $C_7$-$C_{24}$ arylthioalkyl, $C_2$-$C_{18}$ alkylacylthio, $C_4$-$C_{18}$ alkylcarbocyclylthio, $C_3$-$C_{18}$ alkylheterocyclylthio, $C_4$-$C_{18}$ alkylheteroarylthio, $C_8$-$C_{24}$ alkylarylalkyl, $C_3$-$C_{18}$ alkylacylalkyl, $C_{13}$-$C_{24}$ arylalkylaryl, $C_{13}$-$C_{24}$ arylacylaryl, $C_7$-$C_{18}$ arylacyl, $C_9$-$C_{18}$ arylcarbocyclyl, $C_8$-$C_{18}$ arylheterocyclyl, $C_9$-$C_{18}$ arylheteroaryl, $C_{12}$-$C_{24}$ aryloxyaryl, $C_7$-$C_{18}$ arylacyloxy, $C_9$-$C_{18}$ arylcarbocyclyloxy, $C_8$-$C_{18}$ arylheterocyclyloxy, $C_9$-$C_{18}$ arylheteroaryloxy, $C_7$-$C_{18}$ alkylthioaryl, $C_{12}$-$C_{24}$ arylthioaryl, $C_7$-$C_{18}$ arylacylthio, $C_9$-$C_{18}$ arylcarbocyclylthio, $C_8$-$C_{18}$ arylheterocyclylthio, $C_9$-$C_{18}$ arylheteroarylthio, dialkyloxy-, diheterocyclyloxy- or diaryloxy-phosphinyl (i.e. $—P(═O)OR^k_2$), dialkyl-, diheterocyclyl- or diaryl-phosphinyl (i.e. $—P(═O)R^k_2$), where $R^k$ is selected from optionally substituted $C_1$-$C_{18}$ alkyl, optionally substituted $C_6$-$C_{18}$ aryl, optionally substituted $C_2$-$C_{18}$ heterocyclyl, and optionally substituted $C_7$-$C_{24}$ alkylaryl, cyano (i.e. —CN), and —S—R, where R is as defined in respect of formula (I).

In the examples of $R^1$ and Z, it is understood that multi-component groups include sub-groups of any order. For instance, the multi-component group of alkylaryls includes arylalkyls. The $R^1$ or Z can be branched and/or optionally substituted. Where the $R^1$ or Z comprises an optionally substituted alkyl moiety, an optional substituent includes where a $—CH_2—$ group in the alkyl chain is replaced by a group selected from —O—, —S—, $—NR^a—$, —C(O)— (i.e. carbonyl), —C(O)O— (i.e. ester), and $—C(O)NR^a—$ (i.e. amide), where $R^a$ can be selected from hydrogen, alkyl, alkenyl, alkynyl, aryl, carbocyclyl, heteroaryl, heterocyclyl, arylalkyl, and acyl.

Reference herein to an x-valent, multi-valent or di-valent "form of . . . " is intended to mean that the specified group is an x-valent, multi-valent or di-valent radical, respectively. For example, where x is 2, the specified group is intended to be a divalent radical. In that case, a divalent alkyl group is in effect an alkylene group (e.g. $—CH_2—$), Similarly, the divalent form of the group alkylaryl can, for example, be represented by $—(C_6H_4)—CH_2—$, a divalent alkylarylalkyl group can, for example, be represented by $—CH_2—(C_6H_4)—CH_2—$, a divalent alkyloxy group can, for example, be represented by $—CH_2—O—$, and a divalent alkyloxyalkyl group can, for example, be represented by $—CH_2—O—CH_2—$, Where the term "optionally substituted" is used in combination with such an x-valent, multivalent or di-valent group, that group can be substituted or fused as herein described. Where the x-valent, multi-valent, di-valent groups comprise two or more subgroups, for example [group A][group B][group C] (e.g. alkylarylalkyl), if viable one or more of such subgroups can be optionally substituted.

In certain aspects, part or all of the RAFT agent is incorporated into the macroCTA polymer. In certain aspects, $R^1$ and —S—(S═O)—Z are incorporated into the macroCTA polymer. Examples of RAFT polymerized macroCTAs include, but are not limited to, poly(N-isopropylacrylamide) (PNIPAM), poly(N,N-(dimethylamino)ethyl methacrylate) (F), poly(N-acetoxylethyl acrylamide) (PNAEAA), poly(acryloylglycine ethyl ester) (PNAGEE), poly((ethylene glycol)methyl ether methacrylate) (PEGMEMA), poly((propylene glycol)methacrylate) (PPGMA), poly(N,N-dimethylacrylamide) (PDMA), poly(N-decylacrylamide) (PDcA), poly(N,N-diethylacrylamide) (PDEA), poly(N-acryloylglycine) (PNAG), poly(N-acryloylglycine methyl ester) (PNAGME), poly(N-acryloylglycine ethyl ester) (PNAGEE) and poly(N-acryloylglycine propyl ester) (PNAGPE), other polyacrylamides, other polyacrylates, and copolymers thereof.

For example, a macroCTA comprising poly(NIPAM) has the general formula (II):

(II)

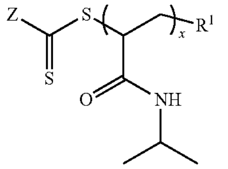

$Z—(C═S)—S—(NIPAM)_x—R^1$ in which Z and $R^1$ (including functionalized or functionalized $R^1$ groups) are components of a RAFT agent. In certain aspects, x is any positive integer. In certain aspects, x is an integer from 10 to 100.

For example, a macroCTA comprising a poly(NIPAM-co-DMAEMA) has the general formula (III):

(III)

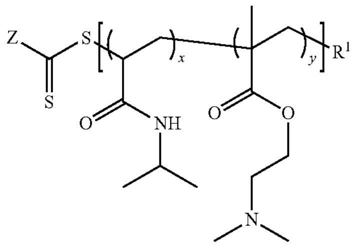

$Z—(C═S)—S—[(NIPAM)_x—(DMAEMA)_y]—R^1$ in which Z and $R^1$ (including unfunctionalized or functionalized $R^1$ groups) are components of a RAFT agent. In certain aspects, x and y are any independently selected positive integers. In certain aspects, x is an integer from 10 to 100, and y is an integer from 10 to 100. The sequence of the monomers of the macroCTA copolymer, such as the NIPAM and DMAEMA monomers of a macroCTA copolymer of formula (III) can be any sequence, such as in a random, alternating, statistical, periodic, or block sequence.

In certain aspects, a macroCTA polymer is used to form a nanoworm by further polymerizing macroCTA polymer units and alkene monomers. For example, a nanoworm can be produced by first producing macroCTA polymer units with a RAFT agent in which the RAFT agent is incorporated into each macroCTA polymer unit. The macroCTA polymer units and alkene monomers are polymerized together to form a nanoworm. The RAFT agent incorporated into the macroCTA polymerizes the alkene units and the macroCTA units to form a nanoworm of the general formula (IV):

$$\text{(Alkene Units)}_m\text{(MacroCTA Units)}_n \quad \text{(IV)}$$

in which each of the macroCTA includes a unfunctionalized or functionalized $R^1$ group as a component of a RAFT agent. The nanoworm includes the macroCTA units, the alkene units, and components of the RAFT agents. The alkene units and the MacroCTA units can be formed into the nanoworm in any sequence, such as in a random, alternating, statistical, periodic, or block sequence.

The polyalkene is formed by polymerization of any suitable alkene monomers and/or combinations thereof. Examples of suitable alkene monomers include ethylene, propylene, 1-butene, 1-pentene, 4-methyl-1-pentene, 1-hexene, 1-heptene, 1-octene, 1-decene, norbornene, styrenes, acrylates, methacrylates, other vinyl compounds, substituted compounds thereof, and derivatives thereof. In certain aspects, polyalkene units of a nanoworm comprises m monomer units from 20 to 400 alkene monomer units, such as from 25 to 35 alkene monomer units. In certain aspects, the polyalkene comprises polystyrene. In certain aspects, m and n are any independently selected positive integers. In certain aspects, MacroCTA units of a nanoworm comprises n MacroCTA units from 1 to 200, such as from 2 to 100.

For example, a nanoworm comprising a polystyrene and a macroCTA of poly(NIPAM-co-DMEA) has the general formula (V):

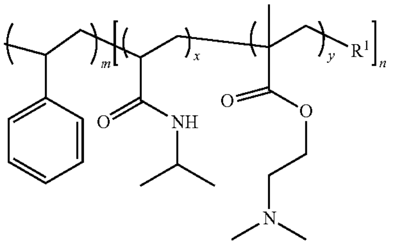

(styrene)$_m$[(NIPAM)$_x$—(DMAEMA)$_y$—$R^1$]$_n$ in which $R^1$ is an unfunctionalized or functionalized $R^1$ group as a component of a RAFT agent. In certain aspects, x, y, m, and n are any independently selected positive integers. In certain aspects, x is an integer from 10 to 100, y is an integer from 10 to 100, m is an integer from 20 to 400, and n is an integer from 1 to 200.

The macroCTA polymer units can be selected to provide certain properties to a nanoworm. The macroCTA polymer units can be configured to respond to temperature, pH, salinity concentration, light, and/or combinations thereof. For example, a macroCTA polymer unit can change miscibility with a droplet based upon temperature alone or based upon temperature, pH, salinity concentration, light, and/or other external environmental conditions.

In certain aspects, the macroCTA polymer units can contain temperature-responsive monomers and/or functional groups in any suitable amount. A temperature-responsive macroCTA polymer unit can have a LCST, an upper critical solution temperature (UCST), or both a LCST and a UCST. Examples of temperature-responsive monomers or functional groups include those having amine functional groups, carbonyl functional groups, and/or combinations thereof. In certain aspects, the macroCTA polymer units have an LCST in water from about −20° C. to about +100° C.

In certain aspects, the macroCTA units can contain pH-responsive monomers and/or functional groups in any suitable amount. Examples of pH-responsive monomers include vinyl monomers such as acrylic acid, methacrylic acid, and other alkyl-substituted acrylic acids, maleic anhydride, maleic acid, 2-acrylamido-2-methyl-I-propanesulfonic acid, N-vinyl formamide, N-vinyl acetamide, aminoethyl methacrylate, phosphoryl ethyl acrylate, or methacrylate. Other examples of pH-responsive monomers include polypeptides derived from amino acids (e.g. polylysine and polyglutamic acid), polysaccharides (e.g. alginic acid, hyaluronic acid, carrageenan, chitosan, carboxymethyl, and cellulose), or nucleic acids (e.g., deoxyribonucleic acid (DNA), ribonucleic acid (RNA), messenger RNA (mRNA), and fragments thereof). Examples of pH sensitive functional groups include, but are not limited to $—OPO(OH)_2$, —COOH, or $—NH_2$.

In certain aspects, the macroCTA polymer units can contain saline-responsive monomers and/or functional groups in any suitable amount. Examples of saline-responsive monomers and/or functional groups include ureido amides, amines, carboxylic acid side groups, and other functional groups. Examples of a saline-responsive macroCTA polymer unit include LCST polymers and/or UCST polymers.

In certain aspects, the macroCTA polymer units can contain light-responsive monomers and/or functional groups in any suitable amount. Examples of light-responsive monomers and/or functional groups include those with chromophoric functional groups. Chromophoric functional groups are any functional groups that are sensitive to electromagnetic radiation (i.e., visible or non-visible light). The term "visible light" as used herein is defined as electromagnetic radiation having a wavelength from 380 nm to 750 nm. The term "non-visible light" as used herein is defined as electromagnetic radiation having a wavelength shorter than 380 nm (such as gamma rays, x-rays, ultraviolet) or longer than 750 nm (such as infrared, microwaves, radio waves). Examples of chromophoric functional groups include groups that can be or cause isomerization between a trans to a cis form; groups that can be or cause transition from a relatively non-polar hydrophobic, non-ionized state to a hydrophilic ionic state; and/or groups that are polymerized with other monomer or comonomer units in response to electromagnetic radiation. Example of chromophoric functional groups include azide-containing fluorescent dyes capable of being functionalized into the macroCTA polymer units through a CUAAC reaction, such as 3-azido-7-hydroxycoumarin, Azide BDP-FL, 5-FAM-Azide, 6-FAM-Azide, Picolyl-Azide-5/6-FAM, AF488-Azide, AF488-Picolyl-Azide, 10-PEG3-Azide, 5-SIMA-Azide, 5-TAMRA-Azide, 5/6-TAMRA-PEG3-Azide, Picolyl-Azide-5/6-TAMRA, Cy3-Azide, Sulfo-Cy3-Azide, Picolyl-Azide-Sulfo-Cy3, AF546-Azide, AF546-Picolyl-Azide, AF555-Azide, AF555-Picolyl-Azide, 5/6-Texas Red-PEG3-Azide, AF594-Azide, AF594-Picolyl-Azide, Cy5-Azide, Sulfo-Cy5-Azide, Picolyl-Azide-Sulfo-Cy5, AF647-Azide, AF647-Picolyl-Azide, Cy5.5-Azid, Picolyl-Azide-Cy5.5, Cy7-Azide, Picolyl-Azide-Cy7.

The $R^1$ group of a RAFT agent, the $R^1$ group of a macroCTA polymer, or the $R^1$ group(s) of a nanoworm can be pre-functionalized or post-functionalized. For example, $R^1$ groups of a nanoworm can be post-functionalized after formation of the nanoworm or can be pre-functionalized prior to the formation of the nanoworm by functionalizing the $R^1$ group of the RAFT agent or functionalizing the $R^1$ group of the macroCTA polymer. For example, $R^1$ groups of a macroCTA polymer can be post-functionalized after formation of the macroCTA polymer or can be pre-functionalized prior to the formation of the macroCTA polymer by functionalizing the $R^1$ group of the RAFT agent.

The $R^1$ group of the RAFT agent, macroCTA polymer, and/or nanoworm comprises or can be functionalized to comprise a carboxylic acid group, an alkyne, a pyridine, a dopamine, a thiolactone, a biotin, an azide, a peptide sequence, a nucleic acid sequence, a sugar sequence, a protease, a glycanase, a polymer, a chromophoric functional group, other functional groups, derivatives thereof, and/or combinations thereof. Specific examples of the $R^1$ group of the RAFT agent, macroCTA polymer, and/or nanoworm include, but are not limited to the following:

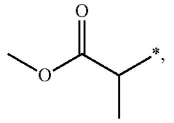

carboxylic acid

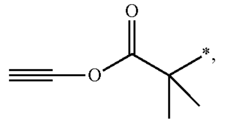

alkyne

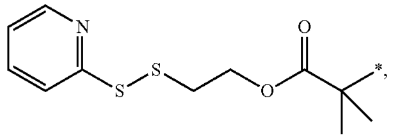

pyridine

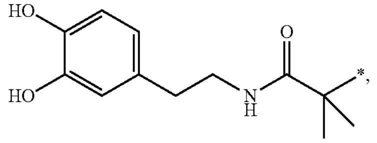

dopamine

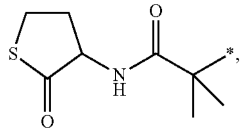

thiolactone

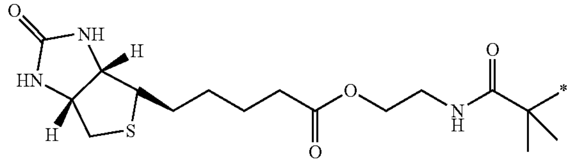

biotin $^{-}N{=}N^{+}{=}N{-}*$.

azide

The functional groups can be unsubstituted or substituted, unhalogenated or halogenated, and derivatives thereof.

In certain aspects, the $R^1$ group is functionalized to comprise a peptide sequence. A peptide sequence comprises one or more amino acids and/or one or more components of an amino acid. Examples of peptide sequences of amino acids includes, but are not limited to, GRGD (Gly-Arg-Gly-Asp), RGD (Arg-Gly-Asp), and other peptide sequences. Examples of peptide sequences of amino acids includes glycoproteins, such as vitronectin, fibronectin, and other glycoproteins. Examples of components of an amino acid includes guanidine, butylammonium, imidazolium, and other groups. In one example, a peptide sequence using a peptide azide can be coupled to a RAFT agent, a macroCTA polymer, or a nanoworm through a Cu(I)-catalyzed alkyne-azide (CuAAC) click reaction with a $R^1$ group comprising an alkyne functional group. In another example, a peptide sequence using a peptide alkyne can be coupled to a RAFT agent, a macroCTA polymer, or a nanoworm through a CuAAC click reaction with a $R^1$ group comprising an azide functional group.

In certain aspects, the $R^1$ group is functionalized to comprise a sugar sequence, such as through a CuAAC click reaction. A sugar sequence comprises one or more of a monosugar, polysugar, and/or combinations thereof. Examples of sugars include fucose, glucose, mannose, galactose, GalNac, GlcNAc, sialic acid, other glycans, other amino sugars, other acid sugars, derivatives thereof, isomers thereof, polysugars thereof, and/or combinations thereof. In certain aspects, while not being bound to any particular theory unless explicitly recited in the claims, it is believed that the functionalized sugar sequence $R^1$ group couples to a glycoprotein of an enveloped virus, interferes with glycosylation of an enveloped virus, interferes with attachment of an enveloped virus to a host cell, and/or interferes with entry of an enveloped virus to a host cell.

In certain aspects, the $R^1$ group is functionalized to comprise a protease (referring to any compound that breaks down a peptide or an amino acid), such as through a CuAAC click reaction. Examples of a protease include general peptide denaturants and specific peptide denaturants targeting asparagine, serine, threonine, or linkages thereof. In certain aspects, while not being bound to any particular theory unless explicitly recited in the claims, it is believed that the functionalized protease $R^1$ group couples to a glycoprotein of an enveloped virus, interferes with glycosylation of an enveloped virus, couples to a capsid of a non-enveloped virus, interferes with attachment of a virus (enveloped or non-enveloped) to a host cell, and/or interferes with entry of a virus (enveloped or non-enveloped) to a host cell.

In certain aspects, the $R^1$ group is functionalized to comprise a glycanase (referring to any compounds that breaks down glycans), such as through a CuAAC click reaction. Examples of a glycanase include general glycan denaturants and specific glycan denaturants targeting fucose, glucose, mannose, galactose, GalNac, GleNAc, sialic acid, or linkages thereof. In certain aspects, while not being bound to any particular theory unless explicitly recited in the claims, it is believed that the functionalized glycanase $R^1$ group couples to a glycoprotein of an enveloped virus, interferes with glycosylation of an enveloped virus, interferes with attachment of an enveloped virus to a host cell, and/or interferes with entry of an enveloped virus to a host cell.

FIG. 1 is a schematic view illustrating a nanoworm 100 according to certain aspects. A backbone or core 110 of the nanoworm 100 comprises the alkene units and the macroCTA polymer units. The nanoworm 100 includes $R^1$ groups 130 from the macroCTA polymer units. The $R^1$ group 130 is a component from a RAFT agent, which can be pre-functionalized or post-functionalized. The $R^1$ group 130 comprises any suitable $R^1$ group. The $R^1$ group can be selected to modify the capture and killing efficiency of the nanoworm 100 and/or to modify the responsiveness (e.g., temperature, pH, salinity concentration, light, and/or combinations thereof) of the nanoworm 100.

In certain aspects, two or more sets of macroCTA polymer units are used to form a nanoworm by further polymerizing the two or more sets of macroCTA polymers and alkene monomers. For example, a nanoworm can be produced by first producing macroCTA-A units with an $R^1$ group and producing macroCTA-B units with an $R^1$ group. The $R^1$ groups of the macroCTA-A units and the $R^1$ groups of the macroCTA-B units can be the same or different. The macroCTA-A units, the macroCTA-B units, and alkene monomers are polymerized together to form a nanoworm. The RAFT agent incorporated into the macroCTAs polymerizes the alkene units and the macroCTA polymer units to form a nanoworm of the general formula (VI):

$$(\text{Alkene Units})_m(\text{MacroCTA-A Units})_n(\text{MacroCTA-B Units})_o \quad \text{(VI)}$$

in which each of the MacroCTA-A includes unfunctionalized or functionalized $R^1$ group as a component of a RAFT agent and in which each of the MacroCTA-B includes a unfunctionalized or functionalized $R^1$ group as a component of a RAFT agent. The nanoworm includes the macroCTA-A units, the macroCTA-B units, the alkene units, and components of the RAFT agents. In certain aspects, m, n, and o are any independently selected positive integers. In certain aspects, m is an integer from 20 to 400, n is an integer from 1 to 200, and o is an n is an integer from 1 to 200. The alkene units, the MacroCTA-A units, and the MacroCTA-B units can be formed into the nanoworm in any sequence, such as in a random, alternating, statistical, periodic, or block sequence.

Figure 14:
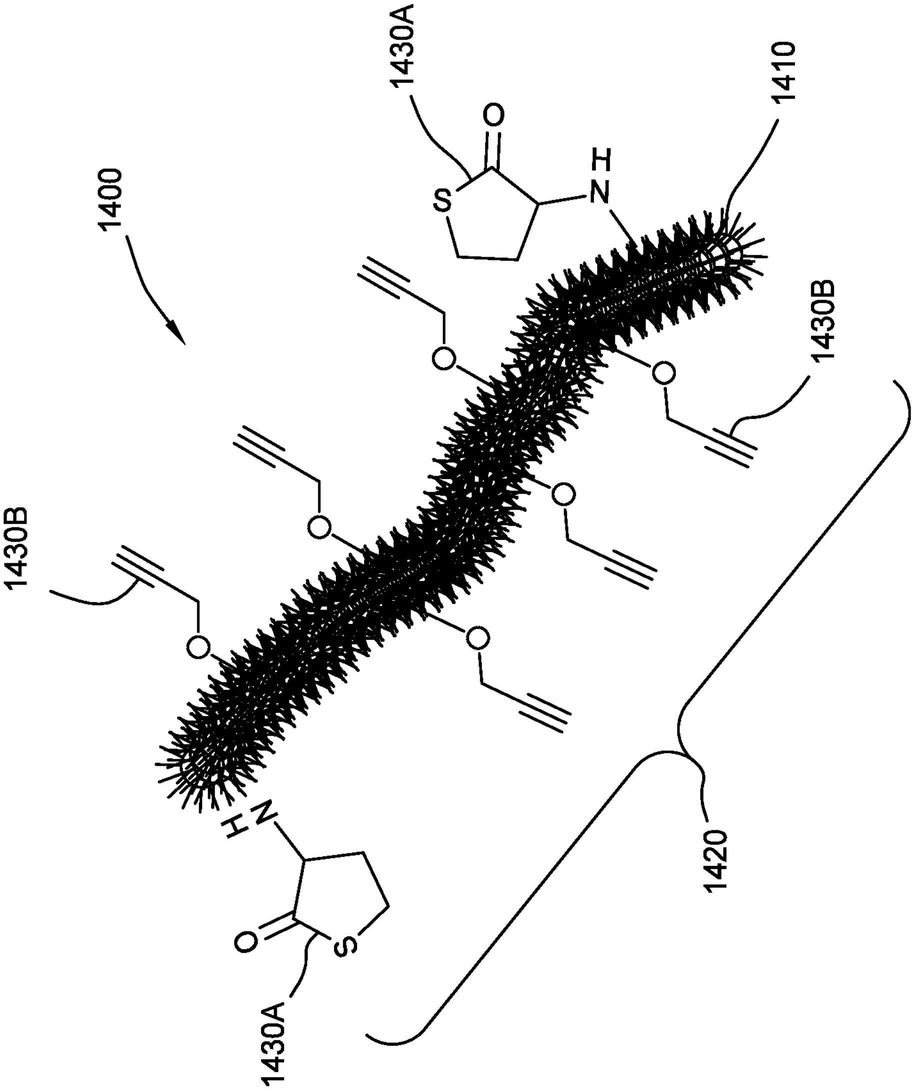
FIG. 14 is a schematic view illustrating a nanoworm with two different $R^1$ groups according to certain aspects.

FIG. 14 is a schematic view illustrating a nanoworm 1400 with two different $R^1$ groups according to certain aspects. A core 1410 of the nanoworm 100 comprises the alkene units and the macroCTA-A units, and the macroCTA-B units. The nanoworm 1400 includes a $R^1$ group 1430-A from the macroCTA-A units and includes a $R^1$ group 1430-B from the macroCTA-B units. The $R^1$ groups 1430A-B are each a component from a RAFT agent, which can be unfunctionalized or functionalized (i.e., pre-functionalized or post-functionalized). The $R^1$ groups 1430A-B comprises any suitable $R^1$ groups, such as an alkyne for $R^1$ group 1430A and such an B-thiolactone group for $R^1$ group 1430B (as shown in FIG. 14). The same or different $R^1$ groups of the macroCTA-A and of the macroCTA-B can be selected to modify the capture and killing efficiency of the nanoworm 100 and/or to modify the responsiveness (e.g., temperature, pH, salinity concentration, light, and/or combinations thereof) of the nanoworm 1400.

Figure 2A:
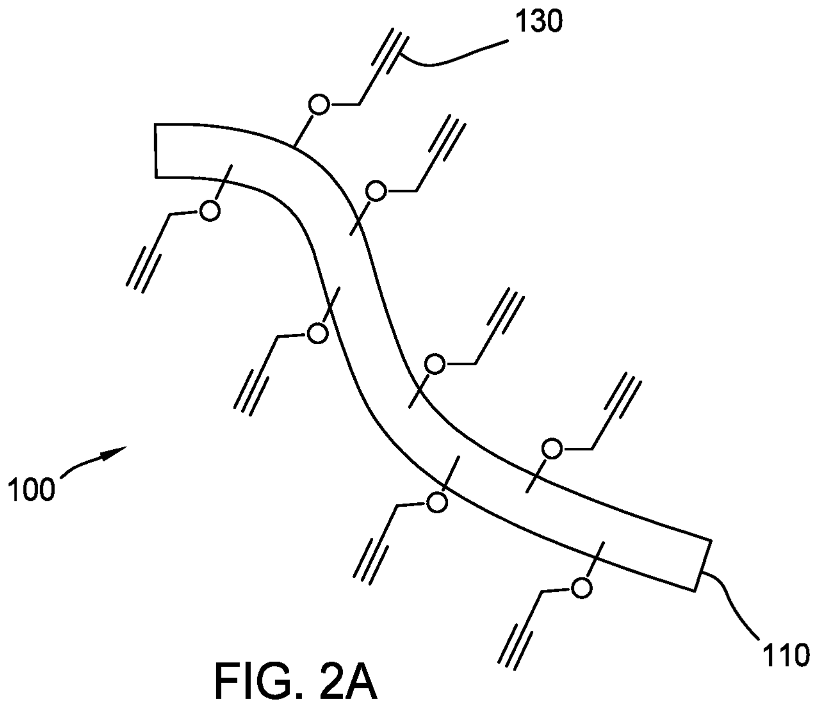
FIGS. 2A-2B are schematic views illustrating a nanoworm with an $R^1$ group further functionalized to include a macromolecule according to certain aspects.
Figure 2B:
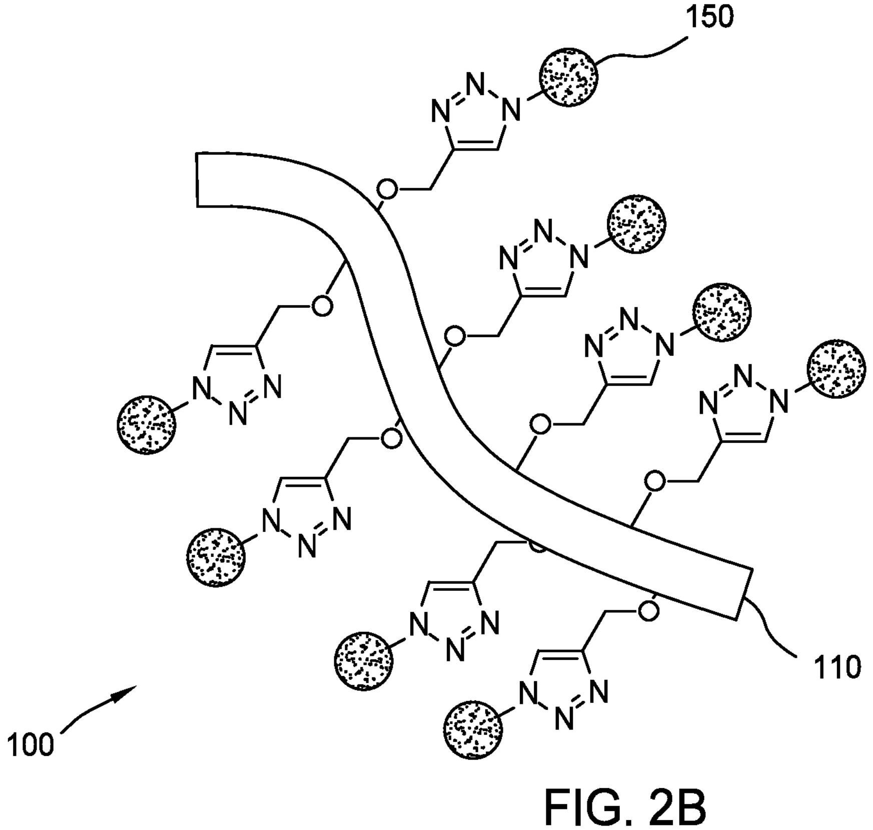

FIGS. 2A-2B are schematic views illustrating a nanoworm 100, such as the nanoworm 100 of FIG. 1, with an $R^1$ group 130 further functionalized to include a macromolecule 150 (as shown in FIG. 2B) according to certain aspects. FIGS. 2A-B use like numerals as FIG. 1 for ease of description. As shown in FIG. 2A, the nanoworm 100 includes a $R^1$ group 130 comprising an alkyne group. As shown in FIG. 2B, a macromolecule azide can react with the alkyne group of FIG. 2A through a Cu(I)-catalyzed alkyne-azide (CuAAC) click reaction to form a functionalized $R^1$ group 130 comprising a macromolecule 150 at the end of a macroCTA polymer unit. For example, the macromolecule azide comprises a peptide azide, a nucleic acid azide, a sugar azide, a protease azide, a glycanase azide, a polymer azide, or other macromolecule azide to respectively form a macromolecule 150 comprising a peptide sequence, a nucleic acid sequence, a sugar sequence, a protease, a glycanase, a grafted polymer, or other macromolecule. In other aspects, any macromolecule comprises or be coupled to the $R^1$ groups of the macroCTA polymer units by any reaction scheme, such as through a reaction of a macroCTA polymer units quaternized with azide groups reacting with macromolecule alkynes.

Figure 3:
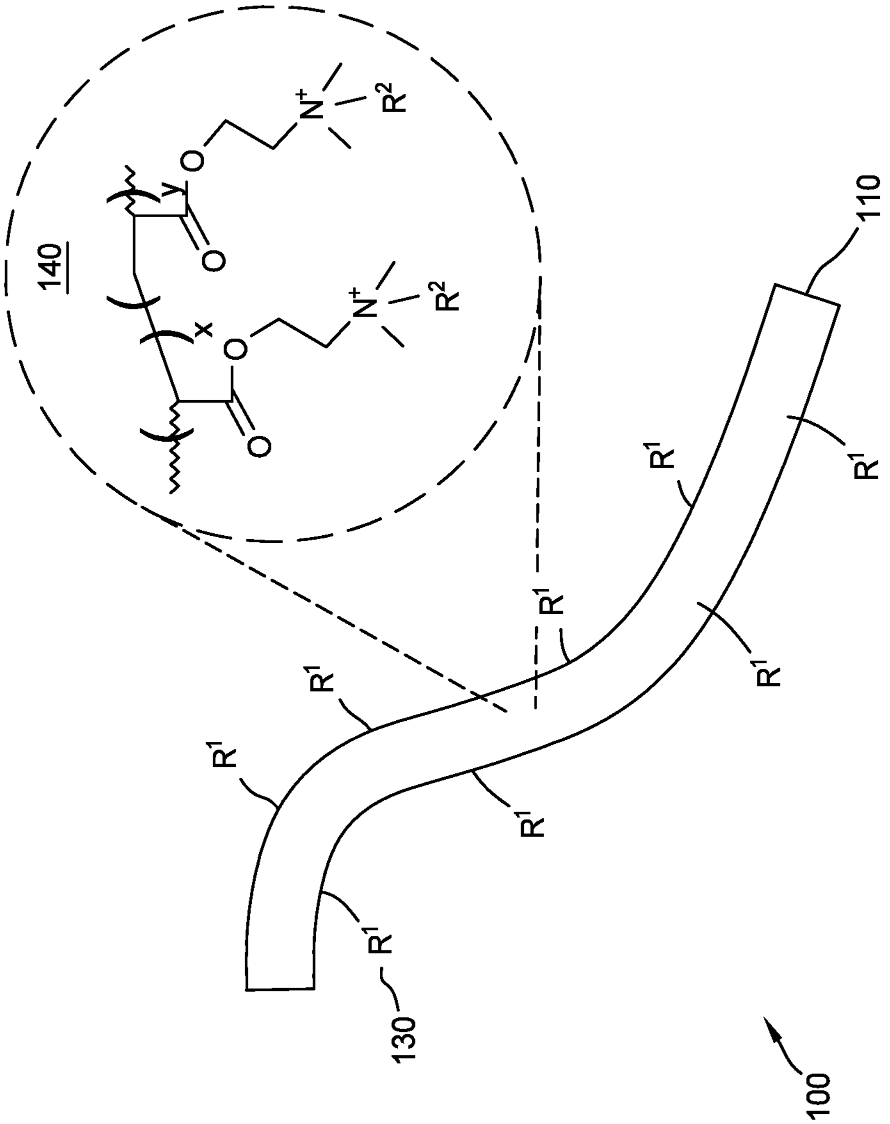
FIG. 3 is a schematic view illustrating a nanoworm with quaternized amine groups according to certain aspects.

FIG. 3 is a schematic view illustrating a nanoworm 100 with quaternized amine groups 140, such as the nanoworm 100 of FIG. 1, according to certain aspects. FIG. 3 uses like numerals as FIG. 1 for ease of description. One or more of the macroCTA polymer units have one or more tertiary amine groups. The tertiary amine group can be quaternized with any suitable $R^2$ group. The $R^2$ group of the quaternized amine croup comprises or can be functionalized to comprise an alkyl, a carboxylic acid, an alkyne, a pyridine, a dopamine, a thiolactone, a biotin, an azide, a peptide sequence, a nucleic acid sequence, a sugar sequence, a protease, a glycanase, a grafted polymer, a chromophoric functional group, other functional groups, derivatives thereof, and/or combinations thereof. For example, a macroCTA polymer unit can comprise two or more $R^2$ groups comprising or functionalized to comprises two or more of an alkyl, a carboxylic acid, an alkyne, a pyridine, a dopamine, a thiolactone, a biotin, an azide, a peptide sequence, a nucleic acid sequence, a sugar sequence, a protease, a glycanase, a grafted polymer, a chromophoric functional group, and other functional groups in order to modify the capture and killing efficiency of the nanoworm and/or to target general or specific microbes. The tertiary amine group can be quaternized by reaction with an $R^2$ halide or by other $R^2$ compounds. Specific examples of an $R^2$ group includes an alkyl moiety, an alkyne moiety, and/or combinations thereof.

In certain aspects, $R^2$ is an alkyl group of any suitable carbon length. An alkyl halide can quaternize a tertiary amine to form an alkyl moiety. A nanoworm with a macroCTA polymer unit having a plurality of tertiary amine groups can be quaternized with a certain ratio of different alkyl groups $R^2$. The ratio of quaternized short chain alkyl groups from one to four carbons to long chain alkyl groups of five or more carbons can be selected to adjust the properties of the nanoworm 100. For example, individual alkylamino groups of the monomers of the macroCTA polymer unit of a nanoworm 100 can be functionalized with a quaternized methyl group or with a quaternized octyl groups. For example, a nanoworm comprising a macroCTA polymer unit of poly(NIPAM-co-DMAEMA) can be quaternized to have z % long chain alkyl groups and (1-z %) short chain alkyl groups having the general structure (VII):

(VII)

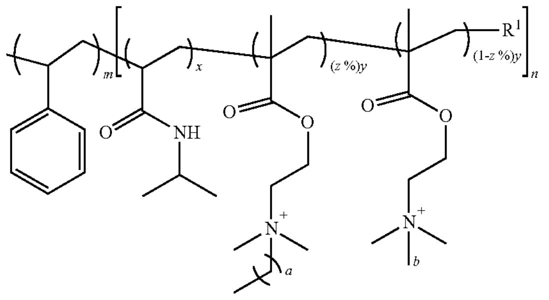

in which $R^1$ (including unfunctionalized or functionalized $R^1$ groups) are components of a RAFT agent. In certain aspects, a, b, x, y, m, and n are any independently selected positive integer and z is independently any number between 0% and 100%. In certain aspects, x is an integer from 10 to 100, y is an integer from 10 to 100, z is a number between 0% to 100%, m is an integer from 20 to 400, n is an integer from 1 to 200, a is an integer of 4 or more, and b is an integer from 1 to 4, in which the monomers of the macroCTA polymer unit are in any sequence and the styrene and the macroCTA polymers units are in any sequence.

The macroCTA polymer units can be quaternized with alkyl groups to modify the capture and killing efficiency of the macroCTA polymer units and/or to modify the responsiveness (e.g., temperature, pH, salinity concentration, light, and/or combinations thereof) of the macroCTA polymer units. In certain aspects, an increased ratio of short alkyl quaternized groups from 1 to 4 carbons to long alkyl quaternized groups of 5 or more carbons, such as from 5 to 20 carbons, increases a lower critical solution temperature (LCST) in water of the macroCTA polymer unit. While not being bound to any particular theory unless explicitly recited in the claims, it is believed that an alkyl group $R^2$ of 5 or more carbons, such as from 5 to 20 carbons, can provide cell membrane penetration of the alkyl moiety into the hydrophobic portion of a cell membrane (such as a viral cell envelope, a non-enveloped viral cell capsid, a bacterial cell membrane, or fungus cell membrane). While not being bound to any particular theory unless explicitly recited in the claims, it is believed that a quaternary ammonium cation can provide interactions with a cell membrane surface (such as the interactions of phosphate moieties of a phospholipid bilayer of a cell membrane surface). While not being bound to any particular theory unless explicitly recited in the claims, it is believed that the quaternary ammonium cation provides hydrophilicity to a macroCTA polymer unit so that the alkyl moieties of the alkylamino group do not become buried within the polyalkene.

In certain aspects, the $R^2$ group is functionalized to comprise a peptide sequence. A peptide sequence comprises one or more amino acids and/or one or more components of an amino acid. Examples of peptide sequences of amino acids includes, but are not limited to, GRGD (Gly-Arg-Gly-Asp), RGD (Arg-Gly-Asp), and other peptide sequences. Examples of peptide sequences of amino acids includes glycoproteins, such as vitronectin, fibronectin, and other glycoproteins. Examples of components of an amino acid includes guanidine, butvlammonium, imidazolium, and other groups. In one example, a peptide sequence using a peptide azide can be coupled to a quaternized amine group through a Cu(I)-catalyzed alkyne-azide (CuAAC) click reaction with a quaternized amine group comprising an alkyne functional group. In another example, a peptide sequence using a peptide alkyne can be coupled to a quaternized amine group through a CuAAC click reaction with a quaternized amine group comprising an azide functional group.

In certain aspects, the $R^2$ group is functionalized to comprise a sugar sequence, such as through a CuAAC click reaction. A sugar sequence comprises one or more of a monosugar, polysugar, and/or combinations thereof. Examples of sugars include fucose, glucose, mannose, galactose, GalNac, GlcNAc, sialic acid, other glycans, other amino sugars, other acid sugars, derivatives thereof, isomers thereof, polysugars thereof, and/or combinations thereof. In certain aspects, while not being bound to any particular theory unless explicitly recited in the claims, it is believed that the functionalized sugar sequence $R^2$ group couples to a glycoprotein of an enveloped virus, interferes with glycosylation of an enveloped virus, interferes with attachment of an enveloped virus to a host cell, and/or interferes with entry of an enveloped virus to a host cell.

In certain aspects, the $R^2$ group is functionalized to comprise a protease (referring to any compound that breaks down a peptide or an amino acid), such as through a CuAAC click reaction. Examples of a protease include general peptide denaturants and specific peptide denaturants targeting asparagine, serine, threonine, or linkages thereof. In certain aspects, while not being bound to any particular theory unless explicitly recited in the claims, it is believed that the functionalized protease $R^2$ group couples to a glycoprotein of an enveloped virus, interferes with glycosylation of an enveloped virus, couples to a capsid of a non-enveloped virus, interferes with attachment of a virus (enveloped or non-enveloped) to a host cell, and/or interferes with entry of a virus (enveloped or non-enveloped) to a host cell.

In certain aspects, the $R^2$ group is functionalized to comprise a glycanase (referring to any compounds that breaks down glycans), such as through a CuAAC click reaction. Examples of a glycanase include general glycan denaturants and specific glycan denaturants targeting fucose, glucose, mannose, galactose, GalNac, GlcNAc, sialic acid, or linkages thereof. In certain aspects, while not being bound to any particular theory unless explicitly recited in the claims, it is believed that the functionalized glycanase $R^2$ group couples to a glycoprotein of an enveloped virus, interferes with glycosylation of an enveloped virus, interferes with attachment of an enveloped virus to a host cell, and/or interferes with entry of an enveloped virus to a host cell.

Figure 4A:
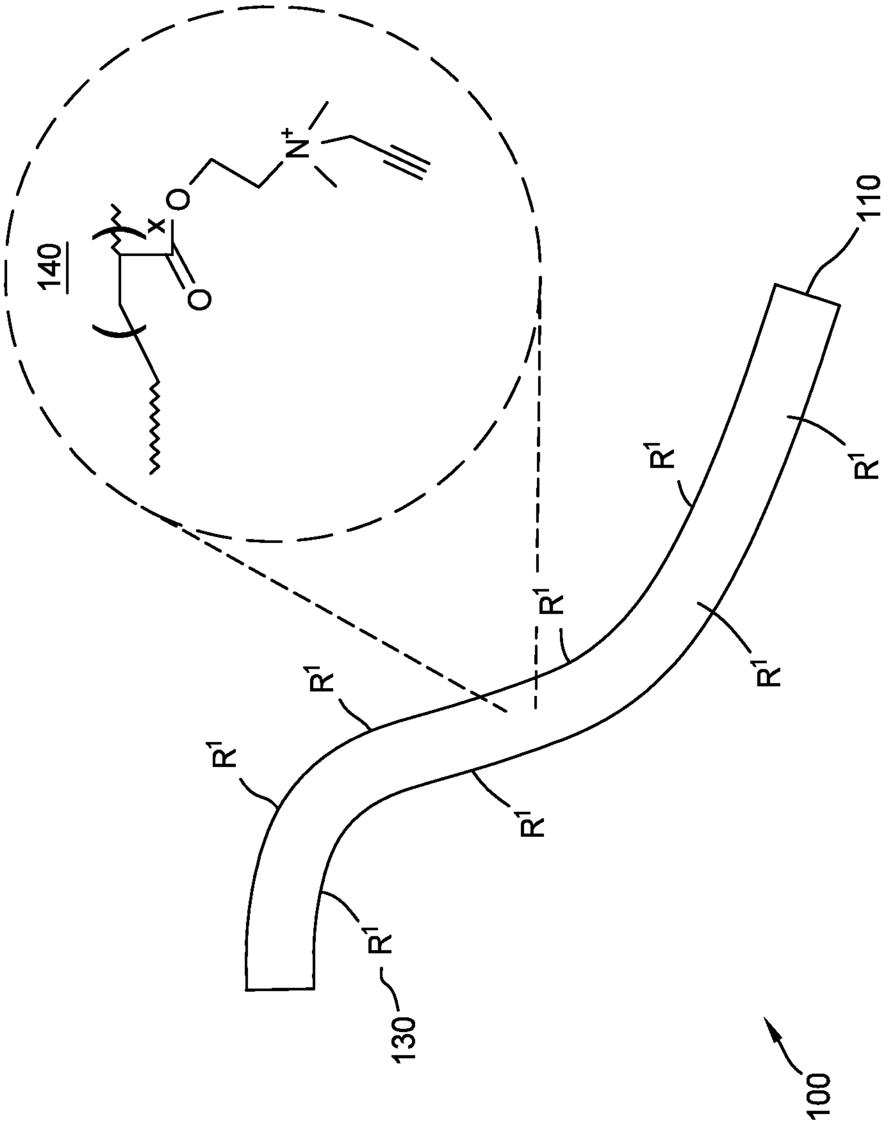
FIGS. 4A-4B are schematic views illustrating a nanoworm with quaternized amine groups further functionalized to include a macromolecule according to certain aspects.
Figure 4B:
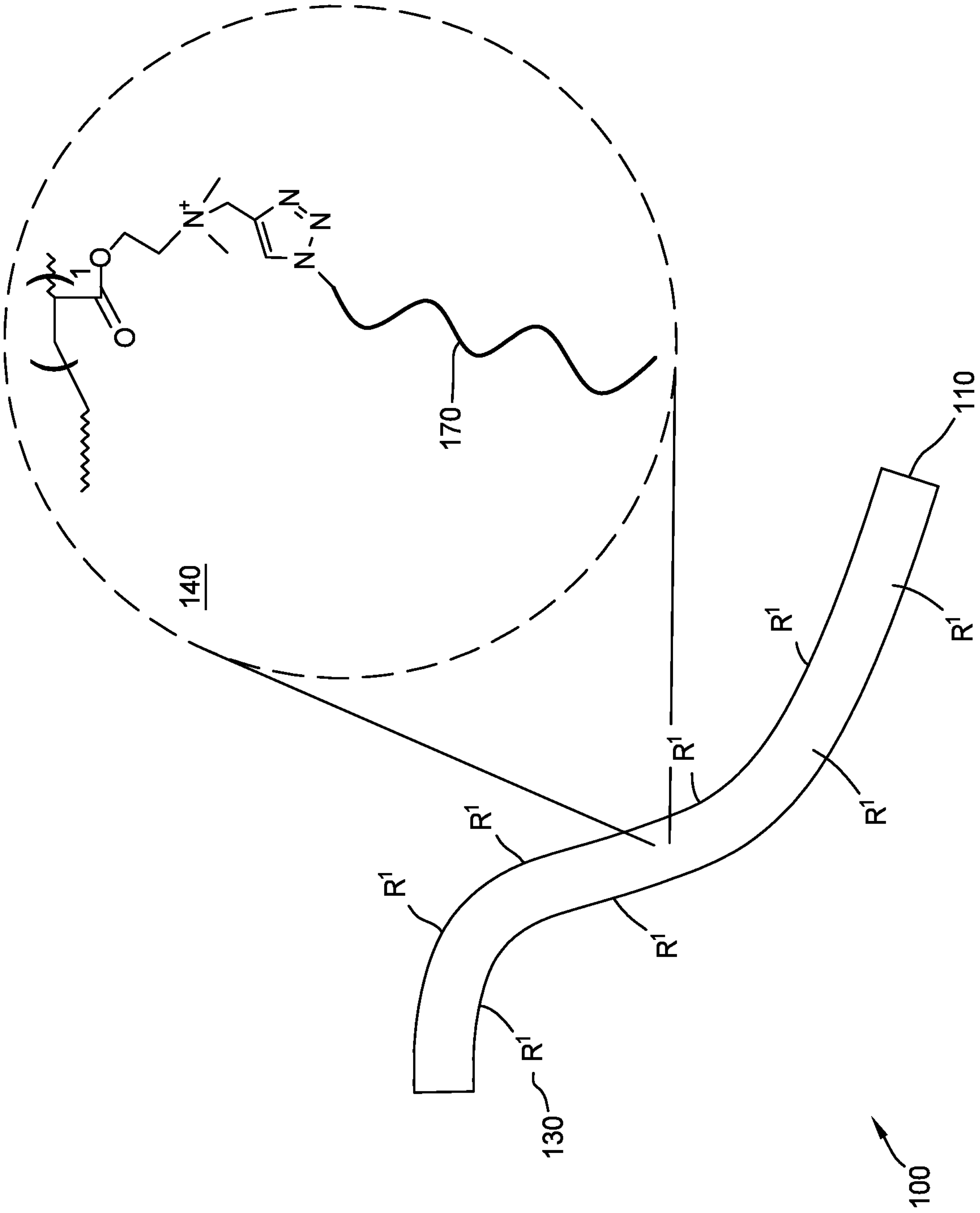

FIG. 4A shows a nanoworm 100 with macroCTA polymers with quaternized amine groups 140 including an alkyne moiety according to certain aspects. As shown in FIG. 4B, a macromolecule azide can react with the alkyne moiety of FIG. 4A through a CuAAC click reaction to form a macromolecule 170 coupled to the macroCTA polymer of the core 110 according to certain aspects. For example, the macromolecule azide comprises a peptide azide, a nucleic acid azide, a sugar azide, a protease azide, a glycanase azide, a polymer azide, or other macromolecule azide to respectively form a macromolecule 170 comprising a peptide sequence, a nucleic acid sequence, a sugar sequence, a protease, a glycanase, a grafted polymer, or other macromolecule. In other aspects, any macromolecule can be coupled to the quaternized amine groups 140 of the macroCTA polymer units by any reaction scheme, such as through a reaction of a macroCTA polymer units quaternized with azide groups reacting with macromolecule alkynes.

The macromolecules 150 (as shown in FIG. 2B) and/or the macromolecules 170 (as shown in FIG. 4B) can independently comprise a grafted polymer with one or more properties including, but not limited to, temperature-responsive (LCST, UCST, or both) polymers, pH-responsive polymers, light-responsive polymers, saline-responsive polymers, and/or combinations thereof. The grafted polymer comprises a polymer from by any suitable polymerization method, such as addition polymerization (including anionic and cationic polymerization), chain polymerization, free radical or living radical polymerization (including atom transfer radical polymerization or ATRP), metal catalyzed polymerization, nitroxide polymerization, degenerative chain transfer polymerization, RAFT, single-electron transfer living radical polymerization or SET-LRP, condensation polymerization, and/or combinations thereof.

The grafted polymers of macromolecules 150 (as shown in FIG. 2B) and/or the macromolecules 170 (as shown in FIG. 4B) be can be further functionalized. The grafted polymers can comprise or be functionalized to comprise an alkyl, a carboxylic acid, an alkyne, a pyridine, a dopamine, a thiolactone, a biotin, an azide, a peptide sequence, a nucleic acid sequence, a sugar sequence, a protease, a glycanase, a chromophoric functional group, other functional groups, derivatives thereof, and/or combinations thereof. For example, the grafted polymer can include tertiary amine groups which are quaternized to be functionalized. The quaternized amine groups of the grafted polymer can be further functionalized to include a peptide sequence, a nucleic acid sequence, a sugar sequence, a protease, a glycanase, and/or combinations thereof. The grafted polymer can comprises two or more of an alkyl, a carboxylic acid, an alkyne, a pyridine, a dopamine, a thiolactone, a biotin, an azide, a peptide sequence, a nucleic acid sequence, a sugar sequence, a protease, a glycanase, a chromophoric functional group, and other functional groups in order to modify the capture and killing efficiency of the nanoworm and/or to target general or specific microbes.

The tertiary amine groups of the grafted polymers can be quaternized with alkyl groups to modify the capture and killing efficiency of the grafted polymers and/or to modify the responsiveness (e.g., temperature, pH, salinity concentration, light, and/or combinations thereof) of the grafted polymers. In certain aspects, an increased ratio of short alkyl quaternized groups from 1 to 4 carbons to long alkyl quaternized groups of 5 or more carbons, such as from 5 to 20 carbons, increases a lower critical solution temperature (LCST) in water of the grafted polymer. While not being bound to any particular theory unless explicitly recited in the claims, it is believed that an alkyl group $R^2$ of 5 or more carbons, such as from 5 to 20 carbons, can provide cell membrane penetration of the alkyl moiety into the hydrophobic portion of a cell membrane (such as a viral cell envelope, a non-enveloped viral cell capsid, a bacterial cell membrane, or fungus cell membrane), While not being bound to any particular theory unless explicitly recited in the claims, it is believed that a quaternary ammonium cation can provide interactions with a cell membrane surface (such as the interactions of phosphate moieties of a phospholipid bilayer of a cell membrane surface). While not being bound to any particular theory unless explicitly recited in the claims, it is believed that the quaternary ammonium cation provides hydrophilicity to a grafted polymer so that the alkyl moieties of the alkylamino group do not become buried within the nanoworm core.

In certain aspects, a quaternized amine group of the grafted polymer is functionalized to comprise a peptide sequence. A peptide sequence comprises one or more amino acids and/or one or more components of an amino acid. Examples of peptide sequences of amino acids includes, but are not limited to, GRGD (Gly-Arg-Gly-Asp), RGD (Arg-Gly-Asp), and other peptide sequences. Examples of peptide sequences of amino acids includes glycoproteins, such as vitronectin, fibronectin, and other glycoproteins. Examples of components of an amino acid includes guanidine, butylammonium, imidazolium, and other groups. In one example, a peptide sequence using a peptide azide can be coupled to a quaternized amine group through a Cu(I)-catalyzed alkyne-azide (CuAAC) click reaction with a quaternized amine group comprising an alkyne functional group. In another example, a peptide sequence using a peptide alkyne can be coupled to a quaternized amine group through a CuAAC click reaction with a quaternized amine group comprising an azide functional group.

In certain aspects, a quaternized amine group of the grafted polymer is functionalized to comprise a sugar sequence, such as through a CuAAC click reaction. A sugar sequence comprises one or more of a monosugar, polysugar, and/or combinations thereof. Examples of sugars include fucose, glucose, mannose, galactose, GalNac, GlcNAc, sialic acid, other glycans, other amino sugars, other acid sugars, derivatives thereof, isomers thereof, polysugars thereof, and/or combinations thereof. In certain aspects, while not being bound to any particular theory unless explicitly recited in the claims, it is believed that the functionalized sugar sequence $R^2$ group couples to a glycoprotein of an enveloped virus, interferes with glycosylation of an enveloped virus, interferes with attachment of an enveloped virus to a host cell, and/or interferes with entry of an enveloped virus to a host cell.

In certain aspects, a quaternized amine group of the grafted polymer is functionalized to comprise a protease (referring to any compound that breaks down a peptide or an amino acid), such as through a CuAAC click reaction. Examples of a protease include general peptide denaturants and specific peptide denaturants targeting asparagine, serine, threonine, or linkages thereof. In certain aspects, while not being bound to any particular theory unless explicitly recited in the claims, it is believed that the functionalized protease group couples to a glycoprotein of an enveloped virus, interferes with glycosylation of an enveloped virus, couples to a capsid of a non-enveloped virus, interferes with attachment of a virus (enveloped or non-enveloped) to a host cell, and/or interferes with entry of a virus (enveloped or non-enveloped) to a host cell.

In certain aspects, a quaternized amine group of the grafted polymer is functionalized to comprise a glycanase (referring to any compounds that breaks down glycans), such as through a CuAAC click reaction. Examples of a glycanase include general glycan denaturants and specific glycan denaturants targeting fucose, glucose, mannose, galactose, GalNac, GlcNAc, sialic acid, or linkages thereof. In certain aspects, while not being bound to any particular theory unless explicitly recited in the claims, it is believed that the functionalized glycanase group couples to a glycoprotein of an enveloped virus, interferes with glycosylation of an enveloped virus, interferes with attachment of an enveloped virus to a host cell, and/or interferes with entry of an enveloped virus to a host cell.

In certain aspects, a nanoworm comprising one or more sets of MacoCTA polymer units and one or more grafted polymers has the general formula (VIII)

$$(\text{Alkene Units})_m(\text{MacroCTA Units})_n(\text{Grafted Polymer})_o \quad \text{(VIII)}$$

in which each of the MacroCTA includes an unfunctional zed or functionalized $R^1$. In one aspect, the grafted polymer can be grafted to the $R^1$ group of the MacroCTA. In another aspect, the grafted polymer is grafted to quaternary amine groups of the macroCTA polymer units. In still another aspect, the grafted polymer is grafted both to the $R^1$ group of the MacroCTA and to quaternary amine groups of the macroCTA polymer units. In certain aspects, m, n, and o are any independently selected positive integers. In certain aspects, m is an integer from 20 to 400, n is an integer from 1 to 200, and o is an integer from 1 to 10,000.

In certain aspects of the nanoworms described herein, such as the nanoworms of general formula (IV)-(VII), the Z group of the macroCTA polymer units as a component of a RAFT agent may remain or may be cleaved off. In certain aspects, a nanoworm including a Z group of the macroCTA polymer as a component of a RAFT agent may be further polymerized and/or cross-linked with another nanoworm(s).

A nanoworm of FIGS. 1-21 can have anti-microbial properties, such as capturing, killing, inactivating, disassembly, degenerating, disinfecting, sanitizing, and/or removal of microbes, by selection of macroCTA polymer units, of quaternization of tertiary amine groups of the macroCTA polymer units, of a $R^1$ group of the macroCTA polymer units, of a $R^2$ group of quaternization of tertiary amine groups of the macroCTA polymers, of functionalization of the $R^1$ group to include a macromolecule, of functionalization of the $R^2$ group to include a macromolecule, of a grafted polymer incorporated into the nanoworm, of functionalization of a grafted polymer incorporated into the nanoworm, and/or of combinations thereof. Such, selection can impact the responsiveness of the nanoworm to temperature, pH, salinity concentration, and/or light.

Viral killing or inhibitor peptides or peptide mimics coupled to a nanoworm as a $R^1$ group of a macroCTA, as a $R^2$ group of a macroCTA, and/or to a grafted polymer include, but are not limited to the peptides of TABLES 1-3. TABLE 1 includes peptides inhibiting virus attachment and virus-cell membrane fusion. TABLE 2 includes peptides disrupting viral envelopes. TABLE 3 includes peptides inhibiting viral replication. The peptides can target certain viruses or a broad spectrum of viruses. Other suitable peptide or peptide mimics can also be coupled to a nanoworm to provide antimicrobial properties.

TABLE 1

The Peptides inhibiting Virus Attachment and Virus-Cell Membrane Fusion

| Peptide | Influenza Serotype | Sequence | SEQ. ID No. |
|---|---|---|---|
| EB peptide | Broad spectrum | RRKKAAVALLPAVLLALLAP | 1 |
| Derived EB peptide | Broad spectrum | RRKKLAVLLALLA | 2 |
| P1 | H9N2 | NDFRSKT | 3 |
| P1 cyclic | H9N3 | CNDFRSKTC | 4 |
| FluPep 1 | H1N1 | WLVFFVIFYFFR | 5 |
| FluPep2 | H1N1 | WLVFFVIAYFAR | 6 |
| FiuPep 3 | H1N1 | WLVFFVIFYFFRRRKK | 7 |
| FluPep 4 | H1N1 | RRKKWLVFFVIFYFFR | 8 |
| FluPep 7 | H1N1 | RRKKIFYFFR | 9 |
| FluPep 8 | H1N1 | WLVFFVRRKK | 10 |
| FluPep 9 | H1N1 | FFVIFYRRKK | 11 |
| C18-s2 | H1N1, H3N2 | C17H35CO-ARLPRTMVHPKPAQP-NH2 | 12 |
| Pal L1 | H5N1 | C16-ARLPRTMVHPKPAQP | 13 |
| Pal M1 | H5N1 | C16-ARLPRTMV | 14 |
| Pal S1 | H5N1 | C16-ARLPR | 15 |
| Flufirvitide | Broad spectrum | — | |
| PEP 19-2.5 | H7N7, H3N2, H1N1 | GCKKYRRFRWKFKGKFWFWG | 16 |
| PEP 19-4 | H7N7, H3N2, H1N1 | GKKYRRFRWKFKGKWFWFG | 17 |
| PEP 19-8D | H7N7, H3N2, H1N1 | GFWFKGKWRFKKYRGGRYKKFRWK-<br>GKFWFG | 18 |
| PEP 19-CP | H7N7, H3N2, H1N1 | SSNKSTTGSGETTTA | 19 |
| Defensins | H1N1, H3N2 | ACYCRIPACIAGERRYGTCIYQGRLWAFCC | 20 |

TABLE 2

The Peptides Disrupting Viral Envelope

| Peptide | Influenza Serotype | Sequence | SEQ. ID. No. |
|---|---|---|---|
| LF C-lobe peptide | 1 H1H1, H3N2 | SKHSSLDCVLRP | 21 |
| LF C-lobe peptide | 2 H1H1, H3N2 | AGDDQGLDKCVPNSKEK | 22 |
| LF C-lobe peptide | 3 H1H1, H3N2 | NGESSADWAKN | 23 |
| Mucroporin-M1 | H5N1, H1N1 | LFRLIKSLIKRLVSAFK | 24 |
| LL-37 | H1N1, H3N2 | LLGDFFRKSKEKIGKEFKRIVQ-<br>RIKDFLRNLVPRTES | 25 |

TABLE 3

| The Peptides Inhibiting Viral Replication | | | |
|---|---|---|---|
| Peptide | Influenza Serotype | Sequence | SEQ. ID No. |
| PB1125 | Broad spectrum | MDVNPTLLFLKVPAQNAISTTFPYT | 26 |
| PB2137 | H1N1, H5N1 | MERIKELRDLMSWSRTREILTKTTV-DHMAIIKKYTSG | 27 |
| PB1731757 | H5N1 | ESGRIKKEEFAEIMKICSTIEELGRQK | 28 |
| PB1125AT6Y | H1N1,H5N1 | MDVNPYLLFLKVPAQ | 29 |
| Killer peptide | H7N1 | AKVTMTCSAS | 30 |
| HNP-1 | H3N2 | CYCRIPACIAGERRYGTCIYQGRLWAFCC | 31 |
| Peptid 6 | H1N1, H3N2 | CATCEQIADSQHRSHRQMV | 32 |

Figure 5:
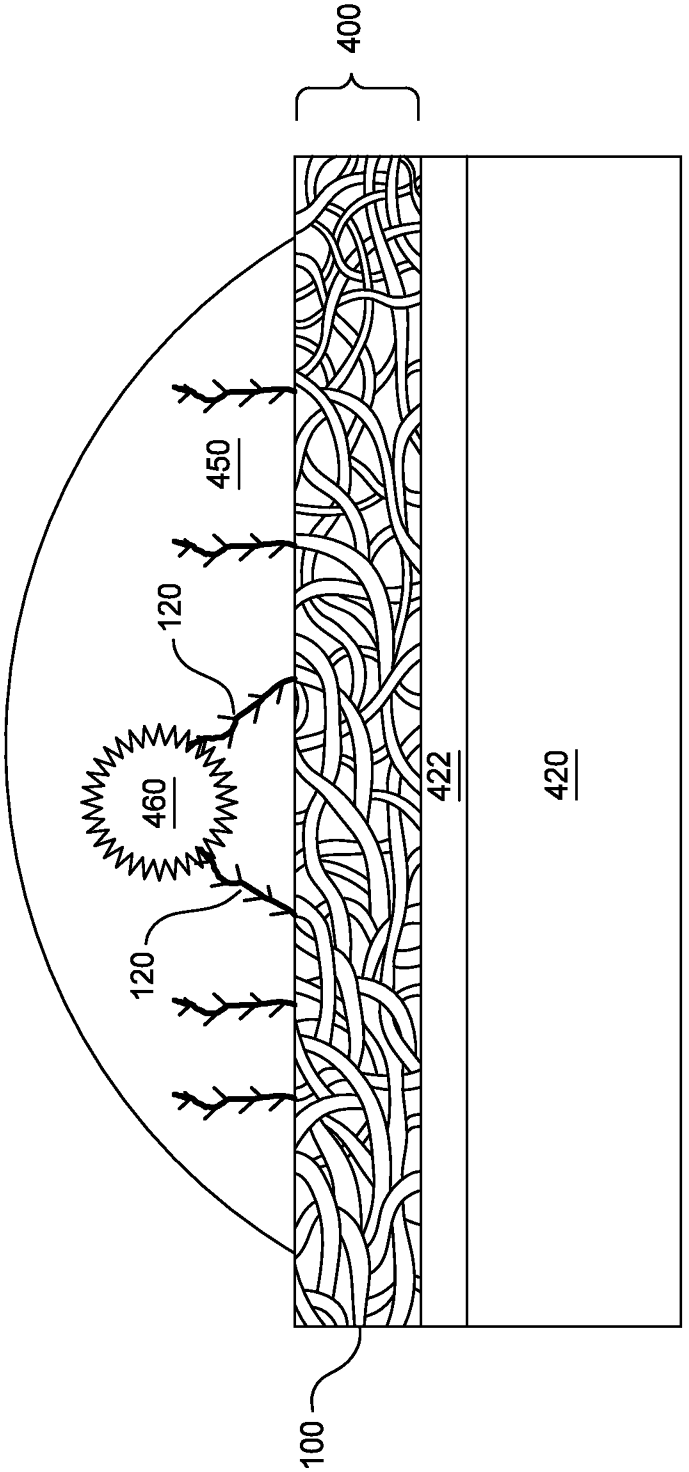
FIG. 5 is a schematic cross-sectional view of a coating comprising a plurality of nanoworms over a substrate according to certain aspects.

FIG. 5 is a schematic cross-sectional view of a coating 400 comprising a plurality of nanoworms 100 over a substrate 420, such as one or more of the nanoworms of FIGS. 1-4 or FIGS. 6-21, according to certain aspects. An adhesion promoter 422 may optionally be used to increase the adhesion of the coating 400 over the substrate 420. The nanoworms 100 may be deposited over the substrate 420 by spraying, brushing, rolling, or by other suitable deposition methods. The coating 400 provides antimicrobial properties to the substrate 420. The substrate 420 comprises polymers, metals, fabrics, glass, stone, ceramic, paper, other materials, and/or combinations thereof. The nanoworms 100 can be deposited as a dry powder. The nanoworms 100 can be deposited as a solution, such as diluted in water, organic solvents, inorganic solvents, and combinations thereof. The nanoworms 100 stored as a dry powder or as a solution diluted in water poses a low or no explosion risk.

The coating 400 comprises a plurality of the same nanoworms 100 or a plurality of different nanoworms 100. A portion or all of a macroCTA polymer unit 120 of the nanoworms can be exposed at the top surface of the coating 400. The macroCTA polymer units 120 exposed at the top surface of the coating 400 can be the same or different and can be from a plurality of the same nanoworms or from a plurality of different nanoworms 100. The macroCTA polymer units 120 exposed at the top surface of the coating 400 can be individually hydrophobic or hydrophilic or individually miscible or immiscible with a droplet depending on a responsive nature of an individual macroCTA polymer unit 120 independent from the properties of a polyalkene of the nanoworm. For example, one or more of macroCTA polymer units 120 can individually comprise a LCST polymer, which is a class of water-soluble thermoresponsive polymer miscible with a droplet below the LCST of the macroCTA polymer units 120. Above the LCST, the macroCTA polymer unit 120 is immiscible in part or in whole with the droplet. In other words, the macroCTA polymer unit 120 is hydrophilic below its LCST and is hydrophobic above its LCST.

As shown in FIG. 5, a droplet 450, at the surface of the coating 400, can be miscible with individual macroCTA polymer units 120 at a temperature below the LCST of the individual macroCTA polymer unit 120. The individual macroCTA polymer unit 120 miscible with the droplet 450 can bind to or interact with a microbe 460 suspended within or on the droplet 450 to provide antimicrobial properties to the substrate 420. The coating 400 can provide rapid or immediate antimicrobial properties to microbes suspended within or on the droplet 450 without having to wait for the droplet 450 to evaporate. The coating 400 does not require long evaporation times of the droplet to be effective in capturing or killing of and in preventing transmission of microbes suspended in or on the droplet. In comparison, antibacterial hydrophobic coatings require long evaporation times of a droplet to be effective. For example, an aqueous droplet having an initial diameter of 3 mm with an initial temperature of 20° C. takes approximately 111 minutes to completely evaporate in a surrounding air temperature of 24.8° C.

In certain aspects, a macroCTA polymer unit 120 can transition between being miscible and being immiscible in part or in whole with the mucosal drop. For example, a macroCTA polymer unit 120 can transition from below its LCST to above its LCST or from above its LCST to below its LCST. Such transitions can be from a change in temperature, a change in pH, a change in saline concentration, other parameters, and/or combinations thereof. The transition of a macroCTA polymer unit 120 between LCST conditions can impart compression, tension, or other mechanical forces upon a microbe to provide antimicrobial properties.

The coating 400 can be transparent, semi-transparent, or can be opaque. The transparency of the coating can be determined by the packing density of nanoworms 100 making up the coating 400 and the selection of the polyalkene of the core 110 of the nanoworms 100. For example, a transparent coating permits at least about 80% light transmission at one or more wavelengths from 380 nm to 740 nm, such as at least about 85%, at least about 90%, at least about 95%, or at least about 99% light transmission. Light transmission is determined by ASTM D 1003-00 (Total Transmittance) in which the T1 reading is of a clear glass slide and the T2 reading is of a nanoworm coating over the clear glass slide. For example, a semi-transparent coating permits from about 30% to about 80% light transmission at one or more wavelengths from 380 nm to 740 nm. For example, an opaque coating permits less than 30% light transmission at one or more wavelengths from 380 nm to 740 nm. The opacity of the coating 400 can be determined by the packing density of nanoworms 100 making up the coating 400, the selection of the polyalkene of the core 110 of the nanoworms 100, and the addition of dyes and other additives.

The coating 400 can be breathable by controlling the packing density of nanoworms 100 making up the coating. The coating 400 can be breathable by perforating, by embossing, by stretching, and/or by calendaring the coating 400 to form micro-pores. For example, the micro-pores can be in a size from about 0.1 microns to about 10 microns.

Figure 6:
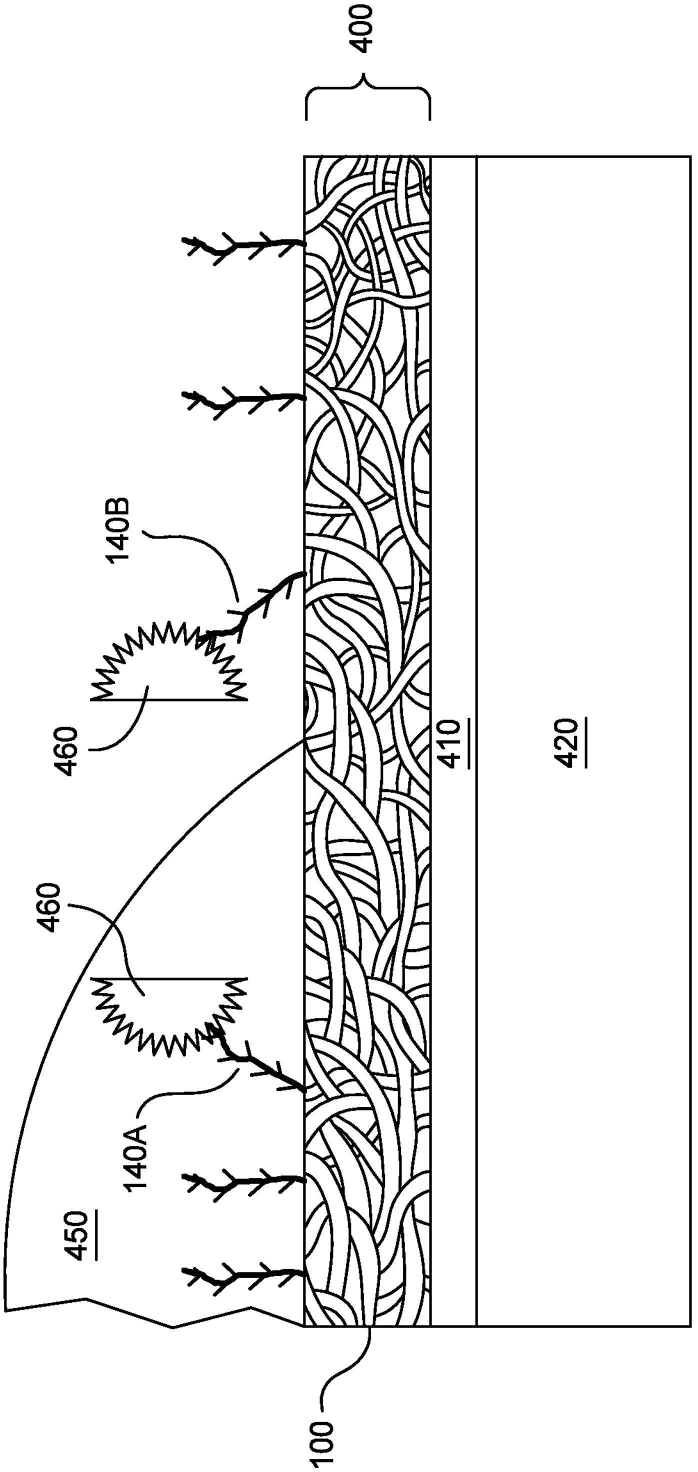
FIG. 6 is a schematic cross-sectional view of a coating comprising a plurality of nanoworms over a substrate with a first set of macroCTA polymer units and a second set of macroCTA polymer units having different LCSTs according to certain aspects.

FIG. 6 is a schematic cross-sectional view of a coating 400 comprising a plurality of nanoworms 100 over a substrate 420 with a first set of macroCTA polymer units 120A and a second set of macroCTA polymer units 120B in which the first set of macroCTA polymer units 120A and the second set of macroCTA polymer units 120B have different LCSTs according to certain aspects. For example, a macroCTA polymer unit 120A from the first set and a macroCTA polymer units 120B from the second set can both bind to a microbe while both macroCTA polymer units 120A, 120B are below their LCSTs and miscible with a mucosal drop 450. Then, as shown in FIG. 6, macroCTA polymer unit 120B transitioned into immiscible in part or in whole with the droplet 450. The microbe 460 can be disassembled by being coupled to the macroCTA polymer unit 120A miscible with the mucosal drop 450 and coupled the macroCTA polymer unit 120B immiscible in part or in whole with the droplet.

A coating 400 comprising a plurality of nanoworms as described in FIGS. 1-21 can be applied to any object. For example, a coating 400 comprising a plurality of nanoworms 100 can be applied over a substrate 420 in an aircraft (e.g., airplanes and helicopters) to provide anti-microbial properties to a surface of the aircraft. The substrate 420 can be a tray table, a headrest, a seatback pocket, a seatback top, a seat armrest, a seat, a bathroom door lock, a sink, a toilet, an in-flight magazine, a safety card, an overhead air vent, a seatbelt buckle, a window shade, a widow, an entertainment screen, an interior wall, a floor, a pillow, a blanket, and other surfaces of an aircraft. A coating 400 comprising a plurality of nanoworms 100 can be applied over a substrate 420 in a hospital to provide antimicrobial properties to a surface of the hospital. The substrate 420 can be a bed, a chair, a table, a counter, an interior wall, a floor, a door handle, a bathroom surface, and other surfaces of a hospital. A coating 400 comprising a plurality of nanoworms 100 can be applied over a substrate 420, such as implemented to relevant exemplary substrates as described herein, in a transportation vehicle, such as in aircrafts, spacecrafts, buses, trains, subway cars, taxis, cars, ferries, boats, cruise ships, ride attractions, and other transportation vehicles, to provide antimicrobial properties to a surface of the public transportation vehicle. The substrate 420 can be a seat, a handrail, a door, other analogous objects described herein, and other surfaces of a transportation vehicle. A coating 400 comprising a plurality of nanoworms 100 can be applied over a substrate 420 in surfaces of a building, such as an office building, a school building, a store building, a restaurant building, a college building, a daycare building, other buildings, to provide antimicrobial properties to a surface of the building. The substrate 420 can be a desk, a chair, a table, a bathroom, a floor, an interior wall, and other surfaces of a building. A coating 400 comprising a plurality of nanoworms 100 can be applied over a substrate 420 in a walkway or a people mover to provide antimicrobial properties to the walkway or the people mover. The substrate 420 can be stairs, an escalator, an elevator, a moving walkway, handrails of the walkway, control buttons of the elevator, and other walkway or people mover surfaces. A coating 400 comprising a plurality of nanoworms 100 can be applied to a substrate 420 for food packaging to provide antimicrobial properties to the food packaging. The coating 400 of the food packaging can be at least partially transparent so that a consumer can see the contents of the food packaging. A partially transparent coating permits at least 30% light transmission of one or more wavelengths from 380 nm to 740 nm. Light transmission is determined by ASTM D 1003-00 (Total Transmittance) in which the T1 reading is of a clear glass slide and the T2 reading is of a nanoworm coating over the clear glass slide. The coating 400 of the food packaging can be breathable to preserve the quality of the packaged food, A coating 400 comprising a plurality of nanoworms 100 can be applied to a substrate 420 of an electronic device. For example, the electronic device can be a mobile device, headphones, a keyboard, a mouse, a touchscreen, a computer, or other electronic devices. A coating 400 comprising a plurality of nanoworms 100 can be applied to a substrate 420 for wearables, such a substrate comprising natural, synthetic, composite fibers and fabrics, to provide antimicrobial properties to the wearables. Such wearables can be face masks, face shields, gloves, surgical gowns, hospital gowns, infant clothing, toddler clothing, or any wearable in which antimicrobial properties are desired. A coating 400 comprising a plurality of nanoworms 100 can be applied to a substrate 420 of a medical. For example, the medical devices include eye lens, stents (e.g., coronary stents), artificial joints (e.g., knees), screws, pins, plates, rods, intra-uterine devices, artificial discs, implants (e.g., breast), prosthetics, heart pacemakers, artificial hips, cardioverter defibrillators, and other medical devices. A coating 400 comprising a plurality of nanoworms 100 can be applied to a substrate 420 for a filter of any fluid. For example, the filter can filter air, blood, water, or other fluids to remove or to kill microbes.

The nanoworm coated surface can provide antimicrobial activity to any amount of aqueous solution. For example, the nanoworm coated surface can remove or kill microbes from blood in vivo and/or in vitro. For example, the nanoworm coated surface can be used to filter donated blood in vitro to remove diseases, such as coronavirus, HIV, hepatitis, syphilis, and other infections. For example, the nanoworm coated surface can be used to treat human patients by in vivo recirculating blood from a human patient through a blood filter comprising a nanoworm coated surface to treat viral or bacterial infections by removing or killing the viruses or bacterial. For example, the nanoworm coated surface can be used to treat human patients by in vivo recirculating blood from a human patient through a blood filter comprising a nanoworm coated surface to treat blood cancers, such as by the removal or killing of cancerous leukemia, lymphoma, or myeloma cells.

In certain aspects, the nanoworm composition can be applied as a solution or a cream to human skin as a sanitizer to remove or to kill microbes. In certain aspects, the nanoworm composition be used as a medicine applied topically, intravenously, or orally to the human body as a medicine to target general microbes, such as a general antiviral, or to target a specific microbe, such as a specific virus.

Clauses

Clause 1. A nanoworm, comprising: a plurality of alkene units; and a first set of a plurality of macroCTA polymer units, wherein the macroCTA polymer units of the first set include $R^1$ groups from reversible addition-fragmentation chain-transfer agents.

Clause 2. The nanoworm of clause 1, wherein the first set of the plurality of macroCTA polymer units has a lower critical solution temperature (LCST) in water from −20° C. to +100° C.

Clause 3. The nanoworm of clauses 1 or 2, wherein the first set of the plurality of macroCTA polymer units is configured to be responsive to temperature and configured to be responsive to an environmental condition selected from a group consisting of pH, salinity concentration, and light.

Clause 4. The nanoworm of any of clauses 1-3, wherein the $R^1$ groups of the macroCTA polymer units of the first set are functional groups selected from a group consisting of a carboxylic acid, an alkyne, a pyridine, a dopamine, a thiolactone, a biotin, an azide, a peptide sequence, a sugar sequence, a protease, a glycanase, a polymer, and combinations thereof.

Clause 5. The nanoworm of any of clauses 1-4, wherein the macroCTA polymer units of the first set comprise quaternized amines.

Clause 6. The nanoworm of any of clauses 1-5, wherein the macroCTA polymer units of the first set comprise functionalized quaternized amines selected from a functional group consisting of an alkyl group, a carboxylic acid, an alkyne, a pyridine, a dopamine, a thiolactone, a biotin, an azide, a peptide sequence, a sugar sequence, a protease, a glycanase, a polymer, and combinations thereof.

Clause 7. The nanoworm of any of clauses 1-6, wherein the macroCTA polymer units of the first set comprises two or more sets of functionalized quaternized amines selected from a functional group consisting of an alkyl group, a carboxylic acid, an alkyne, a pyridine, a dopamine, a thiolactone, a biotin, an azide, a peptide sequence, a sugar sequence, a protease, a glycanase, a polymer, and combinations thereof.

Clause 8. The nanoworm of any of clauses 1-7, wherein the macroCTA polymer units of the first set comprise a first set of functionalized quaternized amines of short alkyl quaternized groups and a second set of functionalized quaternized amines of long alkyl quaternized groups, the short alkyl groups having one to four carbons and the long alkyl quaternized groups having five or more carbons.

Clause 9. The nanoworm of any of the clauses 1-8, wherein the nanoworm further comprises: a second set of a plurality of macroCTA polymer units, wherein the macroCTA polymer units of the second set include $R^1$ groups from reversible addition-fragmentation chain-transfer agents, wherein the first set of the plurality of macroCTA polymers units is different from the second set of the plurality of macroCTA polymers units.

Clause 10. The nanoworm of any of the clauses 1-9, wherein the macroCTA polymer units of the first set comprise a polymer selected from a group consisting of poly(N-isopropylacrylamide) (PNIPAM), poly(N,N-(dimethylamino)ethyl methacrylate) (F), poly(N-acetoxylethyl acrylamide) (PNAEAA), poly(acryloylglycine ethyl ester) (PNAGEE), poly((ethylene glycol) methyl ether methacrylate) (PEGMEMA), poly ((propylene glycol)methacrylate) (PPGMA), poly(N, N-dimethylacrylamide) (PDMA), poly(N-decylacrylamide) (PDcA), poly(N,N-diethylacrylamide) (PDEA), poly(N-acryloylglycine) (PNAG), poly(N-acryloylglycine methyl ester) (PNAGME), poly(N-acryloylglycine ethyl ester) (PNAGEE) and poly(N-acryloylglycine propyl ester) (PNAGPE), polyacrylamides, polyacrylates, and copolymers thereof.

Clause 11. The nanoworm of any of the clauses 1-10, wherein the nanoworm comprises at least a hydrophilic portion.

Clause 12. The nanoworm of any of the clauses 1-10, wherein the nanoworm comprises a hydrophilic portion and a hydrophobic portion.

Clause 13. The nanoworm of any of the clauses 1-12, further comprising a plurality of grafted polymers grafted to at least a portion of the first set of the plurality of macroCTA polymer units.

Clause 14. The nanoworm of clause 13, wherein the grafted polymers comprise functionalized quaternized amines selected from a functional group consisting of an alkyl, a carboxylic acid, an alkyne, a pyridine, a dopamine, a thiolactone, a biotin, an azide, a peptide sequence, a sugar sequence, a protease, a glycanase, and combinations thereof.

Clause 15. The nanoworm of any of clauses 13-14, wherein the grafted polymers comprise two or more sets of functionalized quaternized amines selected from a functional group consisting of an alkyl, a carboxylic acid, an alkyne, a pyridine, a dopamine, a thiolactone, a biotin, an azide, a peptide sequence, a sugar sequence, a protease, a glycanase, and combinations thereof.

Clause 16. The nanoworm of any of clauses 13-15, wherein the grafted polymers comprise a first set of functionalized quaternized amines of short alkyl quaternized groups and a second set of functionalized quaternized amines, the short alkyl groups having one to four carbons and the long alkyl quaternized groups having five or more carbons.

Clause 17. The nanoworm of any of clauses 13-16, wherein the grafted polymers comprise: a first set of functionalized quaternized amine groups comprising a peptide sequence, and a second set of functionalized quaternized amine groups comprising a sugar sequence.

Clause 18. The nanoworm of any of clauses 13-17, wherein the grafted polymers are grafted to the $R^1$ groups of the macroCTA polymer units of the first set.

Clause 19. The nanoworm of any of clauses 13-18, wherein the grafted polymers are grafted to quaternary amines of the macroCTA polymer units of the first set.

Clause 20. The nanoworm of any of clauses 13-19, wherein a first set of the plurality of grafted polymers is grafted to the $R^1$ groups of the macroCTA polymer units of the first set, and wherein a second set of the plurality of the plurality of grafted polymers is grafted to quaternary amines of the macroCTA polymer units of the first set.

Clause 21. The nanoworm of any of clauses 13-20, wherein the grafted polymers are formed by a polymerization method selected from a group consisting of addition polymerization, chain polymerization, radical polymerization, metal catalyzed polymerization, nitroxide polymerization, degenerative chain transfer polymerization, RAFT, SET-LRP, condensation polymerization, and combinations thereof Clause 22. The nanoworm of any of clauses 13-21, wherein nanoworm comprises from 20 to 400 of the alkene units, from 1 to 200 of the macroCTA polymer units of the first set, and from 1 to 10,000 of the grafted polymer.

Clause 23. The nanoworm of any of the clauses 1-22, wherein the nanoworm comprises a peptide sequence capable of inhibiting virus attachment and virus-cell membrane fusion.

Clause 24. The nanoworm of any of the clauses 1-23, wherein the nanoworm comprises a peptide sequence capable of disrupting viral envelopes.

Clause 25. The nanoworm of any of the clauses 1-24, wherein the nanoworm comprises a peptide sequence capable of inhibiting viral replication.

Clause 26. The nanoworm of any of the clauses 1-25, wherein the nanoworm comprises an alkyl quaternary ammonium cation quaternized capable of killing a bacteria.

Clause 27. The nanoworm of any of the clauses 13-26, wherein the nanoworm comprises at least a hydrophilic portion.

Clause 28. The nanoworm of any of the clauses 13-26, wherein the nanoworm comprises a hydrophilic portion and a hydrophobic portion.

Clause 29. A composition, comprising a first set of a plurality and a second set of a plurality of the nanoworm of any clauses 1-28.

Clause 30. A coating comprising one or a combination of the nanoworms of any of clauses 1-28.

Clause 31. The coating of clause 30, where the coating is washable to replenish an antimicrobial property of the nanoworm.

Clause 32. The coating of any of clauses 30-31, wherein the nanoworm is non-toxic.

Clause 33. The coating of any of clauses 30-32, wherein the coating is at leas partially transparent.

Clause 34. The coating of any of clauses 30-33, wherein the coating comprises at least a hydrophilic portion, Clause 36. The coating of any of clauses 30-33, wherein the coating comprises a hydrophilic portion and a hydrophobic portion.

Clause 37. A transportation vehicle comprising a coating of any of the clauses 30-35.

Clause 38. A object comprising a coating of any of the clauses 30-35.

EXAMPLES

Materials

Unless otherwise stated, all chemicals were used as received. The solvents included dichloromethane (DCM, Aldrich AR grade), DMSO (Aldrich, 99.9%), n-hexane (Emsure, ACS reagent), chloroform (Emsure, ACS reagent), acetone (ChemSupply, AR grade), petroleum spirit (BR 40-60° C., Univar, AR grade), toluene (ENSURE, ACS reagent, ISO, Reag. Ph Eur), ethyl acetate (ChemSupply, AR grade) and N,N-dimethylacetamide (Aldrich, >99%). Other materials included activated basic alumina (Aldrich: Brockmann I, standard grade, ~150 mesh, 58 A), magnesium sulphate (anhydrous, Scharlau, extra pure), sodium chloride (ChemSupply, AR grade), Milli-Q water (Biolab, 18.2 MΩm), sodium dodecyl sulphate (SDS, Aldrich, 99%), N,N'-dicyclohexylcarbodiimide (DCC, Aldrich, 99%), 4-(dimethylamino)pyridine (DMAP, Merck, 99%), 1-butanethiol (Aldrich, 99%), propargyl alcohol (Aldrich, 99%), lithium chloride (Aldrich, 99%), tripotassium phosphate (Aldrich, ≥98%), sodium hydrogen carbonate (Aldrich, 99.5%), hydrochloric acid (36%, Ajax, AR grade), sulfuric acid (Aldrich, 98%), hydrogen peroxide (Aldrich, 30 wt. % in water, ACS reagent), carbon disulfide (Aldrich, >99.9%), 2-bromo-2-methylpropionic acid (Aldrich, 98%), methyl-2-bromopropionate (MBP, Aldrich, 98%), iodooctane (Aldrich, 98%), iodomethane (Aldrich, 99%, contains copper as stabilizer), copper (II) sulfate (Aldrich, 99%), L-ascorbic acid (Aldrich, 99%), poly(ethyleneimine) solution (PEI, Aldrich, 50 wt. % in water, Mn 1800, Mw 2000), GRGD (Gly-Arg-Gly-Asp) azide (Auspep, 97%), and glass surfaces. Styrene (STY, Aldrich, >99%) and N,N-(dimethylamino)ethyl methacrylate (DMAEMA, Aldrich, 98%) were passed through a basic alumina column to remove any inhibitors. N-isopropylacrylamide (NIPAM, Aldrich, 97%) was recrystallized from n-hexane/toluene (9/1, v/v). Azobisisobutyronitrile (AIBN, Riedel-de Haen) was recrystallized from methanol twice prior to use. Ethyl α-bromoisobutyrate (EBiB, Aldrich, 98%).

Analytical Methods

Nuclear Magnetic Resonance (NMR). All NMR spectra were conducted on a Bruker DRX 400 MHz spectrometer using an external lock ($CDCl_3$ or DMSO-d6).

Size Exclusion Chromatography (SEC) and Triple Detection-Size Exclusion Chromatography (TD-SEC). Analysis of the molecular weight distributions of the polymers were determined using a Polymer Laboratories GPC50 Plus equipped with differential refractive index detector. Absolute molecular weights of polymers were determined using a Polymer Laboratories GPC50 Plus equipped with dual angle laser light scattering detector, viscometer, and differential refractive index detector. High performance liquid chromatography (HPLC) grade N,N-dimethylacetamide (DMAc, containing 0.03 wt % LiCl) was used as the eluent at a flow rate of 1.0 mL/min. Separations were achieved using two PLGel Mixed B (7.8×300 mm) SEC columns connected in series and held at a constant temperature of 50° C. The triple detection system was calibrated using a 5 mg/mL 110 K polystyrene (PSTY) standard. Samples of known concentration were freshly prepared in DMAc+0013 wt % LiCl and passed through a 0.45 μm PTFE syringe filter prior to injection. The absolute molecular weights and do/dc values were determined using Polymer Laboratories Multi Cirrus software based on the quantitative mass recovery technique.

Dynamic Light Scattering (DLS). Dynamic Light Scattering measurements were performed using a Malvern Zetasizer Nano Series 3000HS running DTS software operating a 4 mW He—Ne laser at 633 nm. Analysis was performed at an angle of 173° and at a temperature of 25° C. The number-average hydrodynamic particle diameter ($D_h$) and polydispersity index ($PDI_{DLS}$) were measured. The $PDI_{DLS}$ describes the width of the particle size distribution and was calculated from a Cumulants analysis of the DLS measured intensity autocorrelation function and is related to the standard deviation of the hypothetical Gaussian distribution (i.e., $PDI_{DLS}=\sigma^2/ZD^2$, where σ is the standard deviation and ZD is the Z average mean size).

Lower Critical Solution temperature (LCST). For determination of the lower critical solution temperature (LCST) of the macroCTAs, the macroCTAs were dissolved in Milli-Q water at 10 mg/mL in an ice bath. The solution was then filtered using a 0.45 μm cellulose syringe filter directly into a DLS cuvette. The polymer solution was cooled to 5° C. and the cuvette placed in DLS instrument. The measurement was carried out by slowly increasing the temperature from 5 to 70° C. at a ramp rate of 2° C./min controlled by the standard operating procedure software.

Upper Critical Solution temperature (LCST). For determination of the lower critical solution temperature (LCST) of the macroCTAs, the macroCTAs were dissolved in water at 10 mg/mL in water bath at 70° C. The solution was then filtered using a 0.45 μm (micrometer) cellulose syringe filter directly into a DLS cuvette. The cuvette was placed in DLS instrument. The measurement was carried out by slowly cooling the polymer solution from 70° C. to below 1° C.

RAFT Agents

Ester functional RAFT agent. An ester functional RAFT agent (ester RAFT agent) of methyl 2-(butylthiocarbonothioylthio)propanoate (MCEBTTC) RAFT agent was synthesized according to the following reaction scheme (I).

(I)

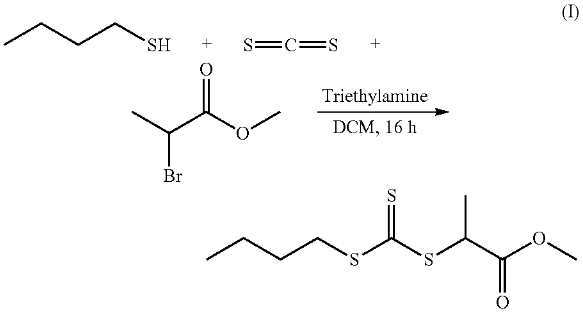

Carboxylic acid functional RAFT agent. A carboxylic acid functional RAFT agent (acid RAFT agent) was synthesized according to reaction scheme (II).

(II)

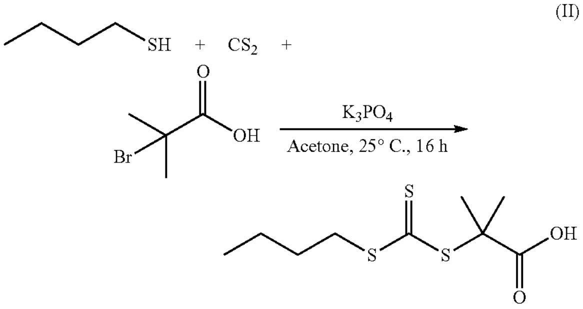

Alkyne functional RAFT agent. An alkyne functional RAFT agent (alkyne RAFT agent) was synthesized according to reaction scheme (III).

(III)

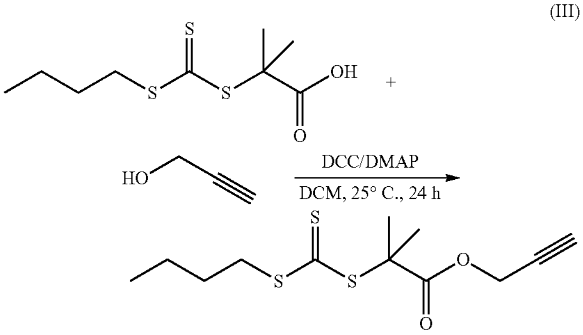

Synthesis of Poly(NIPAM) MacroCTA by Ester RAFT Agent

A macroCTA of a polymer of NIPAM was synthesized according to reaction scheme (IV).

(IV)

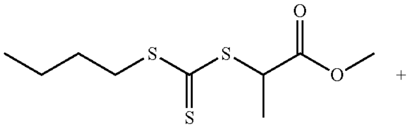

-continued

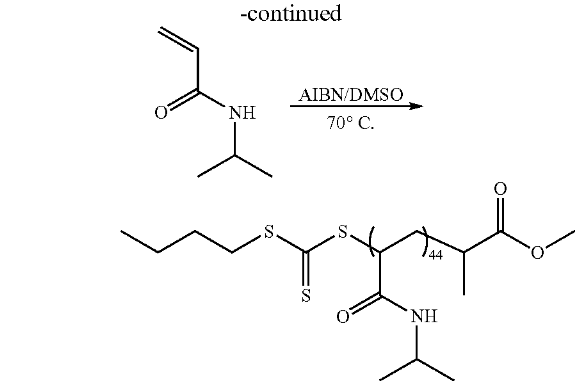

The concentration ratio of NIPAM:RAFT (MCEBTTC): AIBN was 44:1:0.1 and the ratio of DMSO to NIPAM was 2/1 (v/w). NIPAM (4.31 g, 3.81x10−2 mol), MCEBTTC (0.219 g, 8.68x10−4 mol) and AIBN (14.2 mg, 8.65x10−5 mol) were dissolved in DMSO (8.6 mL), The mixture was deoxygenated by purging with argon for 40 min, and heated at 70° C. for 18 h. The polymerization was then stopped by cooling to 0° C. in an ice bath and exposure to air. The solution was diluted with chloroform (200 mL) and washed five times with 40 mL of Milli-Q water. The chloroform was then dried over anhydrous MgSO4, filtered and reduced in volume by rotary evaporation. The polymer was recovered by precipitation into large excess of diethyl ether (400 mL), isolated by filtration, and then dried under vacuum for 24 h at room temperature to get a yellow powder product. The polymer produce is termed macro($PNIPAM_{44}$)-A (macroCTA-A), Synthesis of Poly(NIPAM/DMAEMA) MacroCTA by Alykne RAFT Agent A macroCTA copolymer of NIPAM and DMAEMA was synthesized according to reaction scheme (V).

(V)

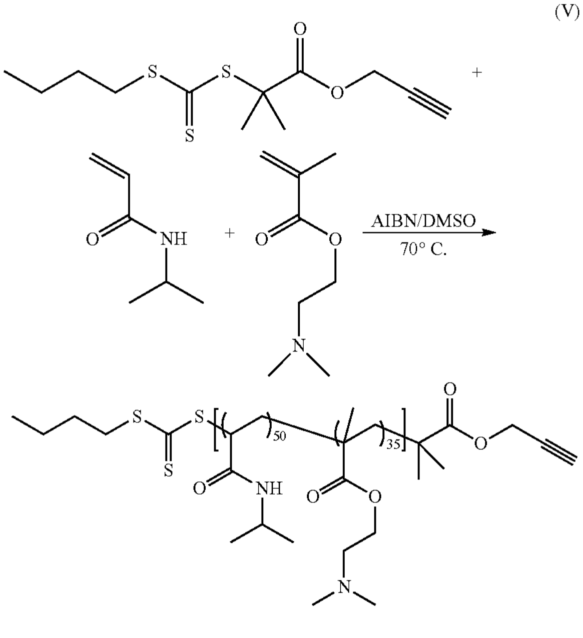

The concentration ratio of NIPAM:DMAEMA:RAFT: AIBN was 50:30:1:0.15, and the ratio of DMSO to NIPAM and DMAEMA was 1.1/1 (vlw). NIPAM (1.99 g, 1.76x10-2 mol), DMAEMA (1.66 g, 1.05x10−2 mol), RAFT alkyne (0.102 g, 3.51x10−4 mol) and AIBN (8.6 mg, 5.27x10−5 mol) were dissolved in DMSO (4 mL.). The mixture was deoxygenated by purging with argon for 40 min, heated to 70° C. and polymerized for 17 h. The reaction was stopped by cooling to 0° C. in an ice bath and exposure to air. The solution was then diluted with 4 mL of chloroform and precipitated into large excess of petroleum spirit (250 mL) and then isolated by centrifugation. The dissolution and precipitation cycle was repeated three times. Then, product was dissolved in Milli-Q water and freeze-dried to recover as a yellow powder. The polymer produce is termed macro ($P(NIPAM_{50}$-co-$DMAEMA_{35})$)-B (macroCTA-B).

Synthesis of Poly(NIPAM/DMAEMA) MacroCTA by Ester RAFT Agent

A macroCTA of a copolymer of NIPAM and DMAEMA was synthesized according to reaction scheme (VI).

(VI)

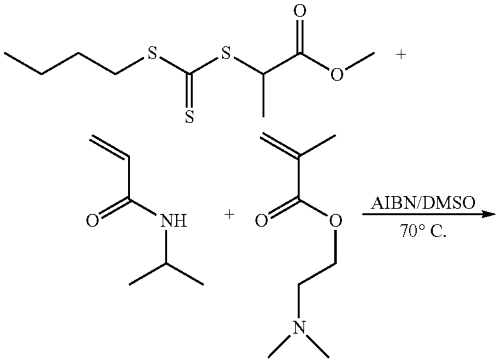

-continued

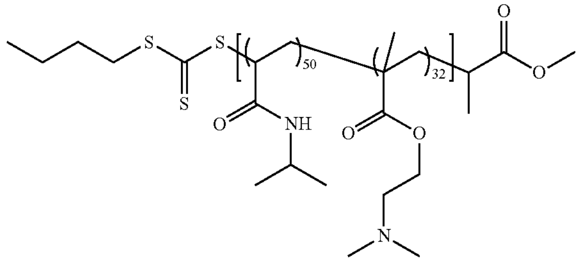

The concentration ratio of NIPAM:DMAEMA:RAFT:AIBN was 50:30:1:0,15, and the ratio of DMSO to NIPAM and DMAEMA was 1.1/1 (v/w). NIPAM (2 g, 1.76x10−2 mol), DMAEMA (1.66 g, 1.05x10−2 mol), RAFT MCEBTTC (0.089 g, 3.53x10−4 mol) and AIBN (8.7 mg, 5.29x10−5 mol) were dissolved in DMSO (4 mL). The mixture was deoxygenated by purging with argon for 40 min, then heated at 70° C. and polymerized for 16 h. The reaction was stopped by cooling to 0° C. in an ice bath and exposure to air. The solution was then diluted with 4 mL of chloroform and precipitated into large excess of petroleum spirit (250 mL) and then isolated by centrifugation. The dissolution and precipitation cycle was repeated three times. Then, product was dissolved in Milli-Q water and freeze-dried to recover as a yellow powder. The polymer produce is termed macro($P(NIPAM_{50}$-co-$DMAEMA_{32})$)-C (macroCTA-C).

Quaternization of Poly(NIPAM/DMAEMA) MacroCTA

A macroCTA of a copolymer of NIPAM and DMAEMA was synthesized according to reaction scheme (VII)

(VII)

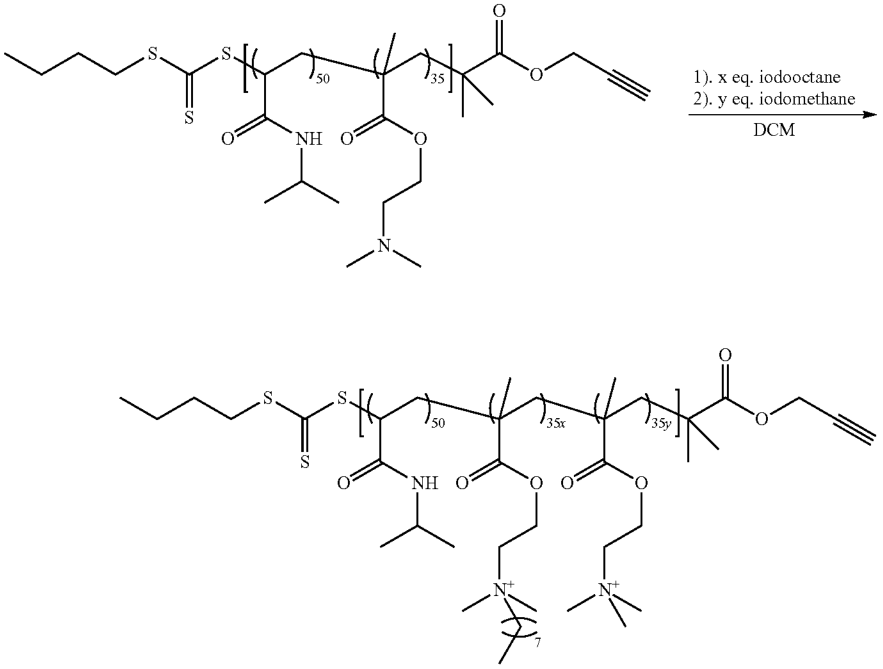

Alkyne Raft Agent polymerized P(NIPAM50-co-DMAEMA35) (Macro(P(NIPAM50-co-DMAEMA35)-B, 50 mg, mw=11451) was dissolved in DCM (1.2 mL). Then, iodooctane (240.13 g/mol, 1.33 g/cm3) was added to polymer solution and the mixture shaken for 8 h at 23° C. Then, iodomethane (141.94 g/mol, 2.28 g/cm3) was added and the mixture shaken for an additional 11 h at 23° C. The polymer solution was dialyzed against acetone (3×500 mL) followed by dialysis against Milli-Q water (3×500 mL) (MWCO 3500). The sample was freeze-dried to obtain a white powder as a product. Different ratios of iodooctane and iodomethane were used according to TABLE 4.

TABLE 4

| Reaction | X eq iodooctane | Y eq. iodomethane |
|---|---|---|
| I | 0 | 1 |
| II | 0.1 | 0.9 |
| III | 0.3 | 0.7 |
| IV | 0.5 | 0.5 |
| V | 0.7 | 0.3 |
| VI | 0.9 | 0.1 |

Temperature Directed Morphology Transformation (TDMT) Method to Produce Nanoworms The styrene emulsion polymerization using Macro(PNIPAM44)-A and Macro(P(NIPAM50-co-DMAEMA35))-B was used to produce nanoworms. In a Schlenk tube, Macro (PNIPAM44)-A (40 wt. %, 70 mg, 1.3x10−5 mol), Macro (P(NIPAM50-co-DMAEMA35))-B (60 wt. %, 105 mg, 9.2x 10−6 mol) and SDS (7.25 mg, 2.5x10−5 mol) were dissolved in cold Milli-Q water (3.25 mL). The mixture was deoxygenated by purging with argon for 20 min. AIBN (0.37 mg, 2.2x10−6 mol) was dissolved in styrene (0.1304 g, 1.3x10−3 mol) and the solution injected into the macroCTAs mixture, which was then purged with argon for another 5 min in an ice bath before heating to 70° C. The polymerization was stopped after 4 h by exposing the reaction to air at 70° C.

The latex (1 mL) at 70° C. was mixed with 15-20 μL toluene, cooled to 23° C., and left to stand at 23° C. for 1 h. Then, the solution was cooled gradually to 10° C. over 10 min and left to stand at 10° C. for 20 h. The nanostructure was characterized by TEM to confirm the formation of worm-like nanostructures, and then freeze-dry to obtain a white powder.

Protocols for Post-Modification of Alkyne PDMAEMA Nanoworms (40 wt % of MacroCTA-A and 60 wt % MacroCTA-B)

Nanoworm Example 1 (Alkyne P(DMAEMA) Nanoworms)

Alkyne terminated poly(DMAEMA) nanoworms comprising poly(NIPAM) and alkyne terminated poly(NIPAM-co-DMAEMA) was produced as follows. In a Schlenk tube, macro(PNIPAM44)-A (70 mg, 1.3x10−5 mol), macro(P (NIPAM50-co-DMAEMA35))-B (105 mg, 9.2x10−6 mol), and SDS (7.25 mg, 2.5x10−5 mol) were dissolved in cold Milli-Q water (3.25 mL). The mixture was deoxygenated by purging with argon for 20 min. AIBN (0.37 mg, 2.2x10−6 mol) was dissolved in styrene (0.1304 g, 1.3x10−3 mol) and the solution injected into the macroCTAs mixture, which was then purged with argon for another 5 min in an ice bath before heating to 70° C. The polymerization was stopped after 4 h by exposing the reaction to air at 70° C. and the latex (1 mL) at 70° C. was mixed with 20 microliters (μL) toluene, cooled to 23° C., and left to stand at 23° C. for 1 h. Then, the solution was cooled gradually to 10° C. over 10 min and left to stand at 10° C. for 20 h. The nanostructure was characterized by TEM to confirm the formation of worm-like nanostructures and then freeze-dry to obtain a white powder, Nanoworm Example 2 (Peptide P(DMAEMA) Nanoworms)

Peptide terminated poly (DMAEMA) nanoworms was produced as follows by functionalizing the alkyne terminated poly(NIPAM-co-DMAEMA) of Nanoworm Example 1 to be terminated with GRGD peptides. GRGD-azide (1 eq.) and alkyne worms (Nanoworm Example 1, 1 eq.) were dispersed in the mixture of Milli-Q water and DMSO (10% v.) (2 mL). The mixture was deoxygenated by purging with argon for 40 min. CuSO4 (3 eq.) was dissolved in 0.6 mL of Milli-Q water/DMSO (10% v.) and purged with Ar for 20 min. Ascorbic acid (7 eq.) was dissolved in 0.6 mL of Milli-Q water/DMSO (10% v.) and purged with Ar for 20 min. Ascorbic acid solution was injected to the suspension of worms and GRGD-azide by degassed syringe followed by the injection of CuSO4 solution. After 19 h of stirring at 23° C., the reaction was stopped by exposure to the air and the suspension was dialysed against Milli-Q water for 36 h (3500 MWCO). The resulting solution was freeze-dried to obtain powder.

Nanoworm Example 3 (Alkyne P(DMAEMA) Nanoworms Quaternized with Iodomethane)

Alkyne poly(DMAEMA) Nanoworms quaternized with iodomethane was produced as follows as follows by quaternizing the alkyne terminated poly(NIPAM-co-DMAEMA) of Nanoworm Example 1 with methyl groups. Redispersed Nanoworm Example 1 (VB-B10-R67A, 20 mg, MW 12619) in Milli-Q water (90%)/DMSO (10%) (total volume 1 mL), Then, add 1.6 μL of iodomethane (141.94 g/mol, 2.28 g/cm$^3$) to nanoworms suspension and keep shaking for 19 h at 23° C. The suspension was dialysed against Milli-Q water for 36 h (3500 MWCO). The resulting solution was freeze-dried to obtain powder.

Nanoworm Example 4 (Alkyne P(DMAEMA) Nanoworms Quaternized with Iodooctane (10%) and Iodomethane (90%)

Alkyne poly(DMAEMA) Nanoworms quaternized with iodomethane was produced as follows by quaternizing the alkyne terminated poly(NIPAM-co-DMAEMA) of Nanoworm Example 1 with methyl groups and octyl groups. The DMAEMA groups of the macroCTA of nanoworms 1 were quaternized with methyl groups and octyl groups. Redispersed Nanoworm Example 1 (VB-B10-R67A, 20 mg, MW 12619) in Milli-Q water (90%)/DMSO (10%) (total volume 1 mL). Then, add 0.4 μL of iodooctane (240.13 g/mol, 1.33 g/cm3) using stock solution, keep shaking for 8 h at 23° C. Then, add 1.3 μL of iodomethane (141.94 g/mol, 2.28 g/cm3) and keep shaking for 11 h at 23° C. The suspension was dialysed against Milli-Q water for 36 h (3500 MWCO). The resulting solution was freeze-dried to obtain powder.

Nanoworm Example 5 (Peptide P(DMAEMA) Nanoworms Quaternized with Iodomethane

Peptide poly(DMAEMA) nanoworns quaternized with iodomethane were produced as follows by quaternizing the peptide terminated poly (DMAEMA) of Nanoworm Example 2 with methyl groups. Redispersed Nanoworm Example 2 (MW 12824) in Milli-Q water 90%)/DMSO (10%) (total volume 1 mL). Then, add 0.92 μL of iodomethane (141.94 g/mol, 2.28 g/cm3) to nanoworms suspension and keep shaking for 19 h at 23° C. The suspension was dialysed against Milli-Q water for 36 h (3500 MWCO). The resulting solution was freeze-dried to obtain powder.

Nanoworm Example 6 (Peptide P(DMAEMA) Nanoworms Quaternized with Iodooctane (10%) and Iodomethane (90%)

Peptide poly(DMAEMA) nanoworms quaternized with iodooctane (10%) and iodomethane (90%) were produced as follows by quaternizing the peptide terminated poly (DMAEMA) of Nanoworm Example 2 with methyl groups and octyl groups, Redispersed nanoworm 1 functionalized with GRGD peptide (VB-B10-R69, mg, MW 12824) in Milli-Q water (90%)/DMSO (10%) (total volume 1 mL). Then, add 0.24 μL of iodooctane (240.13 g/mol, 1.33 g/cm3) using stock solution, keep shaking for 8 h at 23° C. Then, add 1 μL of iodomethane (141.94 g/mol, 2.28 g/cm3) and keep shaking for 11 h at 23° C. The suspension was dialysed against Milli-Q water for 36 h (3500 MWCO). The resulting solution was freeze-dried to obtain powder.

Nanoworm Example 7 (Alkyne P(DMAEMA) Nanoworms Quaternized with Iodooctane (10%) and Iodomethane (90%)

Alkyne poly(DMAEMA) Nanoworms quaternized with iodooctane (10%) and iodomethane (90%) was produced as follows by quaternizing the alkyne terminated poly(NIPAM-co-DMAEMA) of Nanoworm Example 1 with methyl groups and octyl groups. Redispersed Nanoworm Example 1 (40 mg, MW 11994) in Milli-Q water (85%)/DMSO (15) (total volume 1.5 mL). Then add 0.1 eq. iodooctane (0.864057 μL, 240.13 g/mol, 1.33 g/cm3), keep shaking for 8 h at 23° C. Then, add 0.9 eq. iodomethane (2.681392 μL, 141.94 g/mol, 2.28 g/cm3) and keep shaking for 11 h at 23° C. The suspension was dialysed against Milli-Q water for 36 h (3500 MWCO). The resulting solution was freeze-dried to obtain powder.

Nanoworm Example 8 (Alkyne P(DMAEMA) Nanoworms Quaternized with Iodooctane (30%) and Iodomethane (70%)

Alkyne poly(DMAEMA) Nanoworms quaternized with iodooctane (30%) and iodomethane (70%) was produced as follows by quaternizing the alkyne terminated poly(NIPAM-co-DMAEMA) of Nanoworm Example 1 with methyl groups and octyl groups. Redispersed Nanoworm Example 1 (40 mg, MW 11994) in Milli-Q water (85%)/DMSO (15%) (total volume 1.5 mL). Then add 0.3 eq. iodooctane (2.592172 μL 240.13 g/mol, 1.33 g/cm3), keep shaking for 8 h at 23° C. Then, add 0.7 eq, iodomethane (2.085527 μL, 141.94 g/mol, 2.28 g/cm3) and keep shaking for 11 h at 23° C. The suspension was dialysed against Milli-Q water for 36 h (3500 MWCO). The resulting solution was freeze-dried to obtain powder.

Nanoworm Example 9 (Alkyne P(DMAEMA) Nanoworms Quaternized with Iodooctane (50%) and Iodomethane (50%)

Alkyne poly(DMAEMA) Nanoworms quaternized with iodooctane (50%) and iodomethane (50%) was produced as follows by quaternizing the alkyne terminated poly(NIPAM-co-DMAEMA) of Nanoworm Example 1 with methyl groups and octyl groups. Redispersed Nanoworm Example 1 (40 mg, MW 11994) in Milli-Q water (85%)/DMSO (15%) (total volume 1.5 mL). Then add 0.5 eq. iodooctane (4.320287 μL 240.13 g/mol, 1.33 g/cm3), keep shaking for 8 h at 23° C. Then, add 0.5 eq. iodomethane (1.489662 μL, 141.94 g/mol, 2.28 g/cm3) and keep shaking for 11 h at 23° C. The suspension was dialysed against Milli-Q water for 36 h (3500 MWCO). The resulting solution was freeze-dried to obtain powder.

Nanoworm Example 10 (Alkyne P(DMAEMA) Nanoworms Quaternized with Iodooctane (70%) and Iodomethane (30%)

Alkyne poly(DMAEMA) Nanoworms quaternized with iodooctane (70%) and iodomethane (30%) was produced as follows by quaternizing the alkyne terminated poly(NIPAM-co-DMAEMA) of Nanoworm Example 1 with methyl groups and octyl groups. Redispersed Nanoworm Example 1 (40 mg, MW 11994) in Milli-Q water (85%)/DMSO (15) (total volume 1.5 mL). Then add 0.7 eq. iodooctane (6.048402 μL, 240.13 g/mol, 1.33 g/cm3), keep shaking for 8 h at 23° C. Then, add 0.3 eq, iodomethane (0.893797 μL, 141.94 g/mol, 2.28 g/cm3) and keep shaking for 11 h at 23° C. The suspension was dialysed against Milli-Q water for 36 h (3500 MWCO). The resulting solution was freeze-dried to obtain powder.

Nanoworm Example 11 (Alkyne P(DMAEMA) Nanoworms Quaternized with Iodooctane (90%) and Iodomethane (10%)

Alkyne poly(DMAEMA) Nanoworms quaternized with iodooctane (90%) and iodomethane (10%) was produced as follows by quaternizing the alkyne terminated poly(NIPAM-co-DMAEMA) of Nanoworm Example 1 with methyl groups and octyl groups. Redispersed Nanoworm Example 1 (40 mg, MW 11994) in Milli-Q water (85%)/DMSO (15%) (total volume 1.5 mL). Then add 0.9 eq. iodooctane (7.776517 μL, 240.13 g/mol, 1.33 g/cm3), keep shaking for 8 h at 23° C. Then, add 0.1 eq, iodomethane (0.297932 μL, 141.94 g/mol, 2.28 g/cm3) and keep shaking for 11 h at 23° C. The suspension was dialysed against Milli-Q water for 36 h (3500 MWCO). The resulting solution was freeze-dried to obtain powder.

Nanoworm Example 12 (Peptide P(DMAEMA) Nanoworms Quaternized with Iodooctane (90%) and Iodomethane (10%)

Peptide poly(DMAEMA) nanoworms quaternized with iodooctane (90%) and iodomethane (10%) was produced as follows by functionalizing the alkyne terminated poly(NIPAM-co-DMAEMA) of Nanoworm Example 7 to be terminated with GRGD peptides. GRGD-azide (1 eq.) and alkyne worms (Nanoworm Example 7, 1 eq.) were dispersed in the degassed mixture of Milli-Q water and DMSO (10% v.) (1.4 mL). Ascorbic acid degassed solution in water (7 eq) was injected to the suspension of worms and GRGD-azide by degassed syringe followed by the injection of $CuSO_4$ solution in water (3 eq). After 19 h of stirring at 23° C., the reaction was stopped by exposure to the air and the suspension was dialysed against Milli-Q water for 36 h (3500 MWCO). The resulting solution was freeze-dried to obtain powder.

Nanoworm Example 13 (Peptide P(DMAEMA) Nanoworms Quaternized with Iodooctane (30%) and Iodomethane (70%)

Peptide poly(DMAEMA) nanoworms quaternized with iodooctane (30%) and iodomethane (70%) was produced as follows by functionalizing the alkyne terminated poly(NIPAM-co-DMAEMA) of Nanoworm Example 8 to be terminated with GRGD peptides. GRGD-azide (1 eq.) and alkyne worms (Nanoworm Example 8, 1 eq,) were dispersed in the degassed mixture of Milli-Q and DMSO (10% v.) (1.4 mL). Ascorbic acid degassed solution in water (7 eq) was injected to the suspension of worms and GRGD-azide by degassed syringe followed by the injection of CuSO4 solution in water (3 eq). After 19 h of stirring at 23° C., the reaction was stopped by exposure to the air and the suspension was dialysed against Milli-Q water for 36 h (3500 MWCO). The resulting solution was freeze-dried to obtain powder.

Nanoworm Example 14 (Peptide P(DMAEMA) Nanoworms Quaternized with Iodooctane (50%) and Iodomethane (50%)

Peptide poly(DMAEMA) nanoworms quaternized with iodooctane (50%) and iodomethane (50%) was produced as follows by functionalizing the alkyne terminated poly(NIPAM-co-DMAEMA) of Nanoworm Example 9 to be terminated with GRGD peptides. GRGD-azide (1 eq.) and alkyne worms (Nanoworm Example 9, 1 eq.) were dispersed in the degassed mixture of Milli-Q water and DMSO (10% v.) (1.4 mL). Ascorbic acid degassed solution in water (7 eq) was injected to the suspension of worms and GRGD-azide by degassed syringe followed by the injection of CuSO4 solution in water (3 eq). After 19 h of stirring at 23° C., the reaction was stopped by exposure to the air and the suspension was dialysed against Milli-Q water for 36 h (3500 MWCO). The resulting solution was freeze-dried to obtain powder.

Nanoworm Example 15 (Peptide P(DMAEMA) Nanoworms Quaternized with Iodooctane (70%) and Iodomethane (30%)

Peptide poly(DMAEMA) nanoworms quaternized with iodooctane (70%) and iodomethane (30%) was produced as follows by functionalizing the alkyne terminated poly(NIPAM-co-DMAEMA) of Nanoworm Example 10 to be terminated with GRGD peptides. GRGD-azide (1 eq.) and alkyne worms (Nanoworm Example 10, 1 eq.) were dispersed in the degassed mixture of Milli-Q and DMSO (10% v.) (1.4 mL). Ascorbic acid degassed solution in water (7 eq) was injected to the suspension of worms and GRGD-azide by degassed syringe followed by the injection of CuSO4 solution in water (3 eq). After 19 h of stirring at 23° C., the reaction was stopped by exposure to the air and the suspension was dialysed against Milli-Q water for 36 h (3500 MWCO). The resulting solution was freeze-dried to obtain powder, Nanoworm Example 16 (Peptide P(DMAEMA) Nanoworms Quaternized with Iodooctane (90%) and Iodomethane (10%)

Peptide poly(DMAEMA) nanoworms quaternized with iodooctane (90%) and iodomethane (10%) was produced as follows by functionalizing the alkyne terminated poly(NIPAM-co-DMAEMA) of Nanoworm Example 11 to be terminated with GRGD peptides, GRGD-azide (1 eq.) and alkyne worms (Nanoworm Example 11, 1 eq.) were dispersed in the degassed mixture of Milli-Q water and DMSO (10% v.) (1.4 mL). Ascorbic acid degassed solution in water (7 eq) was injected to the suspension of worms and GRGD-azide by degassed syringe followed by the injection of CuSO4 solution in water (3 eq). After 19 h of stirring at 23° C., the reaction was stopped by exposure to the air and the suspension was dialysed against Milli-Q water for 36 h (3500 MWCO). The resulting solution was freeze-dried to obtain powder.

Temperature-Responsive MacroCTAS

Three pH-responsive and temperature-responsive macroCTAs were synthesized with different amounts of NIPAM and DMAEMA made by reversible addition-fragmentation chain transfer (RAFT) polymerization. All macroCTAs contained a trithioester (or RAFT) end-group that allowed further polymerization of the macroCTAs with other monomers to form copolymers, which could then be transferred in situ to nanoworms. Characterization of the three macroCTAs was obtained using size exclusion chromatography (SEC) and NMR and is set forth in TABLE 5. MacroCTA-B consisted of an alkyne functional group for further copper-catalyzed alkyne-azide cycloaddition (CuAAC) "click" reactions. The polymerizations were all well controlled with relatively narrow molecular weight distributions.

The lower critical solution temperatures (LCSTs) of the three macroCTAs were determined in water using the DLS instrument. The LCST is characterized by the shape increase in the size at a particular temperature. AH three MacroCTAs as shown in TABLE 5 had LCSTs that were close to 30° C., which provides a good LCST to produce nanoworms to provide antimicrobial properties.

TABLE 5

| MacroCTA | Conversion (%) NIPAM | Conversion (%) DMAEMA | Conversion (%) Total | Repeating units (NMR) NIPAM | Repeating units (NMR) DMAEMA |
|---|---|---|---|---|---|
| MacroCTA-A | 98 | 0 | 98 | 44 | 0 |
| MacroCTA-B | 88 | 100 | 93 | 50 | 35 |
| MacroCTA-C | 89 | 100 | 94 | 50 | 32 |

| MacroCTA | Mn (Theory) | Mn (1H NMR) | SEC (Abs) Mn | Đ | SEC (RI) Mn | Đ | LCST ° C. |
|---|---|---|---|---|---|---|---|
| MacroCTA-A | 5130 | 5230 | 4900 | 1.09 | 16680 | 1.17 | 30 |
| MacroCTA-B | 9990 | 11450 | 13100 | 1.16 | 21740 | 1.59 | 27 |
| MacroCTA-C | 10000 | 10930 | 10060 | 1.07 | 23830. | 1.43 | 29 |

The conversion percentage (%) was calculated by comparing integrations of polymers and residual monomers from 1H NMR. Total conversion percentage of polymer (Total) was calculated as follows: total conversion=[[(conversion (NIPAM)×mNIPAM)+(conversion(DMAEMA)×mDMAEMA)]/(mNIPAM+mDMAEMA)]×100. Mn (theory) was calculated following from the procedure as set form in J. Am. Chem. Soc., 2015, 137 (50), 15652-15655. Mn (1H NMR) was calculated from 1H NMR. Mn (SEC Abs) was calculated using eDMAc+0.03 wt. % LiCl as eluent with polystyrene as calibration standard. LCST is defined here as the minimum temperature where the macroCTA is insoluble in part or in whole in a stated liquid medium.

Figure 7:
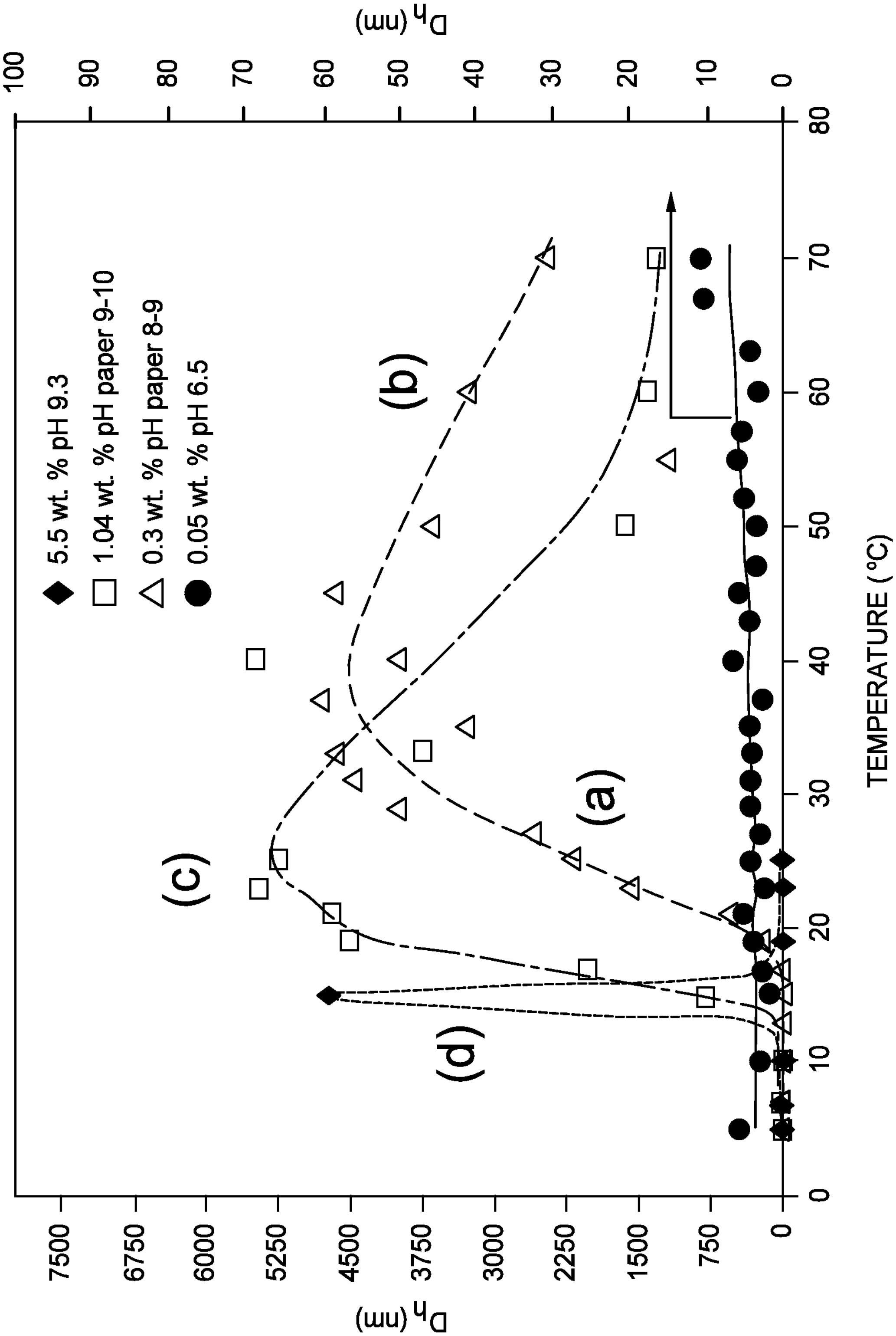
FIG. 7 is a graph showing examples of determining LCSTs of a macroCTA in water at different weight fractions and at different pHs according to certain aspects.

FIG. 7 is a graph showing examples of determining LCSTs of a macroCTA-C in water at different weight fractions and at different pHs according to certain aspects. The LCST profiles of MacroCTA-C (0.05 wt. %) at different wt % in sodium chloride solution (71 mg/mL). The pH was adjusted with HCl (0.14 M) to 6.592 (curve a). Additional macroCTA-C was then added to get a concentration of 3 mg/mL (0.3 wt %, curve b), 10.5 mg/mL (1.04 wt %, curve c) or 57.7 mg/mL (5.5 wt %, curve d). pH of solution changed to ~9-10. The LCSTs at each wt. fraction of polymer were measured.

The different weight fractions and different pHs simulates the change in polymer properties from water-soluble to water-insoluble (or polymer conformation from coil to globule) when a water (or mucosal) droplet lands on the nanoworm-coated surface, in which the surface properties of a coating are largely governed by the macroCTA polymer units on the nanoworm. The water solution included a high amount of salt (71 mg/mL) to simulate the high salt found in body fluids, such as saliva, urine, sweet, and other body fluids. At a low weight fraction of polymer (0.05 wt % at pH=6.5) there was no observable LCST up to 70° C., suggesting that the droplet will initially change a polymer-coated surface to be highly water-soluble resulting in rapid droplet wetting across the surface, and will thus provide high capture efficiency of the microbes. Increasing the weight fraction and pH to 0.3 wt % at pH=8-9, the LCST was about 19.5° C. Further increasing the weight fraction and pH to 1.04 wt % at pH=9-10, the LCST was about 14° C. Further increasing the weight fraction and pH to 5.5 wt. % at pH of about 9.3, the LCST of about 13° C.

This demonstrated that the initial droplet on the surface will experience a low concentration of the macroCTA polymer units, but as the droplet evaporates the macroCTA polymer weight fraction will increase. With an increased weight fraction, the buffering capacity of the alkaline DMAEMA in the macroCTA polymer units increases which increases the pH. At a certain weight fraction and pH, the polymer surface will be restored to its initial water-insoluble condition.

Figure 8:
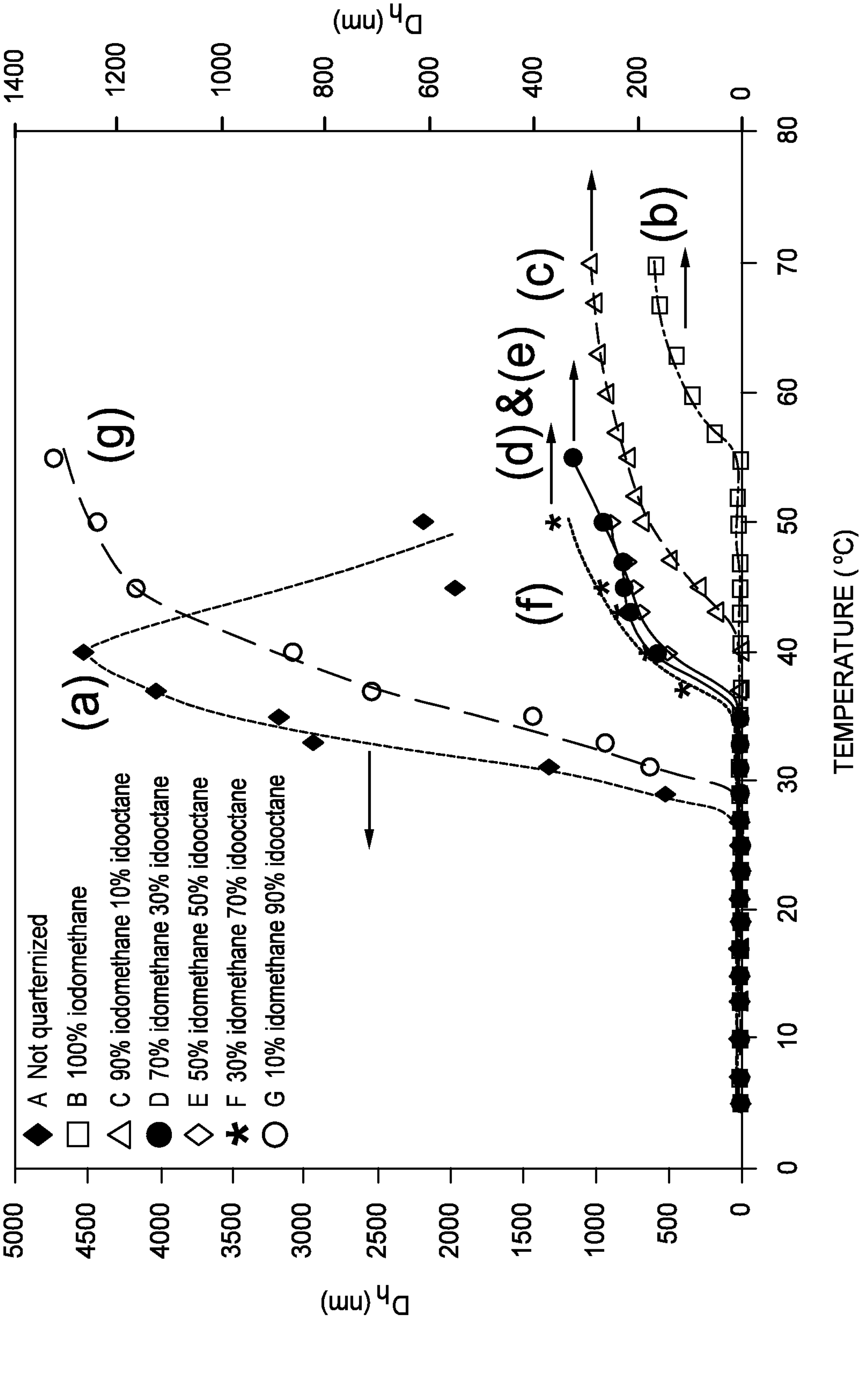
FIG. 8 is a graph showing examples of incorporating cationic and hydrophobic moieties into macroCTAs according to certain aspects.

FIG. 8 is a graph showing examples of incorporating cationic and hydrophobic moieties into macroCTAs according to certain aspects. The LCST profiles of MacroCTA-B after post-modification with different iodo-compounds (10 mg/mL in Milli-Q water) are as follows: (a) Not quaternized (LCST 27° C.); (b) 100% iodomethane (LCST 55° C.); (c) iodomethane (90%) and iodooctane (10%) (LCST 40° C.); (d) iodomethane (70%) and iodooctane (30%) (LCST 35° C.); (e) iodomethane (50%) and iodooctane (50%) (LCST 35° C.); (f) iodomethane (30%) and iodooctane (70%) (LCST 35° C.); (g) iodomethane (10%) and iodooctane (90%) (LCST 29° C.).

The cationic and hydrophobic moieties are highly effective in killing bacteria. As shown in Scheme 1A, iodomethane and iodooctane were reacted to the amine on DMAEMA to produce quaternary cationic amines with different ratios of methane and octane groups on the surface of the nanoworms. The LCST was determined for macroCTAs with various ratios as shown in FIG. 8. With the increase in the ratio of octane, the LCST decreased from ~55° C. (100% methane) to 30° C. (90% octane). This demonstrated that the LCST of the nanoworms can be finely tuned to a particular environmental condition.

Figure 9:
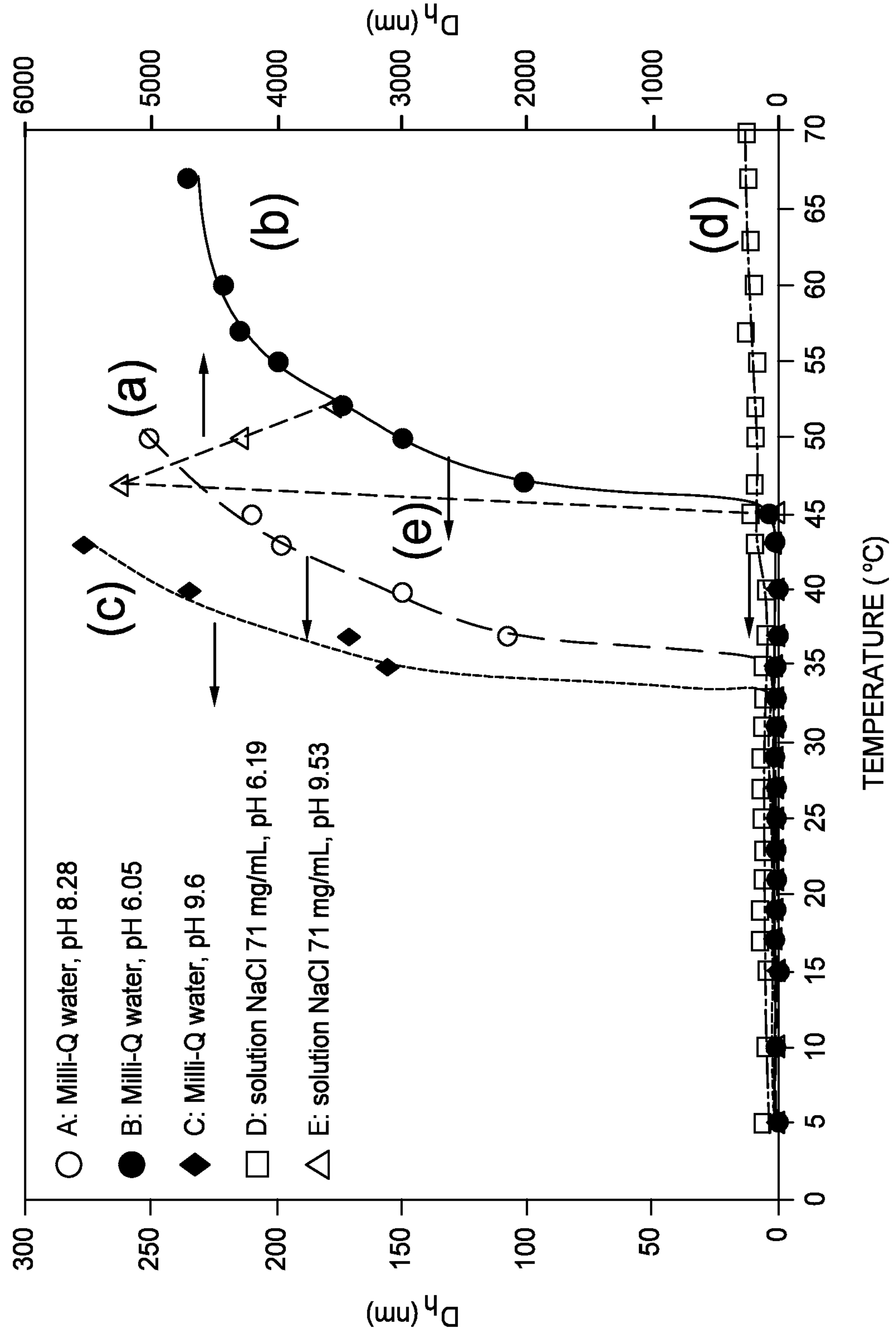
FIG. 9 shows examples of LCST profiles of a macroCTA after quaternization with iodomethane and iodooctane at different pHs according to certain aspects.

FIG. 9 shows examples of LCST profiles of MacroCTA-B (10 mg/mL) after quaternization with iodomethane (50%) and iodooctane (50%) at different pHs in Milli-Q water or sodium chloride (NaCl) solution according to certain aspects: (a) Milli-Q water (pH=8.28; LCST=35° C.); (b) Milli-Q water (pH=6.05; LCST=45° C.); (c) Milli-Q water (pH=9.60; LCST=33° C.); (d) NaCl solution (71 mg/mL, pH=6.19; no observable LCST in the temperature range studied); (e) NaCl solution (71 mg/mL, pH=9.53, LCST=45° C.).

To test the change in polymer conformation for the quaternized MacroCTA-B with 50% methane and 50% octane, the LCST was determined by changing both the pH and salt amounts. Curve (a) represents a solution of the MacroCTA-B dissolved in Milli-Q water, which gave a pH value of 8.28, and its LCST was determined to be 35° C. Adjusting the pH to 6.05 using HCl gave a higher LCST of 45° C.; while increasing the pH to 9.6 with NaOH decreased the LCST to 33° C. The addition of salt (NaCl) at dose to the salt amounts found in artificial body fluids showed that there was no observable LCST at a pH of 6.19, but with an increase in the pH to 9.53 an LCST was observed at 45° C. The data showed that salt increased the LCST while a pH increase led to a decrease in LCST.

TDMT Method to Produce Nanoworms

The molecular weight of the copolymers of the macroCTAs and polystyrene (PSTY) were determined by SEC and NMR. It can be seen from TABLE 6 that the copolymer were well controlled with the polystyrene consisted of between 45 to 48 units when the polymerization was repeated 3 times. The initial size of the nanospheres at 70° C., that is before its change at a lower temperature to transform to the nanoworms, was found to range from 163 to 215 nm and with a very narrow particle size distribution (PDIDLS<<0.1). Cooling these emulsion from 70 to eventually 10° C. reproducibly produced nanoworms as confirmed by TEM micrographs. The nanoworms as shown in Scheme 1A consisted of alkyne end-groups that could be further coupled with a wide range of molecules and polymers. TEM images of nanoworms made by TDMT method from latex spheres obtained by RAFT emulsion polymerization of styrene using MacroCTA-A (40 wt %) and MacroCTA-B (60 wt %). Three replicate polymerizations to check reproducibility,

TABLE 6

| Nanoworm | Conv. % | Dh (nm) | DLS PDI | Mn | SEC Đ | $N_{STY}$ | NMR Mn |
|---|---|---|---|---|---|---|---|
| NW Ex. 1 | 82 | 215 | 0.011 | 23571 | 1.55 | 46 | 12619 |
| NW Ex. 1 | 80 | 188 | 0.049 | 23673 | 1.39 | 45 | 12515 |
| NW Ex. 1 | 86 | 163 | 0.047 | 23098 | 1.39 | 48 | 12827 |

Post modification of nanoworms with either or both iodo-compounds (i.e. iodomethane and iodooctane) and the integrin binding peptide GRGD.

The nanoworms above were modified with various ratios of methane and octane groups with and without GRGD (see TABLE 7). The Zeta-potential for all the nanoworms (i.e. Nanoworm Examples) were generally greater than +30 mV, the only exception is Nanoworm Example 1 which represents the initial nanoworms before modification. The post modification did not after the nanoworm structure.

TABLE 7

| Nanoworm | Description | Zeta-potential (mV) |
|---|---|---|
| NW Ex. 1 | Alkyne PDMAEMA worms | +3.04 |
| NW Ex. 2 | GRGD PDMAEMA worms | +29.8 |
| NW Ex. 3 | Alkyne PDMAEMA worms quaternized with iodomethane | +45.9 |
| NW Ex. 4 | Alkyne PDMAEMA worms quaternized with iodooctane (10%), iodomethane (90%) | +39.3 |
| NW Ex. 5 | GRGD PDMAEMA worms quaternized with iodomethane | +36.2 |
| NW Ex. 6 | GRGD PDMAEMA worms quaternized with iodooctane (10%), iodomethane (90%) | +32.2 |
| NW Ex. 7 | Alkyne PDMAEMA worms quaternized with iodooctane (10%), iodomethane (90%) | +39.6 |
| NW Ex. 8 | Alkyne PDMAEMA worms quaternized with iodooctane (30%), iodomethane (70%) | +40.8 |
| NW Ex. 9 | Alkyne PDMAEMA worms quaternized with iodooctane (50%), iodomethane (50%) | +37.8 |
| NW Ex. 10 | Alkyne PDMAEMA worms quaternized with iodooctane (70%), iodomethane (30%) | +42.9 |
| NW Ex. 11 | Alkyne PDMAEMA worms quaternized with iodooctane (90%), iodomethane (10%) | +40.0 |
| NW Ex. 12 | GRGD PDMAEMA worms quaternized with iodooctane (10%), iodomethane (90%) | +38.1 |
| NW Ex. 13 | GRGD PDMAEMA worms quaternized with iodooctane (30%), iodomethane (70%) | +34.9 |
| NW Ex. 14 | GRGD PDMAEMA worms quaternized with iodooctane (50%), iodomethane (50%) | +35.3 |
| NW Ex. 15 | GRGD PDMAEMA worms quaternized with iodooctane (70%), iodomethane (30%) | +33.5 |
| NW Ex. 16 | GRGD PDMAEMA worms quaternized with iodooctane (90%), iodomethane (10%) | +37.1 |

Surface Wettability

Deposition of Nanoworms onto Glass Surfaces by Spin-Coating:

Prior spin-coating, glass surfaces were cleaned by 'piranha' solution (H2SO4+H2O2) and then washed five times in 70% ethanol solution. The surfaces were prepared by spin coating a nanoworm aqueous solution onto a glass surface. 100 microliters (μL) of a nanoworm aqueous solution (5 mg/mL) was added onto a dry glass surface and spin-coated at 2000 rpm over 60 sec with spin acceleration of 400 rpm/sec. Then, spin-coated surfaces were dried at an ambient temperature for 10 h.

Surface Wettability Test Using a Concentrated Salt Solution at 23° C.:

10 μL of salt solution at 23° C. (71 mg/mL sodium chloride in Milli-Q water, pH 6.5) was placed on a tested surface at 23° C. and video of droplet behavior on a surface was recorded for 1 min. This salt solution has a similar salt content and pH to that of artificial saliva.

To check how the pH of this salt solution affects wetting on a surface, 4 salt solutions (71 mg/mL sodium chloride in Milli-Q water, 0.04 mg/mL orange II sodium salt) were prepared at different pH values: 6.25, 7.60, 8.35 and 9.30. Then, 5 μL of these salt solutions at 23° C. was placed on a tested surface at 23° C. and the droplet behavior on a surface was observed.

Surface Wettability Test Using an Artificial Saliva Solution at 50° C.:

10 μL of the salt solution at 50° C. (71 mg/mL sodium chloride in Milli-Q water, pH 6.5) was placed on a tested surface at 23° C. and the droplet behavior on a surface observed.

Surface Wettability Test Using Milli-Q Water (Contained 0.04 mg/mL Orange II Sodium Salt) at Different pH at 23° C.:

5 μL of Milli-Q water at pH 5.95 was placed on a nanoworm coated surface at 23° C. and the droplet behavior on a surface was observed. The same procedure was repeated on the nanoworm coated surfaces using Milli-Q water with pH 7.29, 8.75 or 9.96.

Surface Wettability Test Using Milli-Q Water (Contained 0.04 mg/mL Orange II Sodium Salt) at Different pH at 37° C.:

5 μL of Milli-Q water at pH 5.95 at 37° C. was placed on a tested surface at 37° C. and the droplet behavior on the nanoworm coated surface was observed. The same procedure was repeated using Milli-Q water at pH 7.29, 8.75 or 9.96.

Surface Wettability Results:

Glass surfaces were first cleaned using a piranha solution and then spin coated with the nanoworms from TABLE 7, A droplet of water with or without NaCl (close to the salt found in artificial body fluid) at either 23 or 50° C. was dropped onto the nanoworm coated slides (at 23° C.). The slides coated with Nanoworm Example 1 were first tested with a NaCl droplet at either 23 or 50° C. The droplets wet rapidly across the surface after only a few seconds regardless of the droplet temperature with photos taken after 60 seconds, suggesting that the droplet temperature on the surface rapidly equilibrates to ambient temperature (in this case 23° C.). When the droplets without and with NaCl (71 mg/mL) were placed on the coated surfaces there were rapid wetting across the surface. In the case where the droplet temperature and surface temperature were at 37° C. in pure water, there was no observable wetting after 60 seconds, demonstrating that the surface was water-insoluble. When Nanoworm Example 3 and Nanoworm Example 4 were coated on the slides, the greater the content of octane groups in the nanoworm resulted in a lower LCST and thus a water-insoluble surface under these conditions. Taken together, the data demonstrated the ability of the surface to be designed to be highly water-soluble or water-insoluble under various environmental conditions. The rapid wetting demonstrates that under many types of conditions (similar to that of artificial body fluid), the microbes will have a greater opportunity to be captured in comparison to current antimicrobial surfaces.

Nanoworms Antibacterial Properties

The following protocol was used to test nanoworm coated surfaces against *E. coli*. Culture *E. coli* to OD (600 nm)=0.2, take 100 microliters (μL) centrifuge at 8000×g, 4° C., 5 min. Resuspend the pellet into 900 μL of PBS with the pellet fully resuspended by vortex at maximum speed for 3 min. Dilute the above solution to 1000 times dilution, Take 10 μL of the diluted *E. coli* and add it onto polymer coated coverslip surface. Incubate at RT for 3 h. Transfer the coverslip into a tube containing 300 μL PBS and incubate at room temperature for 5 min. Vortex the tube for 5 s at low power (eg. 1-2 speed). Transfer the 300 μL PBS to a new Eppendorf 1.5 mL tube. Vortex briefly of the 1.5 mL tube and take 60 μL of the solution onto a LB agar plate (containing kanamycin, 50 μg/mL). Culture the plate at 37° C. overnight. Count the clones on the plate.

Figure 10:
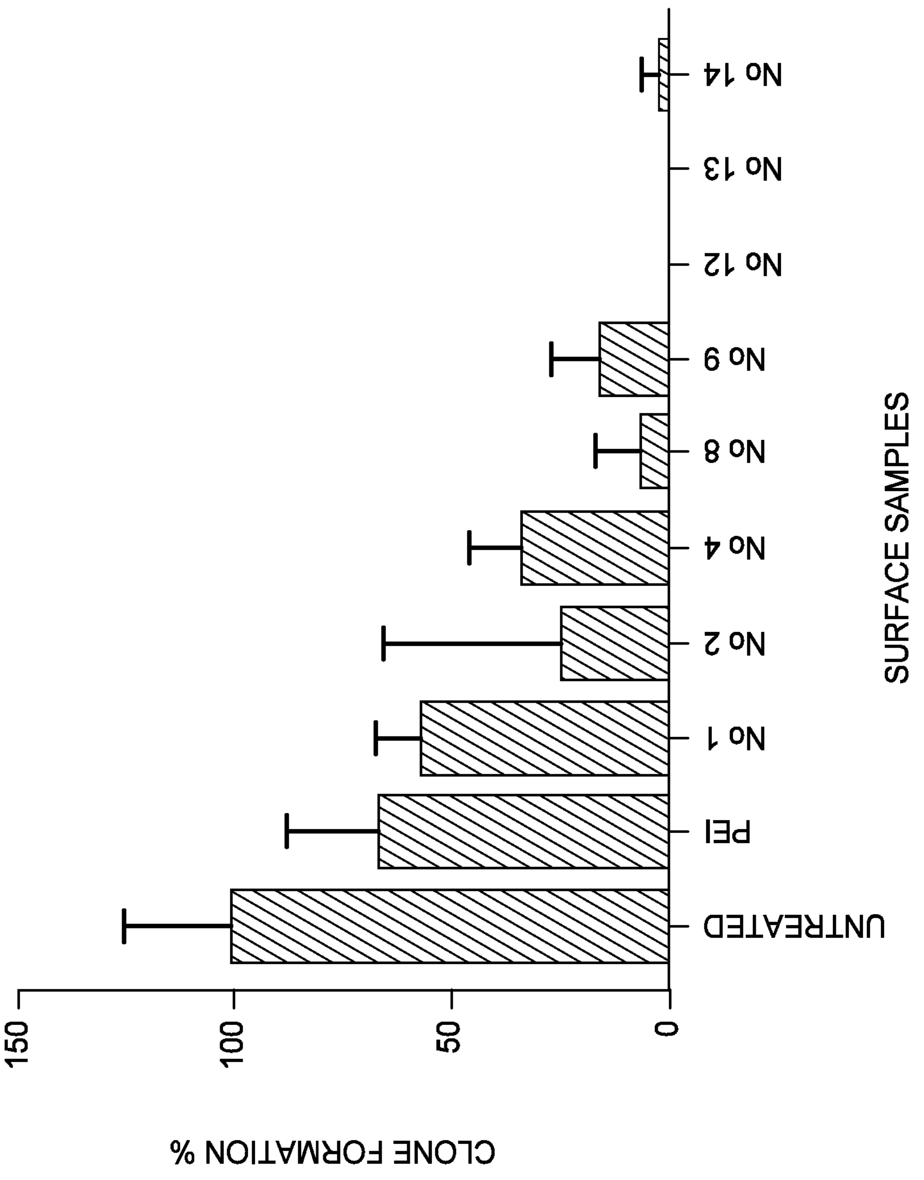
FIG. 10 shows examples of antibacterial activity against *E. coil* for nanoworm coated glass surfaces according to certain aspects.

FIG. 10 shows examples of antibacterial activity against *E. coli* for nanoworm coated glass surfaces according to certain aspects. For each surface, three replicates were performed. The surfaces are as follows: untreated corresponds to a bare glass surface; PEI corresponds to a glass surface coated with PEI (Mn 1800); No1 corresponds to a glass surface coated with Nanoworm Example 1; No2 corresponds to a glass surface coated with Nanoworm Example 2 (GRGD PDMAEMA worms); No4 corresponds to a glass surface coated with Nanoworm Example 4; No8 corresponds to a glass surface coated with Nanoworm Example 8; No9 corresponds to a glass surface coated with Nanoworm Example 9; No12 corresponds to a glass surface coated with Nanoworm Example 12; No13 corresponds to a glass surface coated with Nanoworm Example 13; and No14 corresponds to a glass surface coated with Nanoworm Example 14.

The glass slips were coated with a range of nanoworms from TABLE 7 and tested for their antibacterial (*E. coli*) behavior. To determine the killing efficiency of the nanoworm surfaces, a control surface of PEI was used and was set to approximately 40% killing efficiency. PEI is known to rapidly and effectively kill *E. coli*. The Nanoworm Examples 1, 2, 4, 8, 9, 12, 13, and 14 tested gave greater killing than PEI. The surface coated with Nanoworm Example 1 which had a low positive Zeta-potential gave about 45% killing efficiency. When GRGD was attached (Nanoworm Example 2) the killing efficiency increased in comparison to Nanoworm Example 1 to about 75% efficiency. The nanoworms functionalized with methyl and octyl groups had increased killing efficiency in comparison to Nanoworm Example 1. The Nanoworm Example 12, Nanoworm Example 13, Nanoworm Example 14 with both GRGD groups and alkyl groups provided killing efficiencies close to 100%.

Alkyne-γ-Thiolactone PDMAEMA Based Nanoworms

Synthesis of Alkyne-γ-Thiolactone PDMAEMA Nanoworms

In a Schlenk tube, Non-functional $PNIPAM_{44}$-S(C═S)$SC_4H_9$ (30 wt. %, 0.8077 g, $1.51\times10^{-4}$ mol), γ-thiolactone P($NIPAM_{43}$-co-$DMA_{20}$)-S(C═S)$SC_4H_9$ (10 wt. %, 0.2692 g, $3.74\times10^{-5}$ mol), alkyne (P($NIPAM_{50}$-co-$DMAEMA_{35}$)-S(C═S)$SC_4H_9$ (60 wt. %, 1.6154 g, $1.55\times10^{-4}$ mol) and SDS (0.1115 g, $3.87\times10^{-4}$ mol) were dissolved in degassed cold Milli-Q water (50 mL), 0.202 mL of styrene ($1.76\times10^{-3}$ mol) was added via syringe and the mixture was deoxygenated by purging with Argon for 1 h. AIBN (0.0056 g, $3.43\times10^{-5}$ mol) was dissolved in styrene (2 mL, 1.818 g, $1.75\times10^{-2}$ mol) and the solution was injected into the MacroCTAs mixture, which was then purged with Argon for another 25 min in an ice bath before heating to 70° C. The polymerization was stopped after 5 h by exposing the reaction to air at 70° C.

FIG. 14 shows a schematic view illustrating the synthesized alkyne-γ-thiolactone PDMAEMA nanoworm 1400. The polyalkene and the MacroCTA polymer units form a core 1410. The functional $R^1$ groups at the end of the MacroCTAs form macroCTA hairs 1420 extending from the core and located any position along the core. For example, the alkyne $R^1$ groups of the alkyne (P($NIPAM_{50}$-co-$DMAEMA_{35}$)-S(C═S)$SC_4H_9$ MacroCTA extend from the core 1410. For example, the γ-thiolactone $R^1$ groups of the γ-thiolactone P($NIPAM_{43}$-co-$DMA_{20}$)-S(C═S)$SC_4H_9$ MacroCTA extend from the core 1410.

Quaternization of Alkyne-γ-Thiolactone PDMAEMA Nanoworms

Quaternization with 10% Equivalence of Iodooctane

Alkyne-γ-thiolactone PDMAEMA nanoworms (1.6 g, $1.83\times10^{-3}$ mol of DMAEMA groups) of FIG. 14 were redispersed in 25 mL of Milli-Q water. Iodooctane (33 μL, 0.044 g, $1.83\times10^{-4}$ mol) was dissolved in 4.41 mL of DMSO. The solution of iodooctane in DMSO was added to alkyne-γ-thiolactone PDMAEMA nanoworms dispersion and the reaction mixture was shaken at 23° C. for 19 h. After that the reaction mixture was dialyzed against 0.01 M of sodium thiosulfate solution (3500 MWCO, 3×1 L, change every 4 h) followed by dialysis against Milli-Q water (3500 MWCO, 3×1 L, change every 4 h). The reaction mixture was freeze dried to isolate product as a white powder.

Figure 15A:
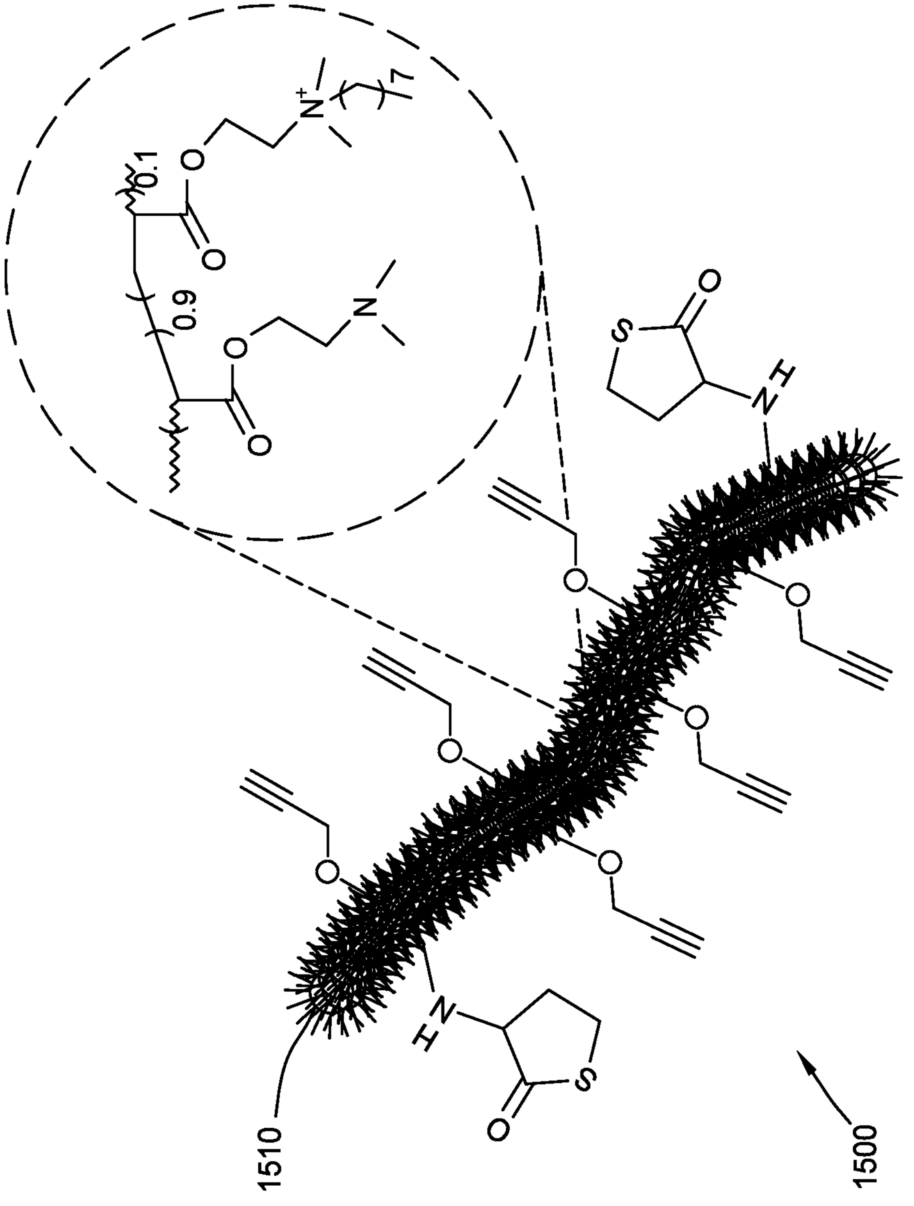
FIG. 15A shows a schematic view illustrating a synthesized alkyne-γ-thiolactone PDMAEMA nanoworm quaternized with 10% equivalence of iodooctane.

FIG. 15A shows a schematic view illustrating a synthesized alkyne-γ-thiolactone PDMAEMA nanoworm 1500 quaternized with 10% equivalence of iodooctane. It is estimated about 10% of the tertiary amine groups of the PDMAEMA polymer units of the core 1510 are quaternized with octyl groups.

Quaternization with 10% Equivalence of Iodooctane and 90% Equivalence of Iodomethane Alkyne-γ-thiolactone PDMAEMA nanoworms (1.96 g, $2.05\times10^{-3}$ mol of DMAEMA groups) of FIG. 14 were redispersed in 25 mL of Milli-Q water. Iodooctane (37 μL, 0.049 g, $2.05\times10^{-4}$ mol) was dissolved in 4.38 mL of DMSO. The solution of iodooctane in DMSO was added to alkyne-γ-thiolactone PDMAEMA nanoworms dispersion and the reaction mixture was shaken at 23° C. for 9 h. After that iodomethane (115 μL, 0.261 g, $1.84\times10^{-3}$ mol) was added to the reaction mixture and the reaction was carried out for extra 15 h at 23° C. After that the reaction mixture was dialyzed against 0.01 M of sodium thiosulfate solution (3500 MWCO, 3×1 L, change every 4 h) followed by dialysis against Milli-Q water (3500 MWCO, 3×1 L, change every 4 h). The reaction mixture was freeze dried to isolate product as a white powder.

Figure 15B:
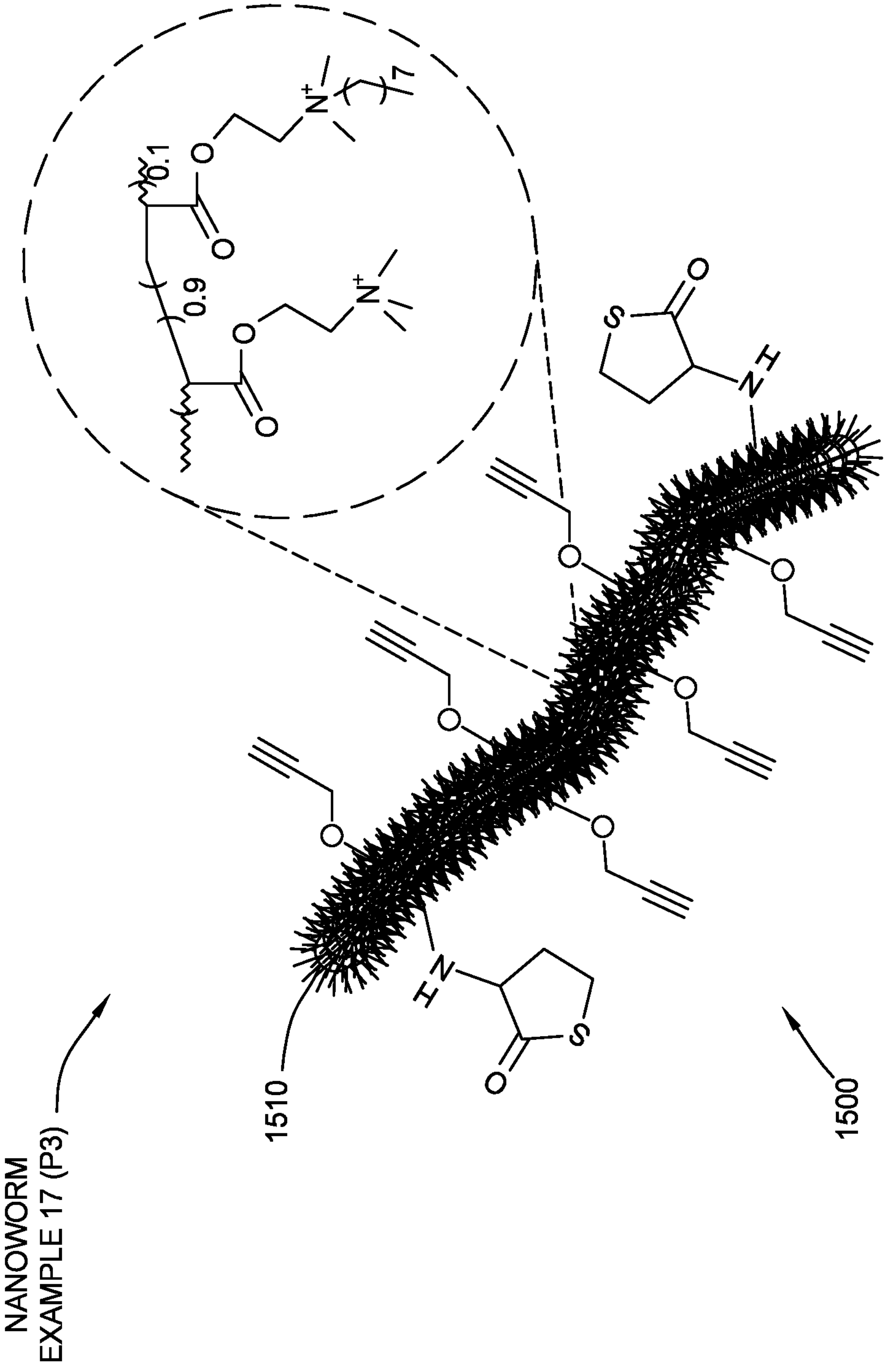
FIG. 15B shows a schematic view illustrating a synthesized alkyne-γ-thiolactone PDMAEMA nanoworm quaternized with 10% equivalence of iodooctane and 90% equivalence of iodomethane.

FIG. 15B shows a schematic view illustrating a synthesized alkyne-γ-thiolactone PDMAEMA nanoworm 1500 quaternized with 10% equivalence of iodooctane and 90% equivalence of iodomethane. It is estimated about 10% of the tertiary amine groups of the PDMAEMA polymer units of the core 1510 are quaternized with octyl groups and about 90% of the tertiary amine groups of the PDMAEMA polymer units of the core 1510 are quaternized with methyl groups. The nanoworms 1600 correspond to Nanoworm Example 17 (P3).

Quaternization with 100% Equivalence of Propargyl Bromide

Alkyne-γ-thiolactone PDMAEMA nanoworms (1.7084 g, 1.76×10−3 mol of DMAEMA groups) of FIG. 14 were redispersed in 20 mL of Milli-Q water. Propargyl bromide (80 wt. % in toluene, 196 μL, 0.209 g, 1.76×10−3 mol) was dissolved in 3.53 mL of DMSO. The solution of propargyl bromide in DMSO was added to alkyne-γ-thiolactone PDMAEMA nanoworms dispersion and the reaction mixture was shaken at 23° C. for 19 h. After that the reaction mixture was dialyzed against Milli-Q water (3500 MWCO, 5×1 L, change every 4 h). The reaction mixture was freeze dried to isolate product as a white powder.

Figure 15C:
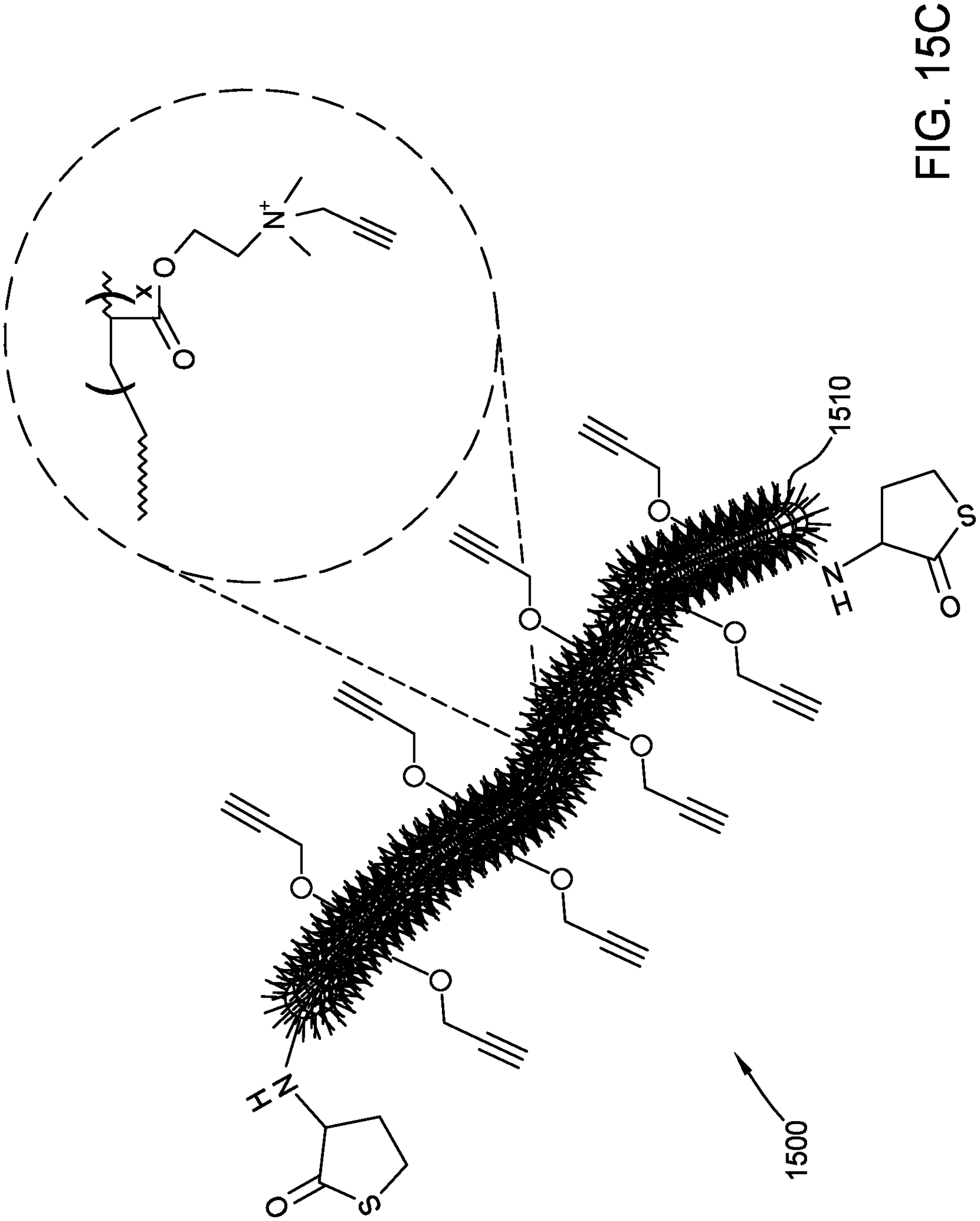
FIG. 15C shows a schematic view illustrating a synthesized alkyne-γ-thiolactone PDMAEMA nanoworm quaternized with equivalence of propargyl bromide.

FIG. 15C shows a schematic view illustrating a synthesized alkyne-γ-thiolactone PDMAEMA nanoworm 1500 quaternized with 100% equivalence of propargyl bromide. It is estimated about 100% of the tertiary amine groups of the PDMAEMA polymer units of the core 1510 are quaternized with propargyl groups.

Conjugation of Guanidine Azide to Quaternized Alkyne-γ-Thiolactone PDMAEMA Nanoworms via CuAAC Conjugation to Quaternized Alkyne-γ-Thiolactone PDMAEMA Nanoworms with about 10% of the Tertiary Amine Groups Quaternized with Octyl Groups Quaternized alkyne-γ-thiolactone PDMAEMA nanoworms with about 10% of the tertiary amine groups quaternized with octyl groups (1.485 g, 5.55×10−5 mol of alkyne groups) of FIG. 15A were dispersed in 20 mL of the degassed solution of Milli-Q water and DMSO (85%/15%, vv.). The solution of guanidine azide (0.0095 g, 6.66x10−5 mol) in 1 mL of the degassed solution of Milli-Q water and DMSO (85%/15%, vv.) was injected into nanoworms dispersion via a degassed syringe. 5 mL of ascorbic acid (0.0684 g, 3.88x10−4 mol) in the degassed solution of Milli-Q water and DMSO (85%/15%, vv.) was injected into nanoworms and guanidine azide dispersion via a degassed syringe. Then, 5 mL of CuSO4 (0.0265 g, 1.66x10−4 mol) in the degassed solution of Milli-Q water and DMSO (85%/15%, vv.) was injected into the reaction mixture via a degassed syringe. The reaction was carried out for 19 h at 23° C. under argon atmosphere. The reaction was stopped by exposure to the air and the suspension was dialysed against Milli-Q water for 36 h (3500 MWCO, 9x1 L, change every 4 h). The resulting solution was freeze-dried to obtain the product as a white powder.

Figure 16A:
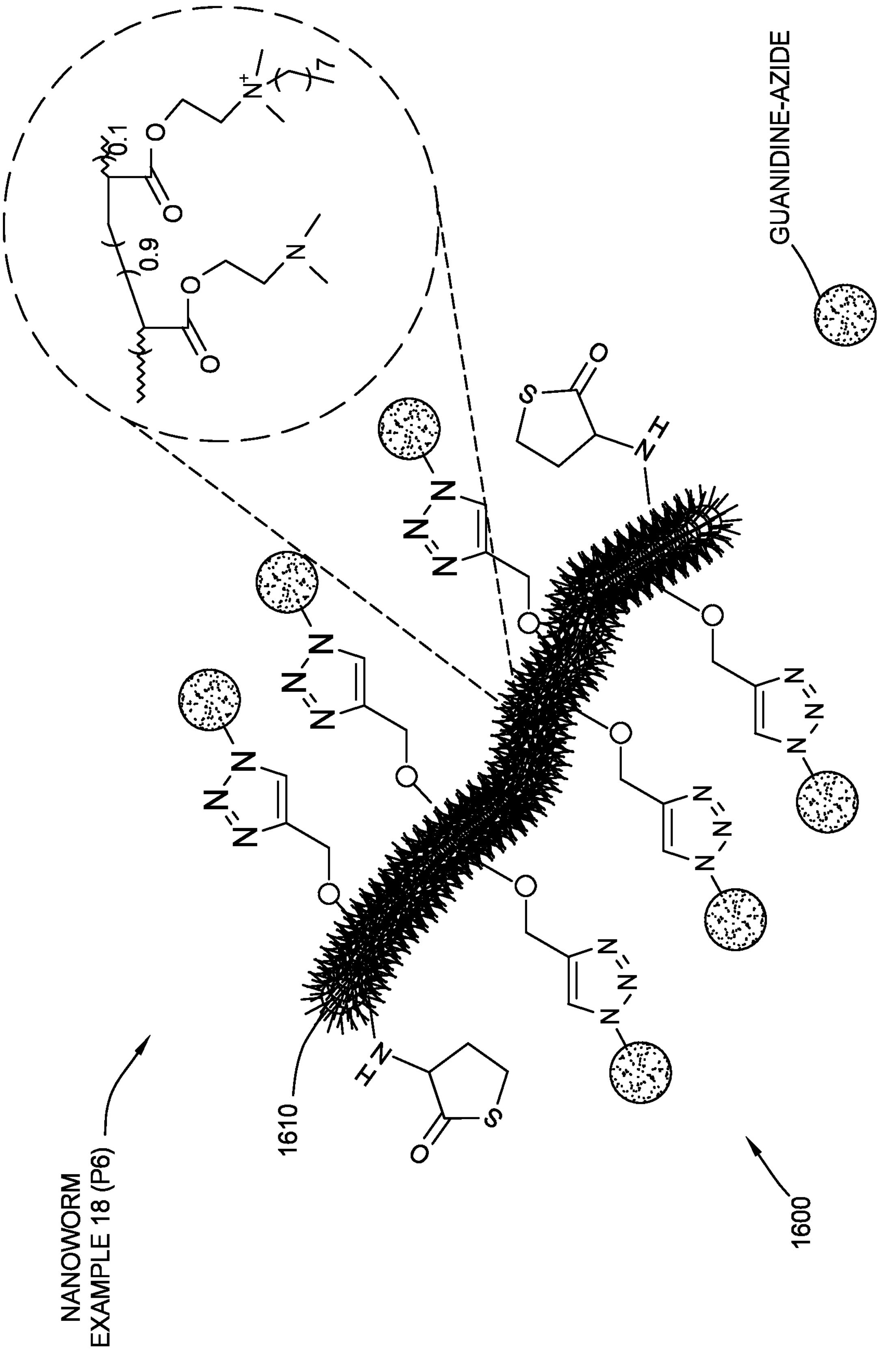
FIG. 16A shows a schematic view illustrating a synthesized conjugated guanidine azide to quaternized alkyne-γ-thiolactone PDMAEMA nanoworms with about 10% of the tertiary amine groups quaternized with octyl groups.

FIG. 16A shows a schematic view illustrating a synthesized conjugated guanidine azide to quaternized alkyne-γ-thiolactone PDMAEMA nanoworms 1600 with about 10% of the tertiary amine groups quaternized with octyl groups. The nanoworms 1600 correspond to Nanoworm Example 18 (P6).

Conjugation to Quaternized Alkyne-γ-Thiolactone PDMAEMA Nanoworms with about 10% of the Tertiary Amine Groups Quaternized with Octyl Groups and with about 90% of the Tertiary Amine Groups Quaternized with Methyl Groups.

Quaternized alkyne-γ-thiolactone PDMAEMA nanoworms (0.25 g, $8.47\times10^{-6}$ mol of alkyne groups) of FIG. 15B were dispersed in 10 mL of the degassed solution of Milli-Q water and DMSO (85%/15%, vv.). The solution of guanidine azide (0.0014 g, $1.02\times10^{-5}$ mol) in 1 mL of the degassed solution of Milli-Q water and DMSO (85%/15%, vv.) was injected into nanoworms dispersion via a degassed syringe. 2 mL of ascorbic acid (0.0104 g, $5.93\times10^{-5}$ mol) in the degassed solution of Milli-Q water and DMSO (85%/15%, vv.) was injected into nanoworms and guanidine azide dispersion via a degassed syringe. Then, 2 mL of $CuSO_4$ (0.0041 g, $2.54\times10^{-5}$ mol) in the degassed solution of Milli-Q water and DMSO (85%/15%, vv.) was injected into the reaction mixture via a degassed syringe. The reaction was carried out for 19 h at 23° C. under argon atmosphere. The reaction was stopped by exposure to the air and the suspension was dialysed against Milli-Q water for 36 h (3500 MWCO, 9x1 L, change every 4 h). The resulting solution was freeze-dried to obtain the product as a white powder.

Figure 16B:
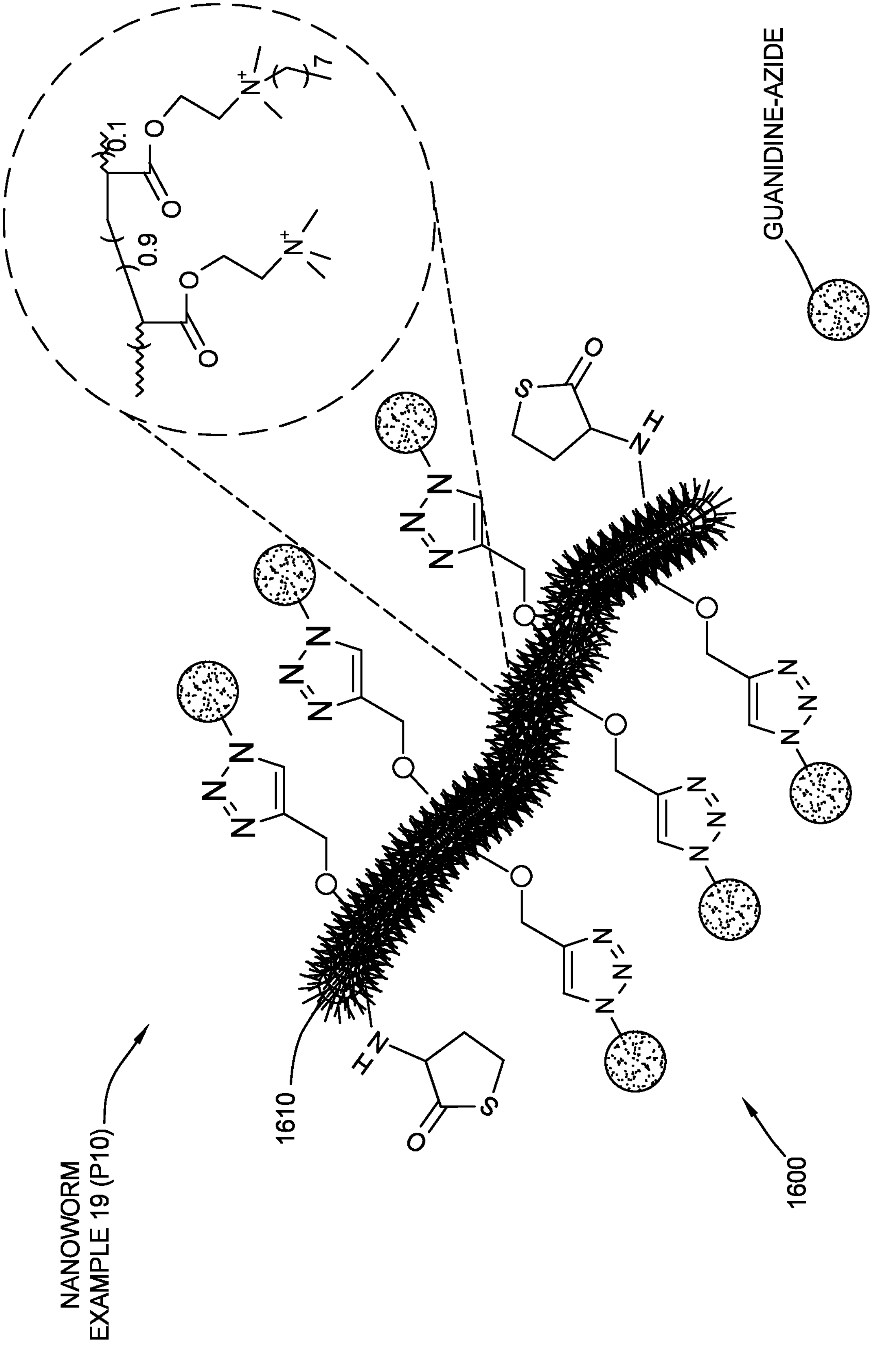
FIG. 16B shows a schematic view illustrating a synthesized conjugated guanidine azide to quaternized alkyne-γ-thiolactone PDMAEMA nanoworms with about 10% of the tertiary amine groups quaternized with octyl groups and with about 90% of the tertiary amine groups quaternized with methyl groups.

FIG. 16B shows a schematic view illustrating the synthesized conjugated guanidine azide to quaternized alkyne-γ-thiolactone PDMAEMA nanoworms 1600 with about 10% of the tertiary amine groups quaternized with octyl groups and with about 90% of the tertiary amine groups quaternized with methyl groups. The nanoworms 1600 correspond to Nanoworm Example 19 (P10), P(NIPAM-co-DMAEMA)-$N_3$ Based Nanoworms Synthesis of P($NIPAM_{55}$-co-$DMAEMA_{48}$) by Single-Electron Transfer Living Radical Polymerization A macroCTA of a copolymer of NIPAM and DMAEMA was synthesized by single-electron transfer living radical polymerization according to reaction scheme (VIII).

(VII)

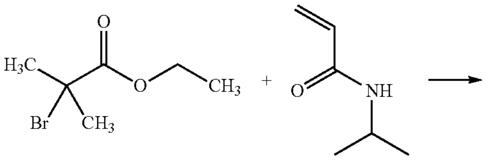

-continued

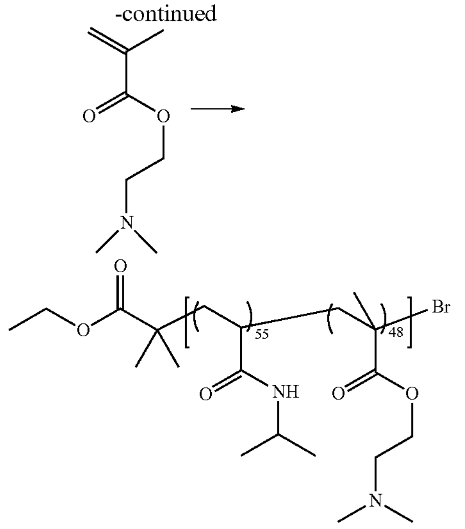

To a 10 mL Schlenk tube equipped with magnetic stirrer, Cu(II)$Br_2$ (0.0197 g, $8.84\times10^{-5}$ mol) and $NaBH_4$ (0.0033 g, $8.84\times10^{-5}$ mol) were added. The flask was sealed with a rubber septum and purged with Ar for 30 min. To a 5 mL glass vial, $Me_6$TREN (24 μL, 0.02 g, $8.84\times10^{-5}$ mol) and Milli-Q water (2.564 mL) were added; the vial sealed, and the solution purged with Ar for 30 min. This solution was cannula transferred to the Cu(II)$Br_2$/$NaBH_4$ Schlenk tube and placed in an ice-bath where the reduction of $Cu^{II}$ was allowed to proceed for 30 min. Another mixture of NIPAM (1 g, $8.84\times10^{-3}$ mol), DMAEMA (0.893 mL, 0.833 g, $5.30\times10^{-3}$ mol) and the initiator EBiB (16 μL, 0.0215 g, $1.10\times10^{-4}$ mol) were dissolved in isopropanol (2.564 mL) in a 5 mL glass vial, sealed, purged with Ar for 30 min at 0° C., and then cannula transferred to the polymerization Schenk tube. The polymerization was carried out at 0° C. for 90 min.

Synthesis of P($NIPAM_{55}$-co-$DMAEMA_{48}$)-$N_3$

A macroCTA of P($NIPAM_{55}$-co-$DMAEMA_{48}$)-$N_3$ was synthesized according to reaction scheme (IX).

(IX)

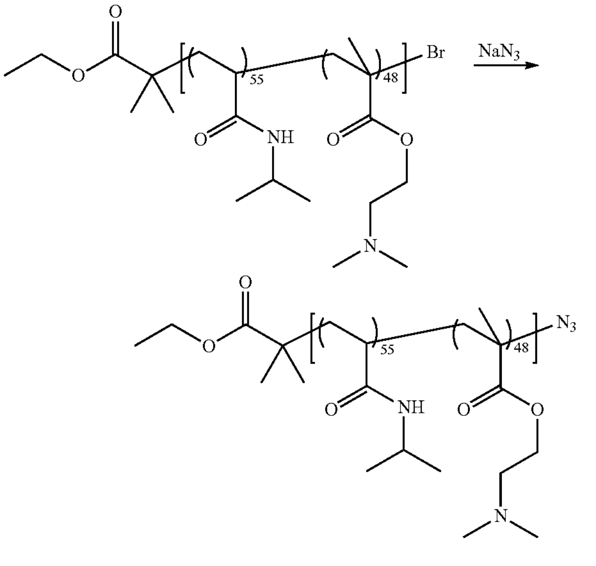

20 eq. of $NaN_3$ in 2 mL of water was added to a polymerization mixture of reaction scheme (VIII), warmed to 25° C., and then left to stir overnight. The reaction mixture was then dialyzed against acetone (3x1 L, change every 3 h). The solution after dialysis was passed through activated basic alumina to remove copper salts. The solvent was removed by rotary evaporation, 5 mL of Milli-Q water was added, and the residual was freeze-dried to isolate the product as a white powder.

Quaternization of P($NIPAM_{55}$-co-$DMAEMA_{48}$)-$N_3$ with 10% Equivalence Iodooctane A macroCTA of a copolymer of NIPAM and DMAEMA was synthesized according to reaction scheme (X)

(X)

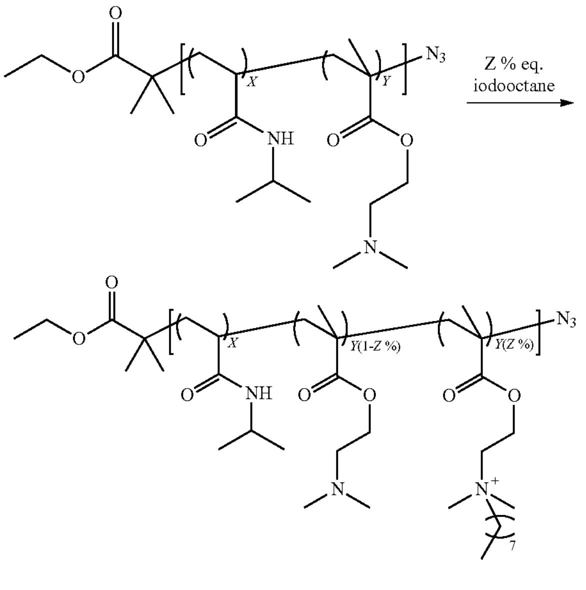

P($NIPAM_{55}$-co-$DMAEMA_{48}$)-$N_3$ (7.7178 g, $2.64\times10^{-2}$ mol of DMAEMA groups) was dissolved in 50 mL of DCM. Then, iodooctane (0.476 mL, 0.634 g, $2.64\times10^{-3}$ mol) was added and the reaction was carried out for 19 h at 23° C. After that the reaction mixture was dialyzed against 0.01 M of sodium thiosulfate solution (3500 MWCO, 3x1 L, change every 4 h) followed by dialysis against Milli-Q water (3500 MWCO, 3x1 L, change every 4 h). The reaction mixture was freeze dried to isolate product as a white powder. A quaternized ($NIPAM_{55}$-co-$DMAEMA_{48}$)-$N_3$ with octyl groups was formed according to reaction scheme (X) in which X was about 55, Y(1−Z %) was about 43.2, and Y(Z %) was about 4.8.

Grafting of Quaternized P(NIPAM-co-DMAEMA)-$N_3$ to Grafted Alkyne-γ-Thiolactone PDMAEMA Nanoworms Grafting of Quaternized P($NIPAM_{55}$-Co-$DMAEMA_{48}$)-$N_3$ to Alkyne-γ-Thiolactone PDMAEMA Nanoworms Via CuAAC Quaternized P($NIPAM_{55}$-co-$DMAEMA_{48}$)-$N_3$ (5.484 g, $3.75\times10^{-4}$ mol) with 10% equivalence of iodooctane (reaction product of Scheme X) was dissolved in 90 of the mixture of Milli-Q water/DMSO (85%/15%, vv.). Then, this solution was added to quaternized alkyne-γ-thiolactone PDMAEMA nanoworms quaternized with proparyl groups (0.5975 g, $6.25\times10^{-4}$ mol of alkyne groups) of FIG. 15C and the mixture was purged with argon for 3 h. 10 mL of ascorbic acid (0.7706 g, $4.38\times10^{-3}$ mol) in the degassed solution of Milli-Q water and DMSO (85%/15%, vv.) was injected into the reaction mixture via a degassed syringe. Then, 10 mL of $CuSO_4$ (0.2993 g, $1.88\times10^{-3}$ mol) in the degassed solution of Milli-Q water and DMSO (85%/15%, vv.) was injected into the reaction mixture via a degassed syringe. The reaction was carried out for 19 h at 23° C. under argon atmosphere. The reaction was stopped by exposure to the air and the suspension was dialysed against 0.01M of EDTA disodium salt (3500 MWCO, 3x1 L, change every 4 h) followed by dialysis against Milli-Q water for 36 h (3500 MWCO, 9x1 L, change every 4 h). The resulting solution was freeze-dried to obtain the product as a light blue powder.

Figure 17A:
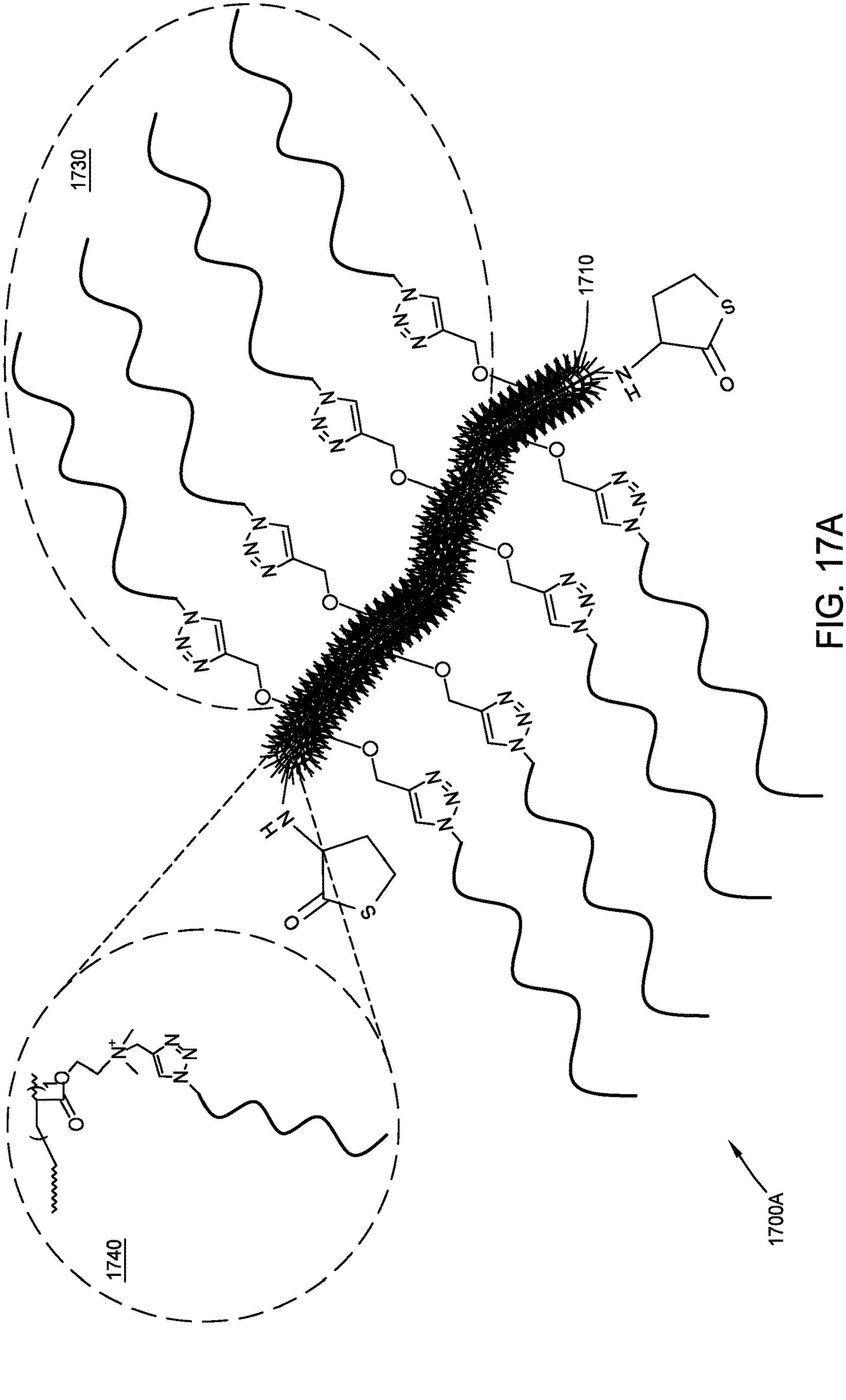
FIG. 17A shows a schematic view illustrating a quaternized P($NIPAM_{55}$-co-$DMAEMA_{48}$) grafted to an alkyne-γ-thiolactone PDMAEMA nanoworm.

FIG. 17A shows a schematic view illustrating a quaternized P($NIPAM_{55}$-co-$DMAEMA_{48}$) grafted to an alkyne-γ-thiolactone PDMAEMA nanoworm 1700A. The resulting nanoworm 1700A include a core 1710 comprising an alkyne-γ-thiolactone PDMAEMA nanoworm. A portion 1730 of the quaternized P($NIPAM_{55}$-co-$DMAEMA_{48}$)-$N_3$ are grafted to the alkyne $R^1$ groups of the alkyne-γ-thiolactone PDMAEMA nanoworm. A portion 1740 of the quaternized P($NIPAM_{55}$-co-$DMAEMA_{48}$)-$N_3$ are grafted to the alkyne groups of the propargyl groups of the quaternized alkyne-γ-thiolactone PDMAEMA nanoworm.

Quaternization of Grafted PDMAEMA Nanoworms with 30% Propargyl Bromide and Conjugation of Guanidine Azide to Quaternized Grafted Alkyne PDMAEMA Nanoworms Grafted PDMAEMA nanoworms (2.2759 g, $5.94\times10^{-3}$ mol of DMAEMA groups) of FIG. 17A were redispersed in 80 mL of Milli-Q water. Propargyl bromide (80 wt, % in toluene, 198 μL, 0.212 g, $1.78\times10^{-3}$ mol) was dissolved in 14.12 mL of DMSO. The solution of propargyl bromide in DMSO was added to grafted PDMAEMA nanoworms dispersion and the reaction mixture was stirred at 23° C. for 19 h. After that the reaction mixture was dialyzed against Milli-Q water (3500 MWCO, 6x1 L, change every 4 h). The reaction mixture was freeze dried to isolate product as a light blue powder.

Figure 17B:
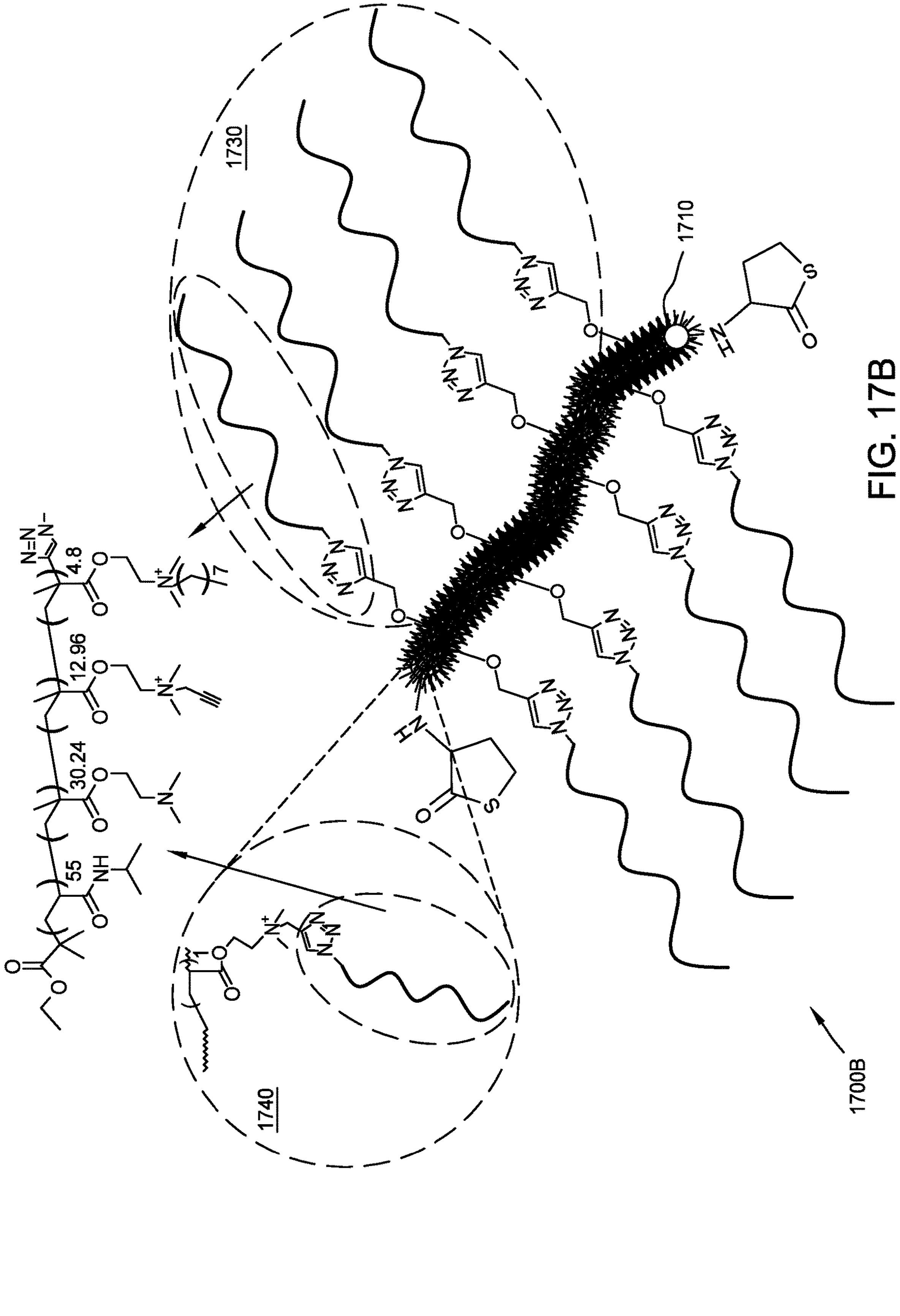
FIG. 17B shows a schematic view illustrating of a resulting P($NIPAM_{55}$-co-$DMAEMA_{48}$) grafted to an alkyne-γ-thiolactone PDMAEMA nanoworm.

FIG. 17B shows a schematic view illustrating of a resulting P($NIPAM_{55}$-co-$DMAEMA_{48}$) grafted to an alkyne-γ-thiolactone PDMAEMA nanoworm 1700B. The P($NIPAM_{55}$-co-$DMAEMA_{48}$) of portion 1730 and portion 1740 is quaternized with propargyl groups and with octyl groups. About 30% of the remaining tertiary amine groups Y(1−Z %) was quaternized with propargyl groups.

Quaternized grafted alkyne-γ-thiolactone PDMAEMA nanoworms (1.5067 g, $1.15\times10^{-3}$ mol of alkyne groups) of FIG. 17B were dispersed in 18 mL of the degassed solution of Milli-Q water and DMSO (85%/15%, vv.). The solution of guanidine azide (0.163 g, $1.15\times10^{-3}$ mol) in 2 mL of the degassed solution of Milli-Q water and DMSO (85%/15%, vv.) was injected into nanoworms dispersion via a degassed syringe. 10 mL of ascorbic acid (1.412 g, $8.02\times10^{-3}$ mol) in the degassed solution of Milli-Q water and DMSO (85%/15%, vv.) was injected into nanoworms and guanidine azide dispersion via a degassed syringe. Then, 10 mL of CuSO4 (0.5484 g, $3.44\times10^{-3}$ mol) in the degassed solution of Milli-Q water and DMSO (85%/15%, vv.) was injected into the reaction mixture via a degassed syringe. The reaction was carried out for 19 h at 23° C. under argon atmosphere. The reaction was stopped by exposure to the air and the suspension was dialysed against 0.01M of EDTA disodium salt (3500 MWCO, 3x1 L, change every 4 h) followed by dialysis against Milli-Q water for 36 h (3500 MWCO, 9x1 L, change every 4 h). The resulting solution was freeze-dried to obtain the product as a light green powder.

Figure 17C:
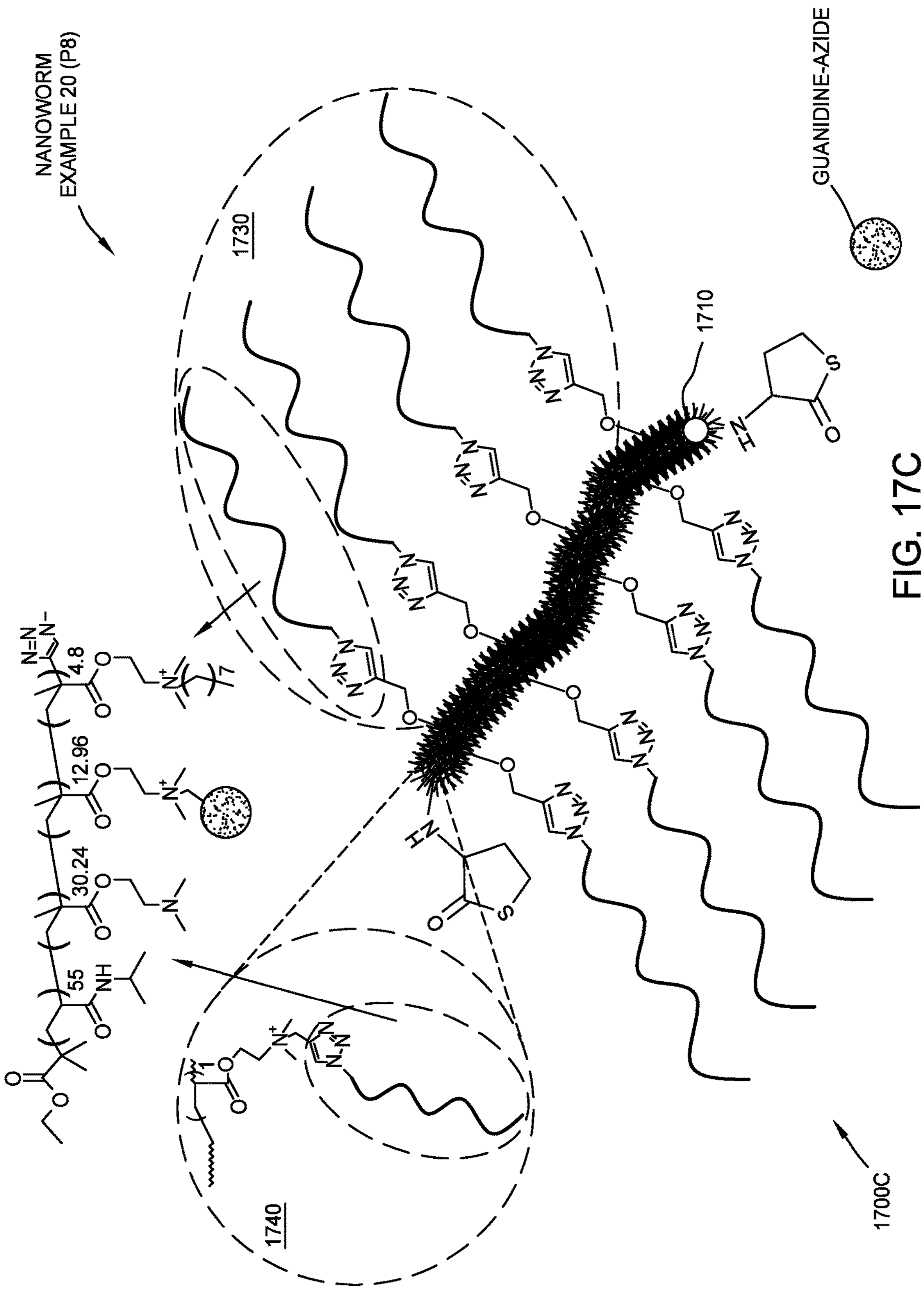
FIG. 17C shows a schematic view illustrating of a resulting conjugation of guanidine azide to quaternized grafted alkyne PDMAEMA nanoworms.

FIG. 17C shows a schematic view illustrating of a resulting conjugation of guanidine azide to quaternized grafted alkyne PDMAEMA nanoworms 1700C. Guanidine azide was conjugated to the propargyl groups of the P(NIPAM$_{55}$-co-DMAEMA$_{48}$) of portion 1730 and portion 1740. The nanoworms 1700C correspond to Nanoworm Example 20 (P8).

Quaternization of Grafted PDMAEMA Nanoworms with 50% Propargyl Bromide and Conjugation of Guanidine Azide to Quaternized Grafted Alkyne PDMAEMA Nanoworms Quaternized grafted alkyne PDMAEMA nanoworms similar to FIG. 17C were formed by quaternization of the about 50% of the remaining tertiary amine groups Y(1−Z %) was with propargyl groups and conjugation of guanidine azide to propargyl quaternized groups. These formed nanoworms correspond to Nanoworm Example 21 (P9)

Conjugation of Guanidine Azide and Polygalactose Azide to Quaternized Grafted Alkyne PDMAEMA Nanoworms.

Quaternized grafted alkyne-γ-thiolactone PDMAEMA nanoworms (0.5 g, $3.80\times10^{-4}$ mol of alkyne groups) of FIG. 17B were dispersed in 4 mL of the degassed solution of Milli-Q water and DMSO (85%/15%, vv.). A solution of guanidine azide (0.046 g, $3.23\times10^{-4}$ mol) in 1 mL of the degassed solution of Milli-Q water and DMSO (85%/15%, vv.) was injected into nanoworms dispersion via a degassed syringe. A solution of polygalactose azide (0.1558 g, $5.70\times10^{-5}$ mol) in 2 mL of the degassed solution of Milli-Q water and DMSO (85%/15%, vv.) was injected into nanoworms dispersion via a degassed syringe. 4 mL of ascorbic acid (0.4686 g, $2.66\times10^{-3}$ mol) solution in the degassed solution of Milli-Q water and DMSO (85%/15%, vv.) was injected into nanoworms, guanidine azide and polygalactose azide dispersion via a degassed syringe. Then, 4 mL of $CuSO_4$ (0.1820 g, $1.14\times10^{-3}$ mol) solution in the degassed solution of Milli-Q water and DMSO (85%/15%, vv.) was injected into the reaction mixture via a degassed syringe. The reaction was carried out for 19 h at 23° C. under argon atmosphere. The reaction was stopped by exposure to the air and the suspension was dialysed against 0.01M of EDTA disodium salt (3500 MWCO, 3x1 L, change every 2 h) followed by dialysis against Milli-Q water for 24 h (3500 MWCO, 6x1 L, change every 4 h). The resulting solution was freeze-dried to obtain the product as a light green powder.

Figure 17D:
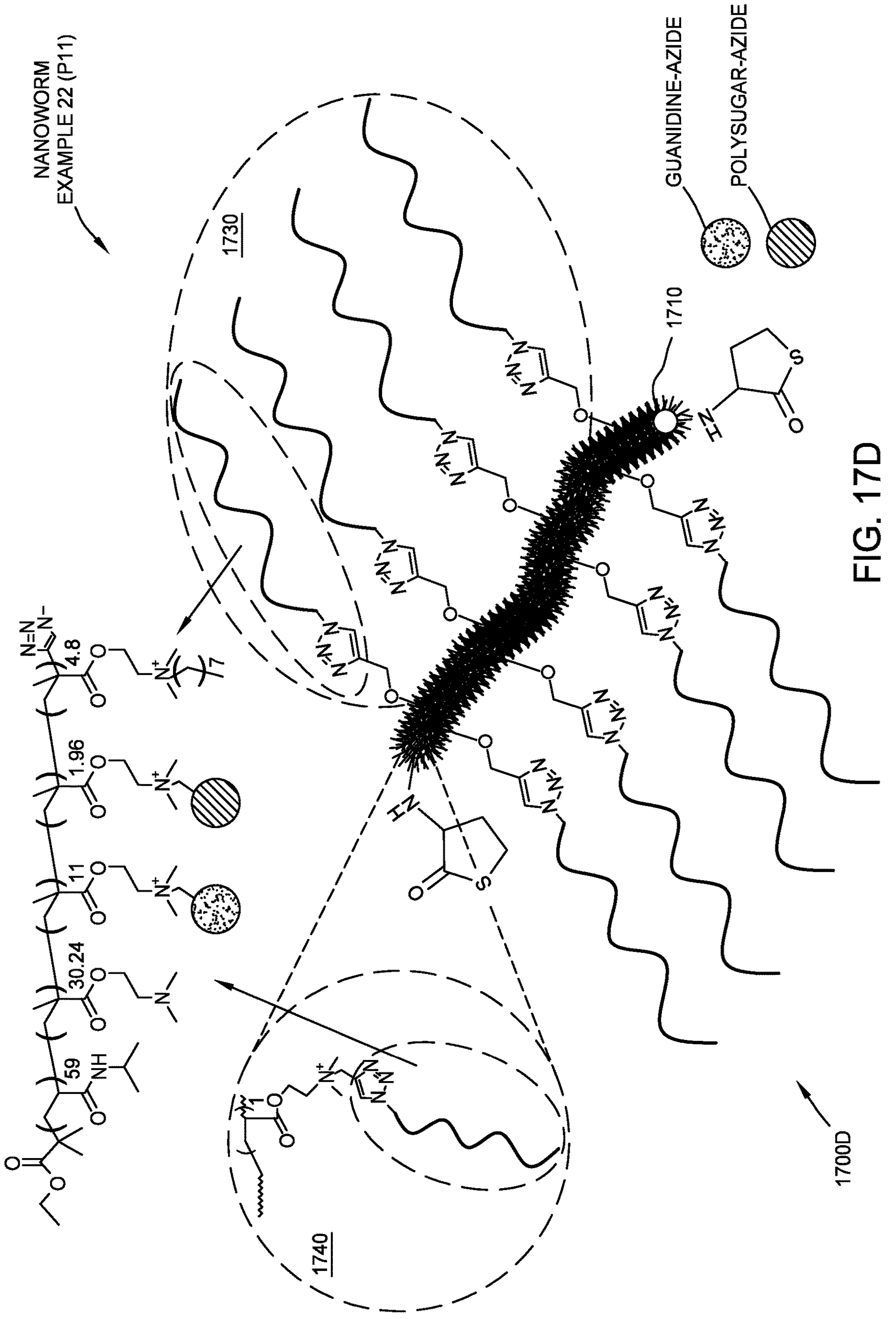
FIG. 17D shows a schematic view illustrating the resulting conjugation of guanidine azide and polygalactose azide to quaternized grafted alkyne PDMAEMA nanoworms.

FIG. 17D shows a schematic view illustrating the resulting conjugation of guanidine azide and polygalactose azide to quaternized grafted alkyne PDMAEMA nanoworms. Guanidine azide and polygalactose azide was conjugated to the propargyl groups of the P(NIPAM$_{55}$-co-DMAEMA$_{48}$) of portion 1730 and portion 1740. The nanoworms 1700D correspond to Nanoworm Example 22 (P11).

Preparation of Polygalactose Azide

Step. 1 SET-LRP of 6-O-acryloyl-1,2:3,4-di-O-isopropylidene-D-galactopyranose

Single-electron transfer living radical polymerization was performed according to the following reaction scheme (XI).

(XI)

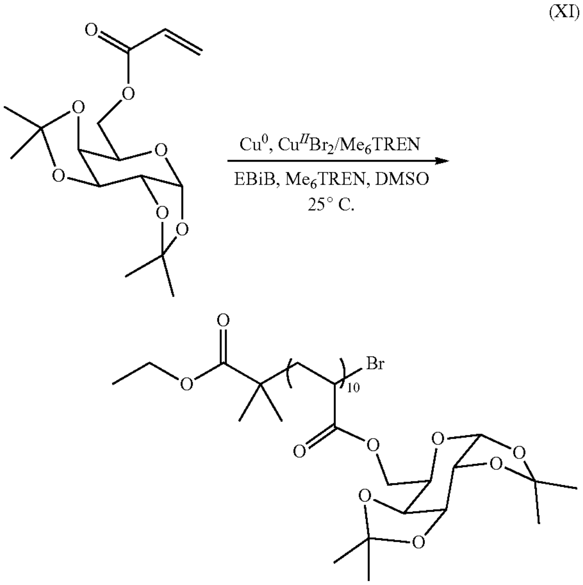

Protected sugar acrylate (0.5 g, $1.59\times10^{-3}$ mol), Me$_6$tren (4.3 μL, 0.0037 g, $1.59\times10^{-5}$ mol), CuBr$_2$/Me$_6$tren (0.0072 g, $1.59\times10^{-5}$ mol) and DMSO (1 mL) were added to a 4 mL vial, cooled down to 0° C. and purged with argon for 30 min to remove oxygen. Cu(0) powder (0.001 g, $1.59\times10^{-5}$ mol) was added to a 15 mL Schlenk tube and purged with argon for 30 min. Then, degassed solution of 1 mL of the initiator EBiB (23 μL, 0.031 g, $1.59\times10^{-4}$ mol) in DMSO was added to a 4 mL vial via a degassed syringe. The reaction mixture from a 4 mL vial was transferred to a Schlenk tube via a degassed syringe. A Schlenk tube was placed into a temperature controlled oil bath at 25° C. Samples for SEC were taken over time to monitor the reaction progress. The reaction was stopped after 4 h by quenching in liquid nitrogen. Then, 10 mL of acetone was added to redissolve reaction mixture and this solution was passed through basic alumina column. The column was washed a few times with acetone. Then, acetone was evaporated using a rotavap and the residue was used directly for azidation step.

Step 2. Azidation of Protected Polygalactose-Br

Azidation of protected polygalactose-Br was performed according to the following reaction scheme (XII).

(XII)

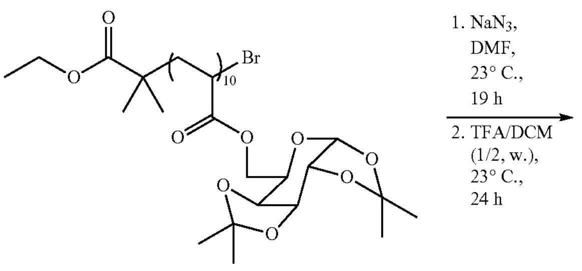

-continued

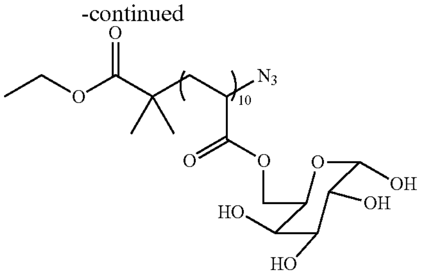

The polymer (0.35 g, $1.05\times10^{-4}$ mol) was dissolved in 15 mL of DMF. Then $NaN_3$ (0.1363 g. $2.10\times10^{-3}$ mol) was added to the polymer solution. The reaction was carried out for 19 h. DMF was removed by nitrogen flow overnight. The resulting mixture was redissolved in 12 mL of chloroform and the insoluble salts were filtered out. Chloroform was removed by nitrogen flow to yield a white powder as a product.

Step 3. Deprotection of Protected Polygalactose-$N_3$

The polymer (0.3 g, $1.8\times10^{-3}$ mol of acetal groups) was dissolved in 4 mL of DCM. Then, 2 mL of TFA (2.978 g, $2.6\times10^{-2}$ mol, 14.4 eq.) was added. The reaction was stirred for 24 h. After that the reaction mixture was dialyzed against acetone (2x500 mL). The acetone was removed by nitrogen flow and the residue was dried under high vacuum to give a brown solid as a product.

Nanoworms Antiviral Properties

Live H3N2 Influenza Virus

Figure 11:
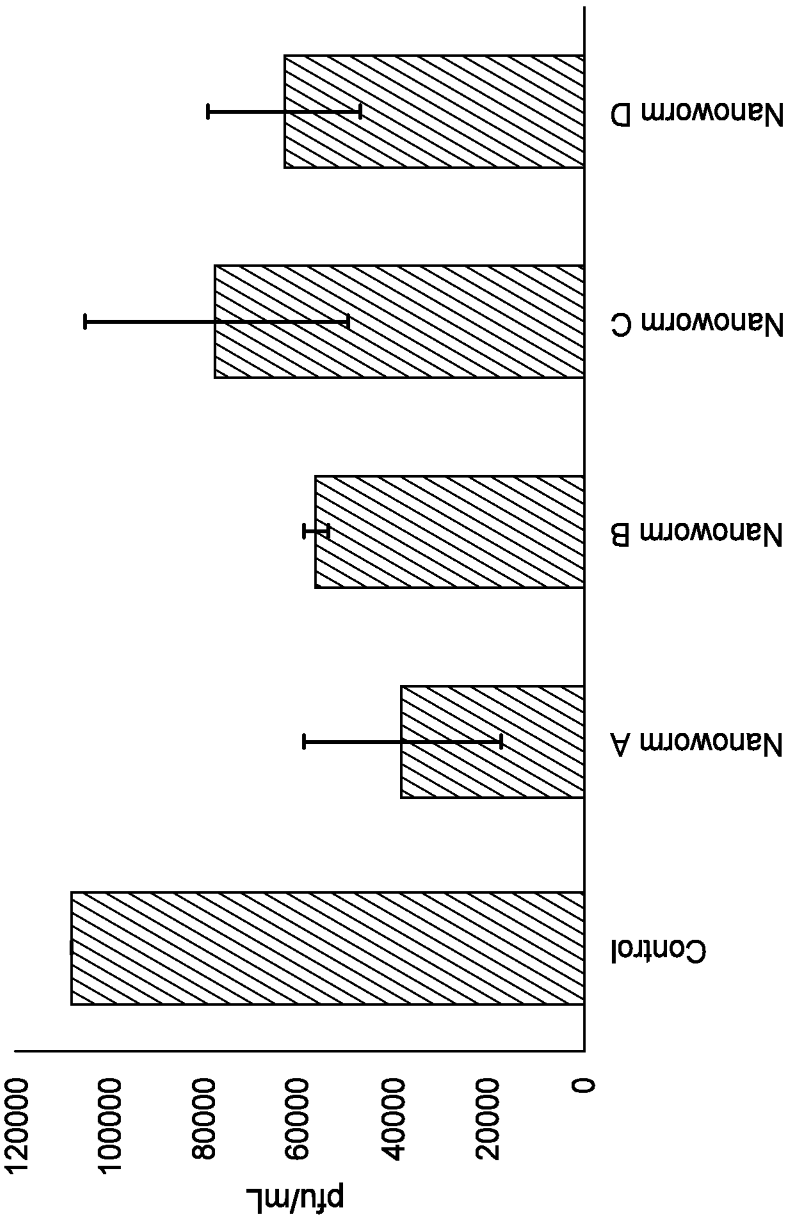
FIG. 11 shows examples of antiviral activity against H3N2 influenza virus for nanoworm coated surfaces according to certain aspects.

Nanoworm coated surfaces were tested against live H3N2 influenza enveloped virus according to the following procedure. A 10 μL droplet at 1.3x105 PFU/mL of virus was added to the nanoworm-coated surfaces. The virus used was A/Switzerland/9715293/2013(H3N2) strain. The surfaces were incubated for 30 min at room temperature, and then washed with 190 μL of PBS+trypsin (2 μg/mL). A 2-fold serial dilutions of the wash, and 50 μL of the dilutions was added to the Vero cells in each well. The wells were incubated for 1 h at 37° C. The virus wash was removed and overlay media (M199 media with 1.5% CMC, 2% FCS, 1:100 PenStrep, 2 μg/mL Trypsin) added, and then incubate for 72 h at 37° C. The overlay and fix cells were removed by addition of 100 μL/well of ice-cold 80% acetone/20% PBS, and incubated for 20 min at −20° C. The acetone was removed and allow to air-dry overnight. An immunostain plate with hFI6v3 at 2 μg/mL and goat anti-human IRDYE800 secondary antibody at 1:2000 dilution was then carried out. The plaque forming units counted and the plaque forming units per ml calculated. FIG. 11 shows examples of antiviral activity against H3N2 influenza virus for nanoworm coated surfaces according to certain aspects. Each of the nanoworm coated surfaces (A, B, C, D) showed antiviral properties with a reduced level of plaque forming units in comparison to the control.

Cloned Attenuated AAV-HA Virus by Solution Assay Protocol

Figure 12:
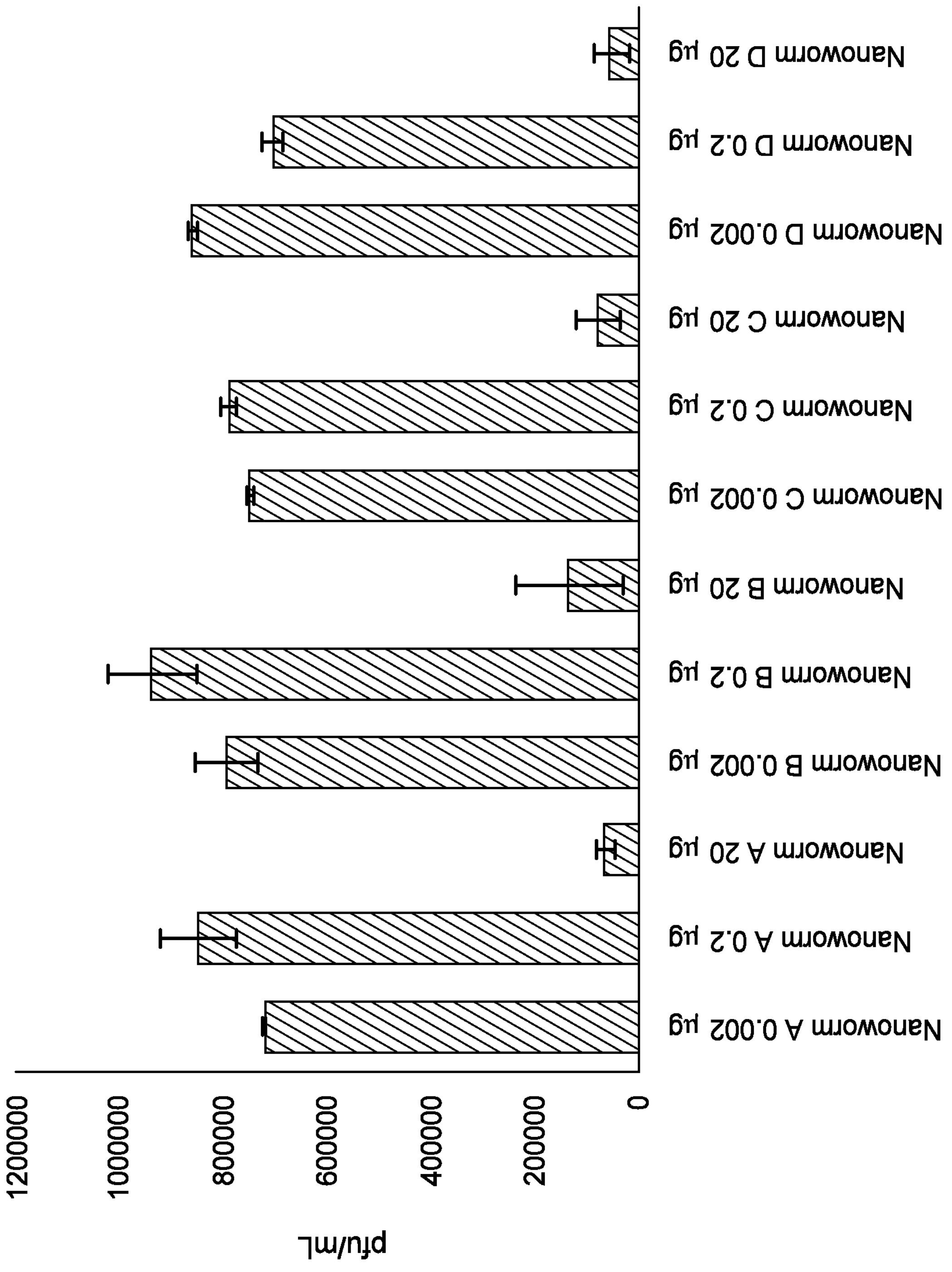
FIG. 12 shows examples of the antiviral activity against AAV-HA virus for nanoworm coated surfaces according to certain aspects.

Nanoworm coated surfaces were tested against cloned attenuated AAV-HA virus according to the following procedure. Solution assays of 0.002, 0.2, and 20 micrograms (μg) of nanoworm polymers were diluted in 250 microliters (μL) of DMEM (FCS free) medium. 1 μL of AAV-HA stock solution containing 1.0x109 PFU/mL was added, and then mixed and incubated 30 min at room temperature. 250 μL/well was added to the HEK293 cells and incubated for 1 h at 37° C. The virus solution was removed from the cells, and DMEM media added to the wells and further incubated for 1 h at 37° C. The cells were harvested and their genomic DNA extracted for real-time PCR. Quantification of the extracted DNA was correlated to pfu/ml. FIG. 12 shows examples of the antiviral activity against AAV-HA virus for nanoworm coated surfaces according to certain aspects. Each of the nanoworm coated surfaces (A, B, C, D) showed increased antiviral properties when the amounts of nanoworm polymer were increased to 20 μg.

Cloned Attenuated AAV-HA Virus by Surface Assay Protocol

Figure 13:
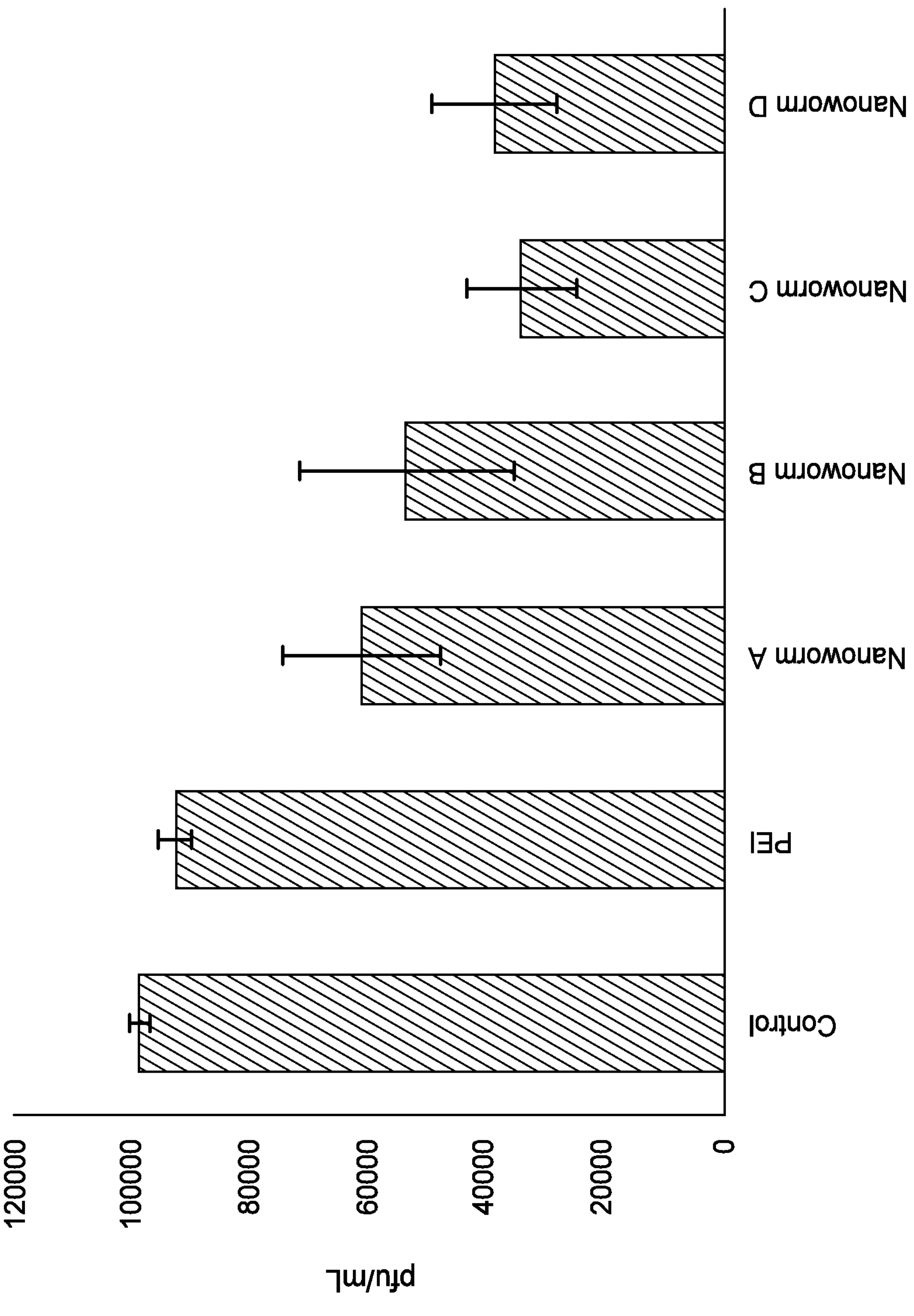
FIG. 13 shows examples of antiviral activity against AAV-HA virus for nanoworm coated surfaces according to certain aspects.

Nanoworm coated surfaces were tested against cloned attenuated AAV-HA virus according to the following procedure. Surface assay of 10 μL droplet at 1.0x106 PFU/mL of AAV-HA virus diluted in PBS buffer was added to the nanoworm coated surfaces and incubated for 30 min at room temperature. The surfaces were washed with 250 μL of PBS, and vortexed five times for 2 sec each. 250 μL was added to each well containing HEK293 cells, and incubated for 1 h at 37° C. The virus solution was removed from the cells, and DMEM media added to the wells and further incubated for 1 h at 37° C. The cells were harvested and their genomic DNA extracted for real-time PCR. Quantification of the extracted DNA was correlated to pfu/ml. FIG. 13 shows examples of antiviral activity against AAV-HA virus for nanoworm coated surfaces according to certain aspects. Each of the nanoworm coated surfaces (A, B, C, D) showed antiviral properties with a reduced level of plaque forming units in comparison to the control and in comparison to the antiviral properties of PEI.

Nanoworm Sprayed Surfaces Against AAV-HA Recombinant Virus (Capsid)

Figure 18:
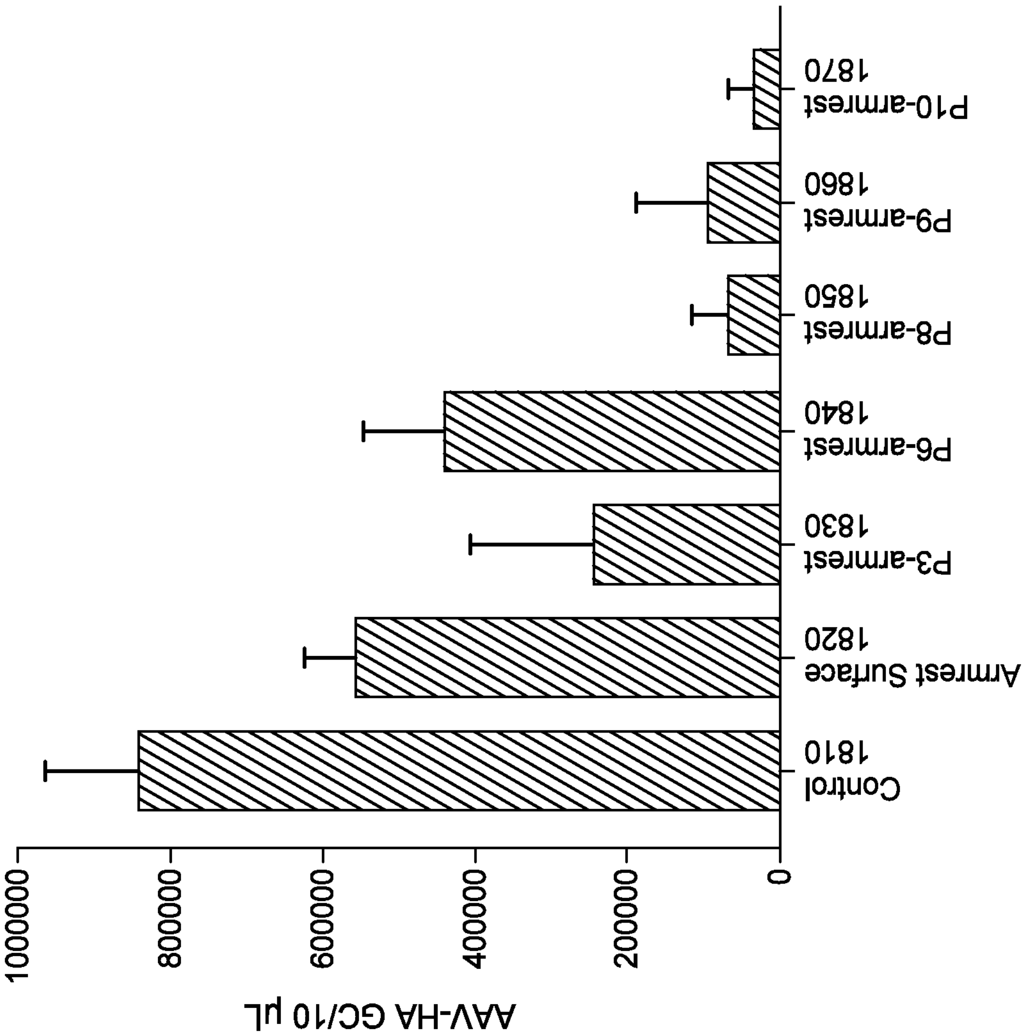
FIGS. 18-21 show the reduction of virus activity on application over various surfaces.

Nanoworm sprayed surfaces were tested against AAV-HA recombinant non-enveloped virus (capsid). A solution of 10 μl with a pH buffered at 6.5 and with 1,000,000 genome copies of AAV-HA virus were applied to various surfaces. FIG. 18 shows the reduction of virus activity on application over various surfaces. Surface 1810 was a control glass slip surface treated with piranha solution and without any sprayed nanoworm coating. Surface 1820 was an armrest surface and without any sprayed nanoworm coating. Surface 1830 was an armrest surface with a nanoworm coating of Nanoworm Example 17 (P3). Surface 1840 was an armrest surface and with a nanoworm coating of Nanoworm Example 18 (P6). Surface 1850 was an armrest surface and with a nanoworm coating of Nanoworm Example 20 (P8). Surface 1860 was an armrest surface and with a nanoworm coating of Nanoworm Example 21 (P9). Surface 1870 was an armrest surface and with a nanoworm coating of Nanoworm Example 19 (P10). The surfaces 1830-1870 were formed by five sprays of a nanoworm solution. Each of the surfaces 1830-1870 with a nanoworm coating showed an increased antiviral effect in comparison to the surfaces 1810-1820.

Figure 19:
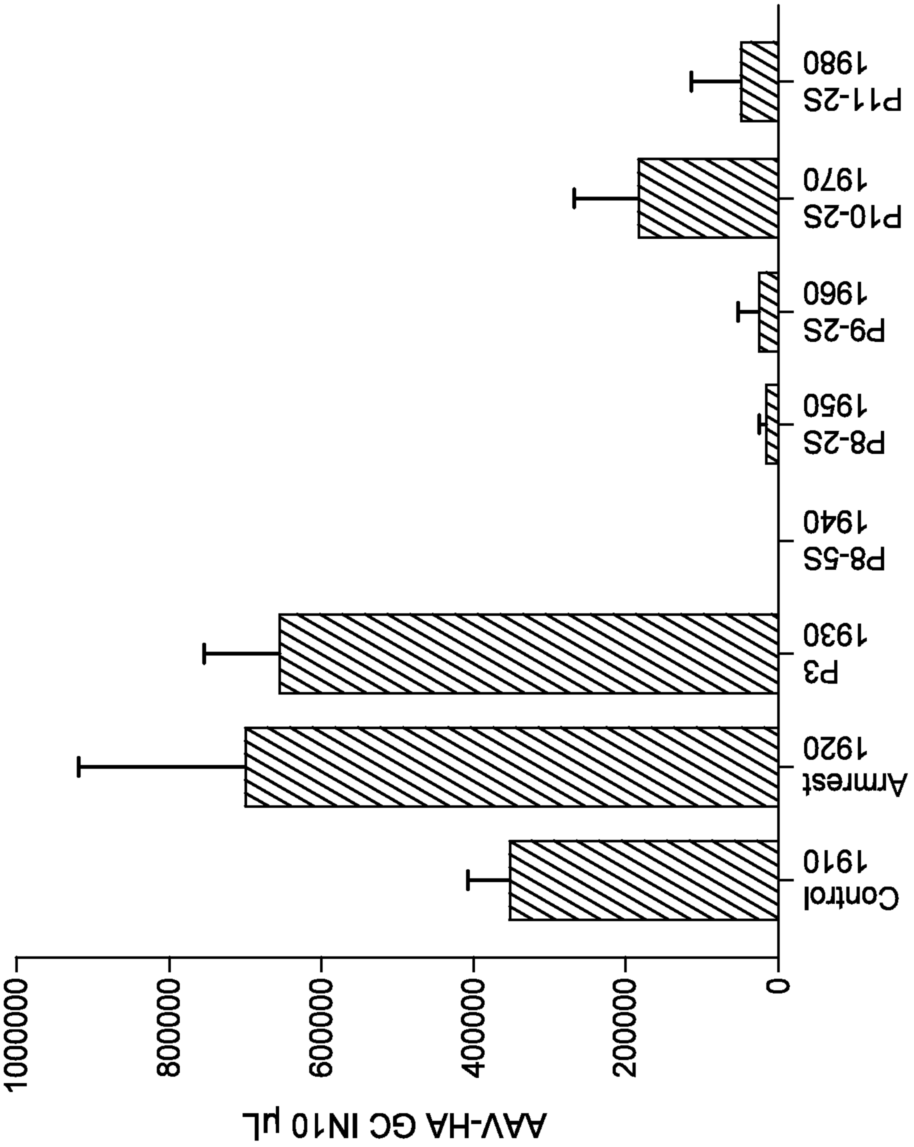

Nanoworm sprayed surfaces were tested against AAV-HA recombinant non-enveloped virus (capsid). A solution of 10 μl with a pH buffered at 6.5 and with 1,000,000 genome copies of AAV-HA virus were applied to various surfaces. FIG. 19 shows the reduction of virus activity on application over various surfaces. Surface 1910 was a control glass slip surface treated with piranha solution and without any sprayed nanoworm coating. Surface 1920 was an armrest surface and without any sprayed nanoworm coating. Surface 1930 was an armrest surface with a nanoworm coating of Nanoworm Example 17 (P3). Surfaces 1940-1950 were armrest surfaces and with nanoworm coatings of Nanoworm Example 20 (P8). Surface 1960 was an armrest surface and with a nanoworm coating of Nanoworm Example 21 (P9). Surface 1970 was an armrest surface and with a nanoworm coating of Nanoworm Example 19 (P10). Surface 1980 was an armrest surface and with a nanoworm coating of Nanoworm Example 22 (P11). The surfaces 1940 was formed by two sprays of a nanoworm solution. The surfaces 1950-1980 were formed by two sprays of a nanoworm solution. Each of the surfaces 1940-1980 with a nanoworm coating showed an increased antiviral effect in comparison to the surfaces 1910-1920.

Figure 20:
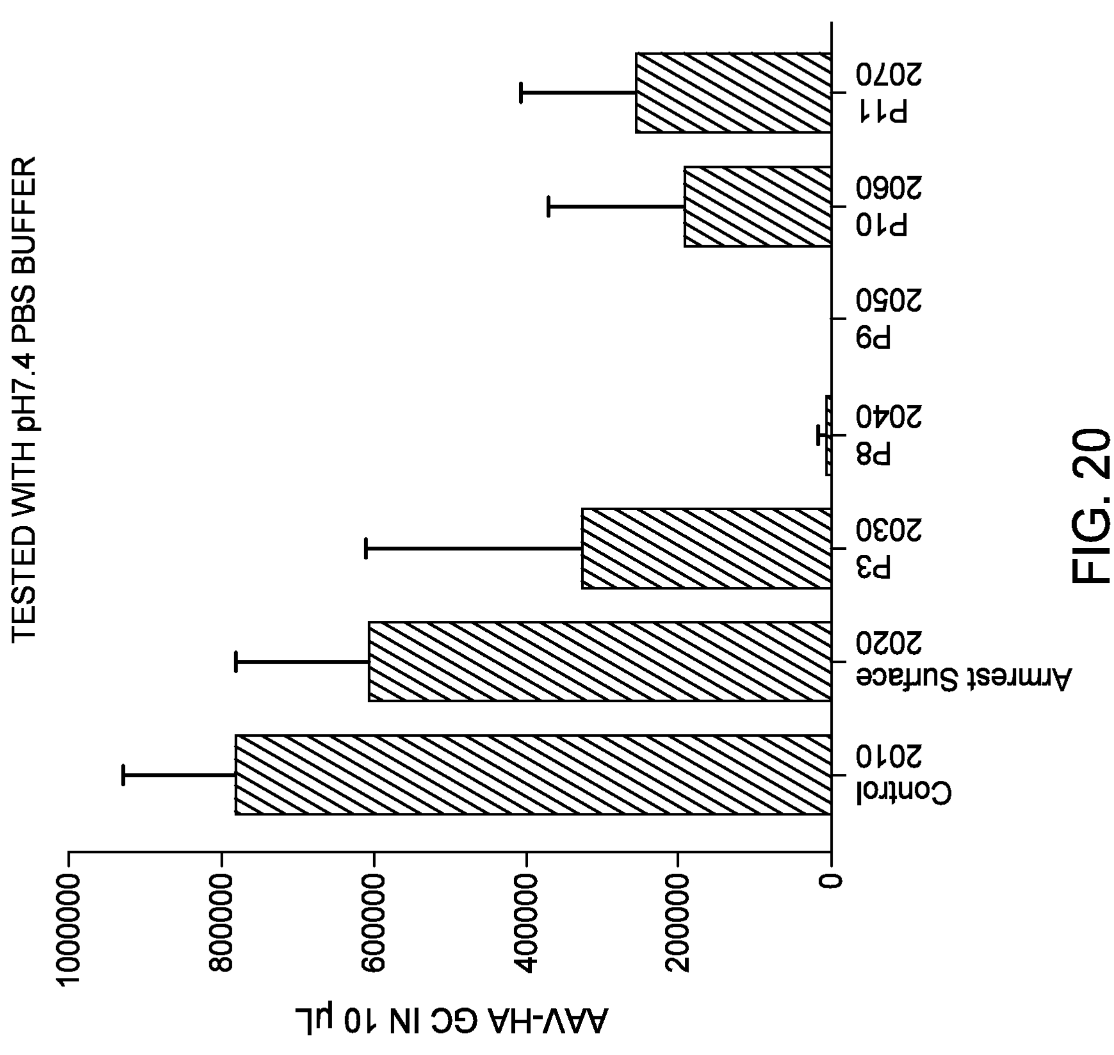

Nanoworm sprayed surfaces were tested against AAV-HA recombinant non-enveloped virus (capsid). A solution of 10 μl with a pH buffered at 7.4 and with 1,000,000 genome copies of AAV-HA virus were applied to various surfaces. FIG. 20 shows the reduction of virus activity on application over various surfaces. Surface 2010 was a control glass slip surface treated with piranha solution and without any sprayed nanoworm coating. Surface 2020 was an armrest surface and without any sprayed nanoworm coating. Surface 2030 was an armrest surface with a nanoworm coating of Nanoworm Example 17 (P3). Surface 2040 was an armrest surface and with a nanoworm coating of Nanoworm Example 20 (P8). Surface 2050 was an armrest surface and with a nanoworm coating of Nanoworm Example 21 (P9). Surface 2060 was an armrest surface and with a nanoworm coating of Nanoworm Example 19 (P10). Surface 2070 was an armrest surface and with a nanoworm coating of Nanoworm Example 22 (P11). The surfaces 2030-2070 were formed by five sprays of a nanoworm solution. Each of the surfaces 2030-2070 with a nanoworm coating showed an increased antiviral effect in comparison to the surfaces 2010-2020.

Nanoworm Sprayed Surfaces Against Coronavirus (Enveloped Virus)

Figure 21:
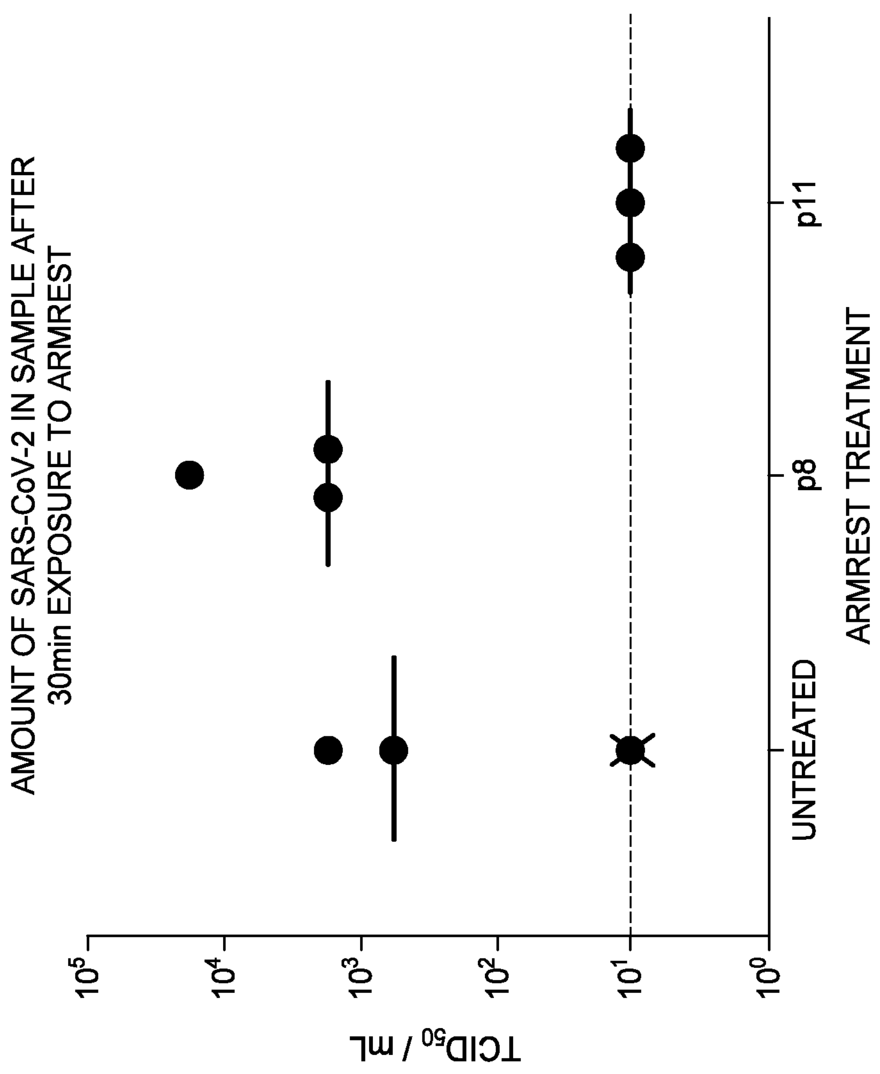

Nanoworm sprayed surfaces were tested against SARS-CoV-2 (enveloped virus) capsid. An amount of SARS-CoV-2 sample buffered at pH of 6.5 applied to various surfaces. FIG. 21 shows the reduction of virus activity on application over various surfaces after 30 minute exposure. Surface 2010 was an armrest surface and without any sprayed nanoworm coating. Surface 2020 was an armrest surface and with a nanoworm coating of Nanoworm Example 20 (P8), Surface 2030 was an armrest surface and with a nanoworm coating of Nanoworm Example 22 (P11). The surface 2030 showed a reduction in virus activity below the detection limit. It is believes that the Nanoworm Example 22 (P11) has increased antiviral effect in comparison to Nanoworm Example 20 (P8) due to the glycan-mimic targeting of the poly-sugar group of Nanoworm Example 22 whereas Nanoworm Example 20 lacks a poly-sugar group.

The descriptions of the various aspects of the present disclosure have been presented for purposes of illustration, but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects disclosed herein.

What is claimed is:

1. A nanoworm, comprising:

a plurality of alkene units; and a first set of a plurality of macro chain transfer agent (macroCTA) polymer units, wherein the macroCTA polymer units of the first set include R1 groups from reversible addition-fragmentation chain-transfer agents; and wherein the RI groups of the macroCTA polymer units of the first set comprise a carboxylic acid.

2. The nanoworm of claim 1, wherein the first set of the plurality of macroCTA polymer units has a lower critical solution temperature (LCST) in water from −20° C. to +100° C.

3. The nanoworm of claim 1, wherein the first set of the plurality of macroCTA polymer units is configured to be responsive to temperature and configured to be responsive to an environmental condition selected from a group consisting of pH, salinity concentration, and light.

4. The nanoworm of claim 1, wherein the macroCTA polymer further comprises a second set of macroCTA polymer units.

5. The nanoworm of claim 4, wherein the macroCTA polymer units of the second set comprise functionalized quaternized amines selected from a functional group consisting of an alkyl group, a carboxylic acid, an alkyne, a pyridine, a dopamine, a thiolactone, a biotin, an azide, a peptide sequence, a sugar sequence, a protease, a glycanase, a polymer, and combinations thereof.

6. The nanoworm of claim 5, wherein the macroCTA polymer units of the second set comprises two or more sets of functionalized quaternized amines, each comprising a peptide sequence.

7. The nanoworm of claim 4, wherein the macroCTA polymer units of the second set comprises functionalized quaternized amines of long alkyl quaternized groups or short alkyl quaternized groups, the short alkyl groups having one to four carbons and the long alkyl quaternized groups having five or more carbons.

8. The nanoworm of claim 1, wherein the nanoworm further comprises:

a second set of a plurality of macroCTA polymer units, wherein the macroCTA polymer units of the second set include R1 groups from reversible addition-fragmentation chain-transfer agents, wherein the first set of the plurality of macroCTA polymers units is different from the second set of the plurality of macroCTA polymers units.

9. The nanoworm of claim 1, wherein the macroCTA polymer units of the first set comprise a polymer selected from a group consisting of poly(N-isopropylacrylamide) (PNIPAM), poly(N,N-(dimethylamino) ethyl methacrylate) (F), poly(N-acetoxylethyl acrylamide) (PNAEAA), poly (acryloylglycine ethyl ester) (PNAGEE), poly((ethylene glycol) methyl ether methacrylate) (PEGM EMA), poly ((propylene glycol) methacrylate) (PPGMA), poly(N,N-dimethylacrylamide) (PDMA), poly(N-decylacrylamide) (PDCA), poly(N,N-diethylacrylamide) (PDEA), poly(N-acryloylglycine) (PNAG), poly(N-acryloylglycine methyl ester) (PNAGME), poly(N-acryloylglycine ethyl ester) (PNAGEE) and poly(N-acryloylglycine propyl ester) (PNAGPE), polyacrylamides, polyacrylates, and copolymers thereof.

10. The nanoworm of claim 1, wherein the nanoworm comprises at least a hydrophilic portion.

11. The nanoworm of claim 1, wherein the nanoworm comprises a hydrophilic portion and a hydrophobic portion.

12. The nanoworm of claim 1, further comprising a plurality of grafted polymers grafted to at least a portion of the first set of the plurality of macroCTA polymer units.

13. The nanoworm of claim 12, wherein the grafted polymers comprise functionalized quaternized amines selected from a functional group consisting of an alkyl, a carboxylic acid, an alkyne, a pyridine, a dopamine, a thiolactone, a biotin, an azide, a peptide sequence, a sugar sequence, a protease, a glycanase, and combinations thereof.

14. The nanoworm of claim 12, wherein the grafted polymers comprise two or more sets of functionalized quaternized amines selected from a functional group consisting of an alkyl, a carboxylic acid, an alkyne, a pyridine, a dopamine, a thiolactone, a biotin, an azide, a peptide sequence, a sugar sequence, a protease, a glycanase, and combinations thereof.

15. The nanoworm of claim 12, wherein the grafted polymers comprise a first set of functionalized quaternized amines of short alkyl quaternized groups and a second set of functionalized quaternized amines, the short alkyl groups having one to four carbons and the long alkyl quaternized groups having five or more carbons.

16. The nanoworm of claim 12, wherein the grafted polymers comprise:

a first set of functionalized quaternized amine groups comprising a peptide sequence, and a second set of functionalized quaternized amine groups comprising a sugar sequence.

17. The nanoworm of claim 12, wherein the grafted polymers are grafted to the R1 groups of the macroCTA polymer units of the first set.

18. The nanoworm of claim 12, wherein the grafted polymers are grafted to quaternary amines of the macroCTA polymer units of the first set.

19. The nanoworm of claim 12, wherein a first set of the plurality of grafted polymers is grafted to the RI groups of the macroCTA polymer units of the first set, and wherein a second set of the plurality of the plurality of grafted polymers is grafted to quaternary amines of the macroCTA polymer units of the first set.

20. The nanoworm of claim 1, wherein the RI groups of the macroCTA polymer units of the first set further comprise a functional groups selected from a group consisting of an alkyne, a pyridine, a dopamine, a thiolactone, a biotin, an azide, a peptide sequence, a sugar sequence, a protease, a glycanase, a polymer, and combinations thereof.

* * * * *